United States Patent [19]
Irani

[11] Patent Number: 5,830,700
[45] Date of Patent: Nov. 3, 1998

[54] HYBRID PROTEINS HAVING CROSS-LINKING AND TISSUE-BINDING ACTIVITIES

[76] Inventor: Meher Irani, 3503 NE. 100th, Seattle, Wash. 98125

[21] Appl. No.: 551,356

[22] Filed: Nov. 1, 1995

Related U.S. Application Data

[63] Continuation of Ser. No. 349,762, Dec. 5, 1994, abandoned, which is a continuation of Ser. No. 998,271, Dec. 30, 1992, abandoned.

[51] Int. Cl.$^6$ .......................... C12P 21/04; C07K 19/00; C07K 14/435; C12N 15/62
[52] U.S. Cl. .............. 435/69.7; 435/252.3; 435/254.11; 435/325; 530/350; 530/380; 530/381; 530/382; 536/23.4; 536/24.1; 514/12; 514/21
[58] Field of Search ..................... 530/350, 380, 530/402, 381, 382; 514/12, 21; 435/69.6, 69.7, 320.1, 240.1; 536/23.4

[56] References Cited

U.S. PATENT DOCUMENTS

| | | | |
|---|---|---|---|
| 4,589,881 | 5/1986 | Pierschbacher et al. | 623/11 |
| 4,614,517 | 9/1986 | Ruoslahti et al. | 530/330 |
| 4,627,879 | 12/1986 | Rose et al. | 106/124 |
| 4,661,111 | 4/1987 | Ruoslahti et al. | 623/11 |
| 5,136,023 | 8/1992 | Hashino et al. | 530/350 |
| 5,428,014 | 6/1995 | Labroo et al. | 514/12 |
| 5,514,579 | 5/1996 | O'Hara et al. | 435/240.2 |

FOREIGN PATENT DOCUMENTS

| | | |
|---|---|---|
| 207751 | 1/1987 | European Pat. Off. |
| 399806 | 11/1990 | European Pat. Off. |
| 88/03810 | 6/1988 | WIPO |
| 90/13653 | 11/1990 | WIPO |

OTHER PUBLICATIONS

Sekiguchi et al., *Essays in Biochemistry* 26: 39–48, 1991.
Prieto et al., *J. Cell. Biol.* 119: 663–678, 1992.
Lord et al., *J. Biol. Chem.* 265: 838–843, 1990.
Simon et al. The glutamine residues in transglutaminase–catalyzed cross–linking of involucrin. The Journal of Biological Chemistry. vol. 263, No. 34, pp. 18093–18098, Dec. 5, 1988.
Hohl et al. Charcterization of human loricrin. The Journal of Biological Chemistry. vol. 266, No. 10, pp. 6626–6636, Apr. 5, 1991.
Rixon et al., *Biochemistry* 22: 3237–3244, 1983.
Chung et al., *Biochemistry* 22: 3250–3256, 1983.
Doolittle et al., *Nature* 280: 464–468, 1979.
Pan et al., *Proc. Natl. Acad. Sci. USA* 89:2066–2070, 1992.
Vibe–Pedersen et al., *EMBO J.* 3: 2511–2516, 1984.
Obara et al., *Cell* 53: 649–657, 1988.
Kornblihtt et al., *Nuc. Acids Res.* 12: 5853–5868, 1984.
Sekiguchi et al., *Proc. Natl. Acad. Sci. USA* 77: 2661–2665, 1980.
Kornblihtt et al., *Proc. Natl. Acad. Sci. USA*: 80:3218–3222, 1983.
Hirano et al., *Proc. Natl. Acad. Sci. USA* 80: 46–50, 1983.
Kornblihtt et al., *EMBO J.* 4: 1755–1759, 1985.
Pierschbacher et al., *J. Biol. Chem.* 257: 9593–9597, 1982.
Schwarzbauer et al., *Proc. Natl. Acad. Sci. USA* 84: 754–758, 1987.
Dufour et al., *Exp. Cell. Res.* 193: 331–338, 1991.
Yamada, *Curr. Opin. Cell. Biol.* 1: 956–963, 1989.
Obara et al., *FEBS LETT.* 213: 261–264, 1987.
Yamada, *Ann. Rev. Biochem.* 52: 761–799, 1983.
Yabkowitz et al., *J. Biol. Chem.* 264: 10888–10896, 1989.
Fu et al., *Biochemistry* 31: 11968–11972, 1992.
Eckert et al., *Cell* 46: 583–589, 1986.
Robson et al. 1986. Introduction to Protein and Protein Engineering, Elsevier, New York, p. 41.
Pongor, S. 1987. Methods in Enzymology, 154: 450–473.

*Primary Examiner*—Stephen Walsh
*Assistant Examiner*—Brian Lathrop

[57] ABSTRACT

Hybrid proteins having cross-linking and tissue-binding activities, DNA molecules encoding such proteins and methods for producing the hybrid proteins from recombinant host cells are disclosed. The hybrid proteins disclosed herein are useful in tissue sealant and wound healing formulations.

23 Claims, 5 Drawing Sheets

HYBRID PROTEINS HAVING CROSS-LINKING AND TISSUE-BINDING ACTIVITIES

This is a Continuation of application Ser. No. 08/349,762, filed Dec. 5,1994,now abandoned, which is a Continuation of application Ser. No. 07/998,271, filed Dec. 30 1992, now abandoned.

TECHNICAL FIELD

The present invention relates generally toward methods for producing recombinant hybrid proteins, and more specifically, to methods for producing hybrid proteins from host cells through the use of recombinant DNA techniques.

BACKGROUND OF THE INVENTION

The utilization of tissue sealants to replace or augment the use of mechanical wound closure devices has expanded in recent years in many surgical and trauma applications. Tissue sealants include biological adhesives (e.g. fibrin-based adhesives) and synthetic preparations (e.g. cyanoacrylates). It is widely acknowledged that the use of synthetic preparations of tissue sealants is limited due to their toxicity and limited applications. Biological tissue adhesives have demonstrated utility in cases where the use of mechanical devices to close wounds is insufficient, such as in joining blood vessels, closing holes in the dura, and in surgery on small or delicate tissues such as in the eye or ear.

Fibrin-based biological tissue adhesives generally contain fibrinogen, factor XIII and thrombin as principal ingredients, although in practice biological tissue adhesives are derived from whole blood and contain additional blood proteins. The fibrinogen and factor XIII components of these adhesives are prepared from pooled human plasma by cryoprecipitation (e.g. U.S. Pats. Nos. 4,377,572; 4,362,567; 4,909,251), by ethanol precipitation (e.g. U.S. Pat. No. 4,442,655) or from single donor plasma (e.g. U.S. Pat. No. 4,627,879; Spotnitz et al., *Am. Surg.* 55: 166–168, 1989). The resultant fibrinogen/factor XIII preparation is mixed with bovine thrombin immediately before use to convert the fibrinogen to fibrin and activate the factor XIII, thus initiating coagulation of the adhesive.

Fibrin-based tissue adhesives, in their current form, have significant drawbacks that include poor standardization, lack of quality control from batch to batch and the possibility of transmission of human immunodeficiency virus (HIV), hepatitis virus and other etiologic agents. While recombinant production of thrombin and factor XIII have been reported, and while these proteins might be used in biological tissue adhesives, the biological tissue adhesives still rely on large amounts of fibrinogen that is obtained from pooled human blood. At present, current fibrin(ogen)-based tissue adhesives are not approved for use in the United States.

There is therefore a need in the art for tissue adhesive components, particularly components that facilitate cross-linking to improve clot strength, that are prepared at high levels with reproducible activity levels and which do not carry the possibility of transmission of viral or other etiologic agents. The present invention addresses these needs by providing recombinant hybrid proteins that provide cross-linking and tissue-adhesive properties and that may be prepared at high levels.

DISCLOSURE OF THE INVENTION

Briefly stated, the present invention provides hybrid proteins having cross-linking and tissue-binding activities, DNA molecules encoding such hybrid proteins and methods for producing hybrid proteins by recombinant means. In one aspect of the invention, the hybrid proteins comprise a tissue-binding domain from a first protein covalently linked to a cross-linking domain from a second protein. Within a related aspect of the invention, the tissue-binding domain of the first protein is a heparin binding domain of thrombospondin, a heparin binding domain of fibronectin, a collagen binding domain of fibronectin or a cell binding domain of fibronectin. Within a preferred embodiment, the tissue-binding domain of the first protein comprises the amino acid sequence of Sequence ID No. 6 from Alanine, amino acid 2 to Glutamic acid, amino acid number 926. Within another related aspect of the invention, the cross-linking domain of the second protein comprises the carboxy-terminal 103 amino acids of loricrin, the ten amino acid repeat beginning with glutamine, amino acid number 496 of involucrin or the 400 amino-terminal amino acids of the fibrinogen α chain. Within a preferred embodiment of the invention, the cross-linking domain of the second protein comprises the amino acid sequence of Sequence ID No. 6 from Glycine, amino acid number 928 to Proline, amino acid number 1336. Within a particularly preferred embodiment, the hybrid protein comprises the amino acid sequence of Sequence ID No. 6 from alanine, amino acid number 2 to proline, amino acid number 1336.

The present invention provides DNA molecules encoding hybrid proteins of the present invention comprising a first DNA segment encoding a tissue-binding domain from a first protein joined to a second DNA segment encoding a cross-linking domain from a second protein. In one embodiment, the first DNA segment comprises the nucleotide sequence of Sequence ID No. 5 from nucleotide 3 to nucleotide 2780. In another embodiment, the second DNA segment comprises the nucleotide sequence of Sequence ID No. 5 from nucleotide 2784 to nucleotide 4013. In a preferred embodiment, the DNA molecule comprises the nucleotide sequence of Sequence ID Number 5 from nucleotide 3 to nucleotide 4013.

In related embodiments of the invention, DNA constructs are provided which comprise a DNA molecule encoding a hybrid protein, wherein said DNA molecule comprises a first DNA segment encoding a tissue-binding domain from a first protein joined to a second DNA segment encoding a cross-linking domain from a second protein and wherein said DNA molecule is operably linked to other DNA segments required for the expression of the DNA molecule. Other embodiments of the invention concern host cells containing the DNA constructs of the present invention and methods of producing hybrid proteins.

DETAILED DESCRIPTION OF THE INVENTION

Figure 1:
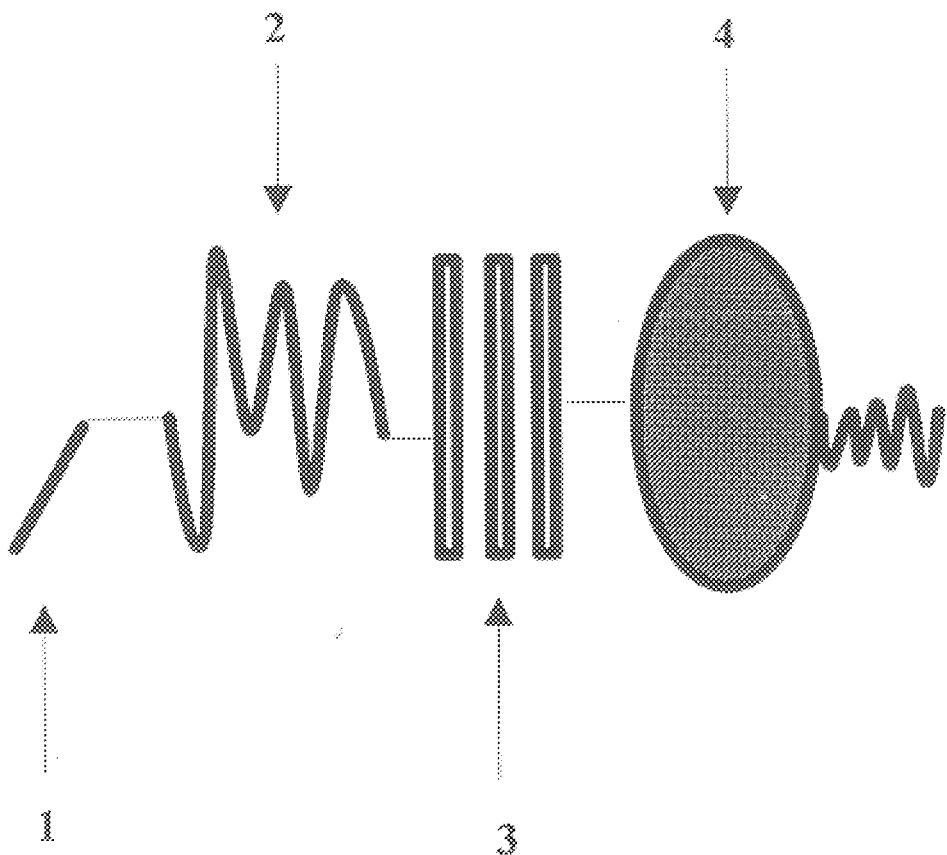
FIG. 1 discloses a representative hybrid protein containing (1) an N-terminal end-to-end inter-chain cross-linking domain, (2) a domain that promotes inter-chain cross-linking; (3) a domain that confers tissue binding activity; and (4) a carboxy-terminal domain that promotes end-to-end inter-chain cross-linking.
Figure 2:
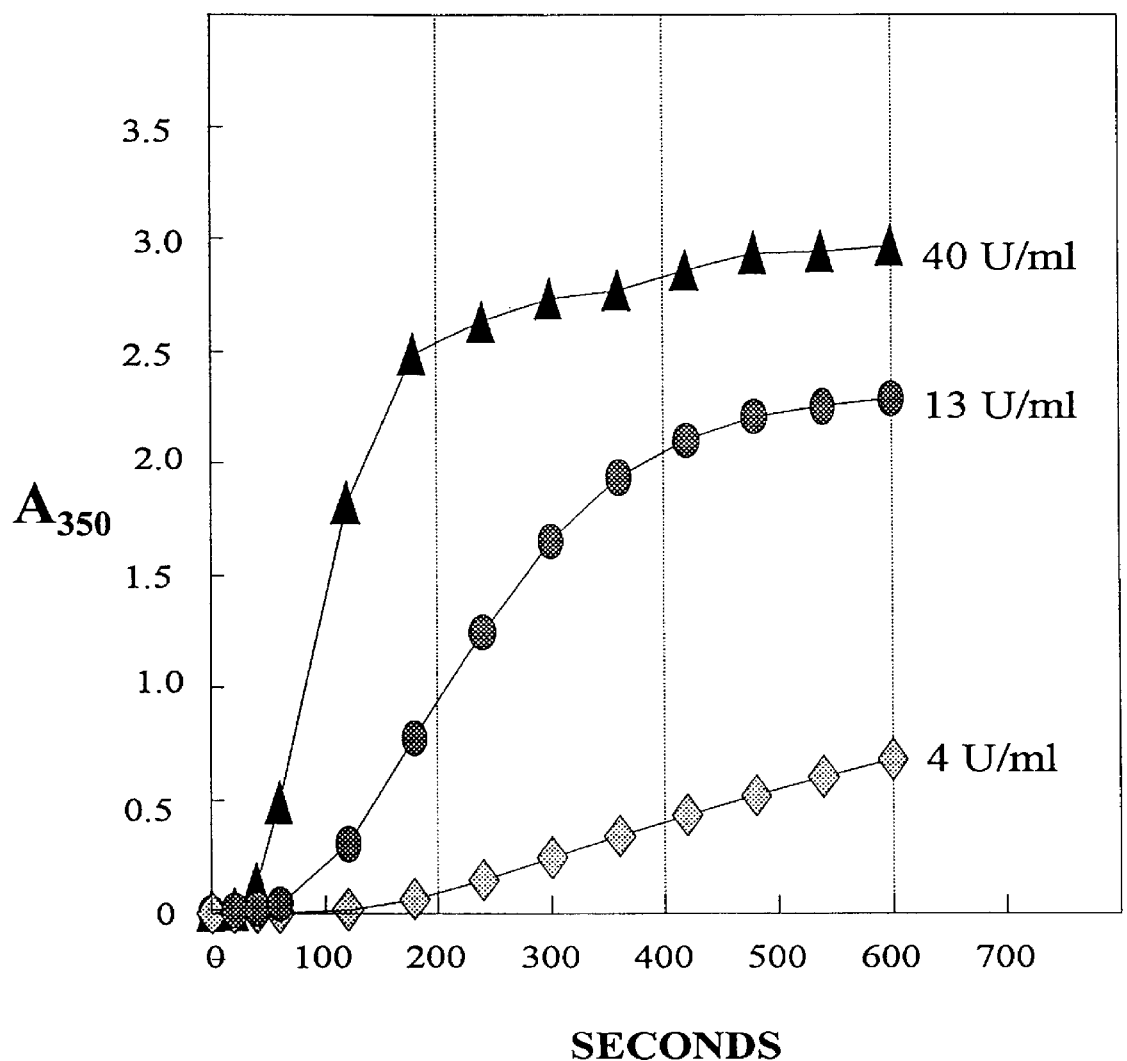
FIGS. 2–5 disclose absorbance time courses of representative cross-linking assays carried out in the presence of varying levels of factor XIII (activated to factor XIIIa via thrombin during the assay) or factor XIIIa.
Figure 3:
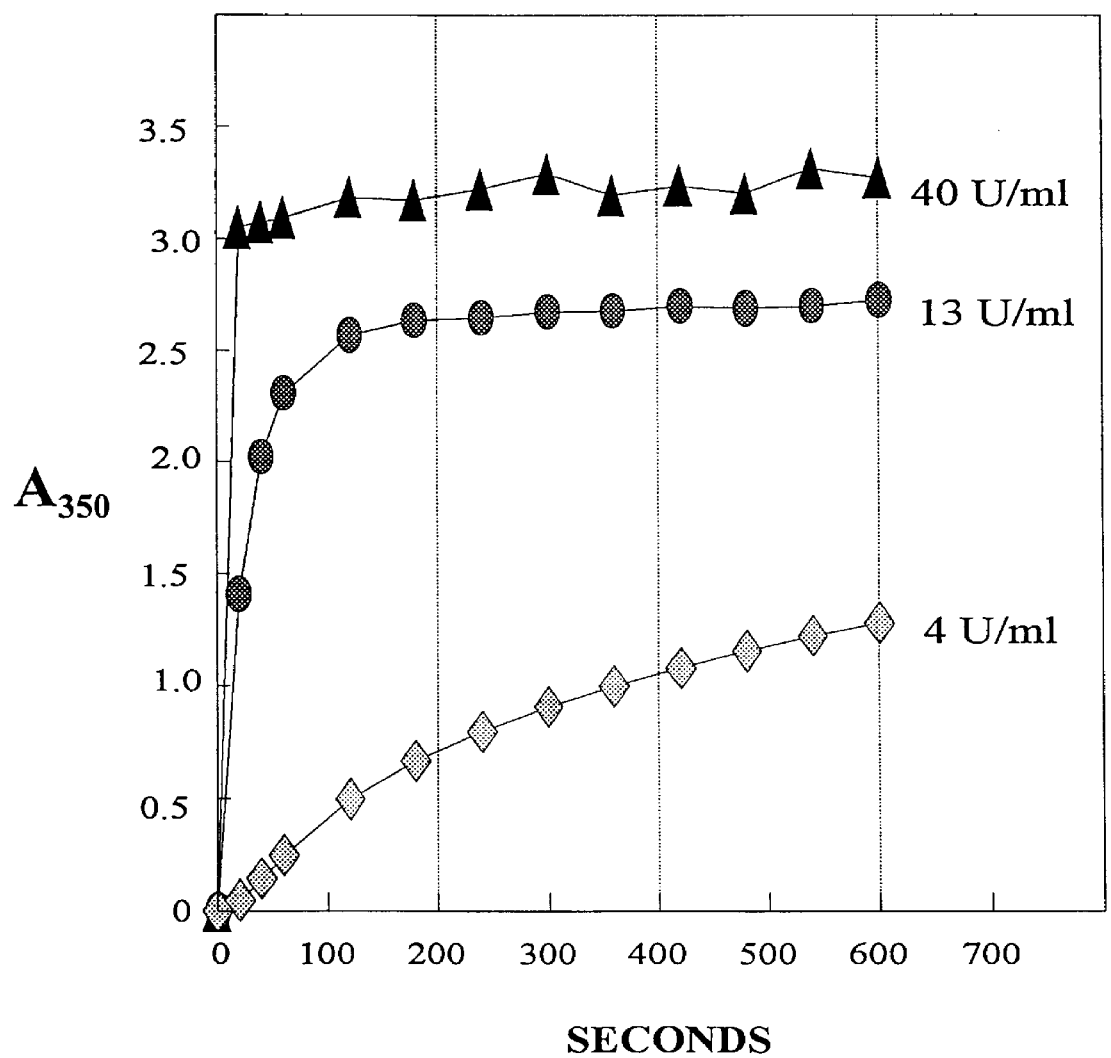
Figure 4:
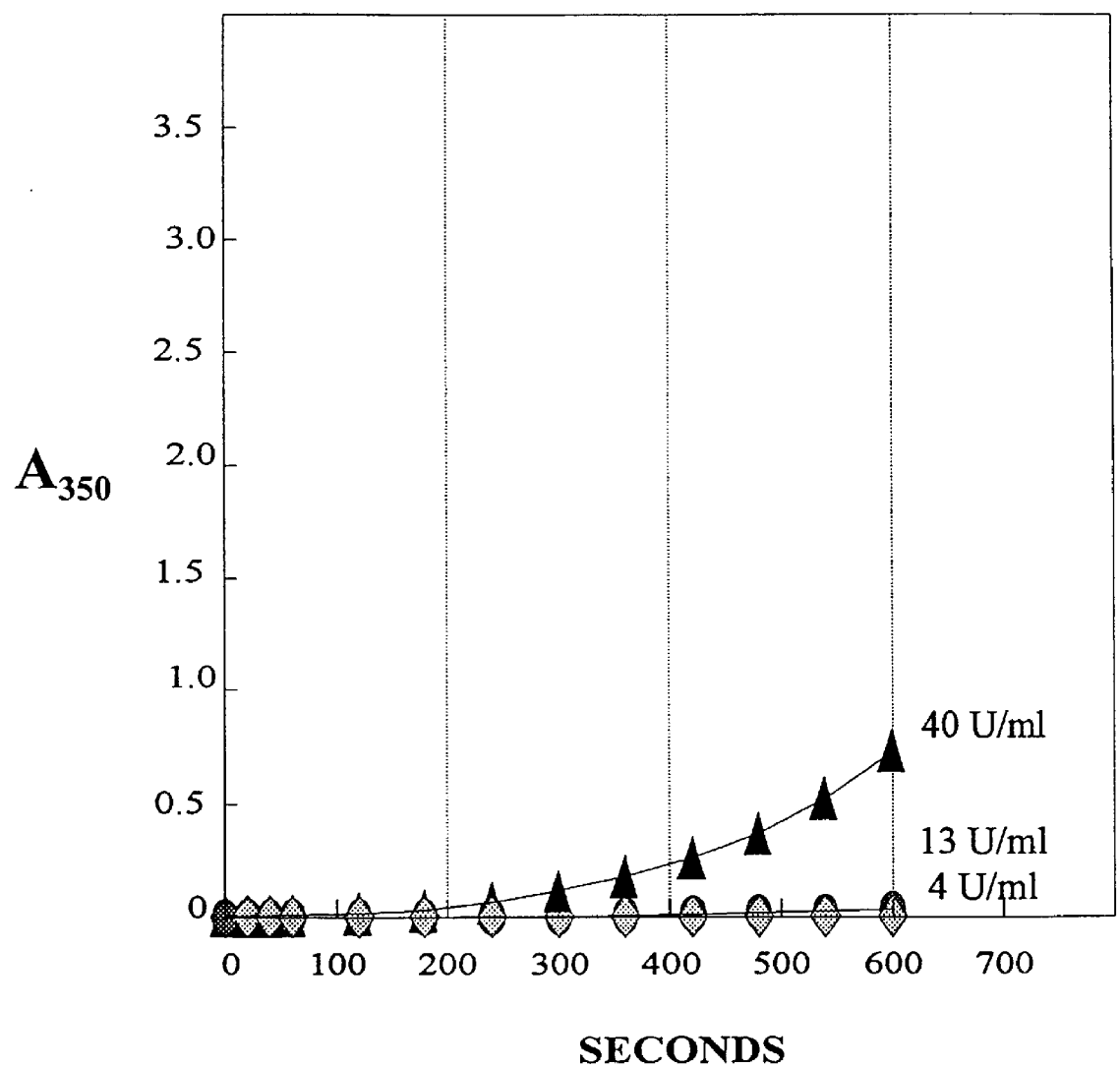
Figure 5:
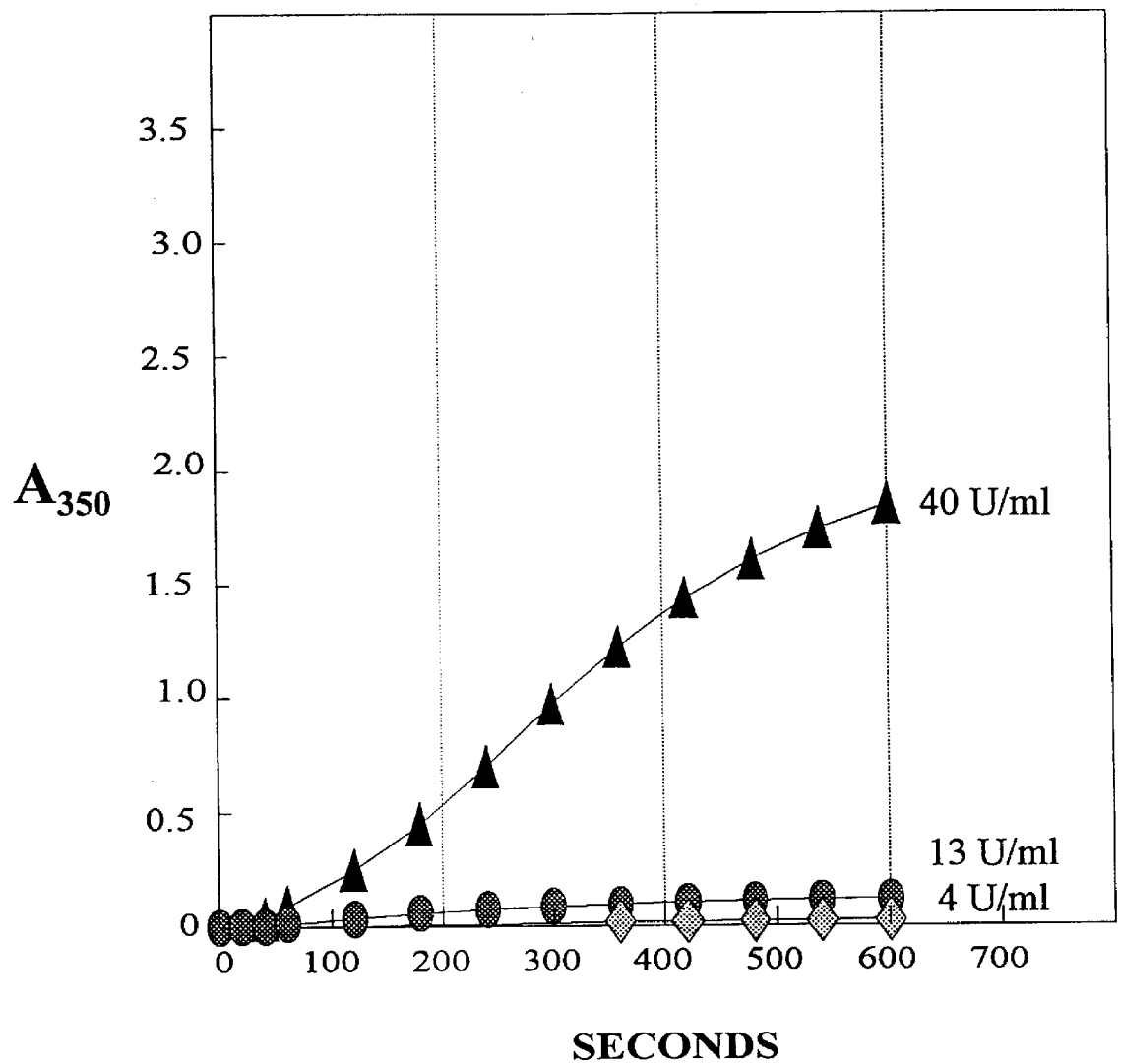

The present invention provides novel hybrid proteins having cross-linking and tissue adhesive activities. The hybrid proteins comprise a cross-linking domain from a first protein covalently linked to a tissue-binding domain from a second protein. The hybrid proteins of the present invention are capable of cross-linking to themselves and to other proteins such as fibrin and fibrinogen and are capable of adhering to cell surfaces and/or extracellular matrix components. While not wishing to be bound by a graphical representation, FIG. 1 shows a representative hybrid protein containing an N-terminal end-to-end inter-chain cross-linking domain; a domain that promotes inter-chain cross-linking; a domain that confers tissue binding activity; and a carboxy-terminal domain that promotes end-to-end inter-chain cross-linking. As used herein, cross-linking refers to the formation of covalent bonds between polypeptides.

The hybrid proteins of the present invention are useful as components of tissue sealant formulations to provide matrix material and to improve clot strength over a wound site, and as components in formulations that promote wound healing. The proteins of the present invention may contain native (i.e. wild-type) protein domains as well as domains that are allelic variants and genetically engineered or synthetic variants of the respective naturally occurring domains. Such variants are characterized by the presence of conservative amino acid substitutions and/or other minor additions, substitutions or deletions of amino acids.

As used within the context of the present invention, tissue-binding domains include protein domains containing amino acid sequences that facilitate adherence to cell surfaces and/or to extracellular matrix components such as collagen, fibronectin, hyaluronic acid and glycosaminoglycans. Fibronectin, for example, contains the sequence Gly-Arg-Gly-Asp-Ser (from amino acid 1614 through amino acid 1618 of Sequence I.D. No. 2) that has been shown to be central to cell recognition by the fibronectin receptor (for review see Yamada, *Current Opinion in Cell Biology* 1: 956–963, 1989) The heparin binding domains of fibronectin (Sekiguchi et al., *Proc. Natl. Acad. Sci. USA* 77: 2661–2665, 1980), and thrombospondin contain sequences that recognize heparin sulfate-containing glycosaminoglycans which are extracellular matrix components. The collagen binding domain of fibronectin (Sekiguchi et al. ibid., 1980) contains amino acid sequences that bind to the extracellular matrix component collagen.

Particularly preferred tissue-binding domains are the heparin binding domain of fibronectin, comprising the sequence of amino acids of Sequence I.D. No. 2 from alanine, amino acid number 1812 to valine, amino acid number 2171; the collagen binding domain of fibronectin, comprising the sequence of amino acids of Sequence I.D. No. 2 from glycine, amino acid number 282 to serine, amino acid number 608; and the amino terminal 229 amino acids of thrombospondin. In this regard, a particularly preferred tissue-binding domain is the cell-binding domain of fibronectin, comprising the sequence of amino acids of Sequence I.D. No. 2 from alanine, amino acid number 1357 to glutamic acid, amino acid number 1903. It will be evident to one skilled in the art that smaller portions of the cell-binding domain of fibronectin may be used within the hybrid proteins of the present invention, more particularly the sequence of amino acids of Sequence I.D. No. 2 from isoleucine, number 1532 through threonine, amino acid number 1631. As noted above, it is generally accepted that the sequence Gly-Arg-Gly-Asp-Ser (Amino acids 1614 to 1618 of Sequence I.D. No. 2) is central to cell recognition by fibronectin.

Cross-linking domains suitable for use in the hybrid proteins of the present invention are protein domains which contain amino acid sequences required for the formation of specific covalent bonds between peptide chains. In a preferred embodiment the inter-chain cross-links are covalent bonds formed by the action of a transglutaminase such as factor XIII, tissue transglutaminase, prostate transglutaminase, keratinocyte transglutaminase, epidermal transglutaminase or placental transglutaminase. Transglutaminases catalyze the formation of $\epsilon$-($\gamma$-glutamyl)lysine bonds between specific glutamine and lysine residues. However, other inter-chain cross-links, such as those formed by disulfide bonds, are also suitable cross-links. Suitable cross-linking domains include domains from the fibrinogen $\alpha$ chain, the glutamine/lysine rich domains of loricrin that are involved in isodipeptide cross-link formation (Hohl et al., *J. Biol. Chem.* 266: 6626–6636, 1991), and at least one of the 10 amino acid-long repeats of involucrin (*Cell* 46: 583–589, 1986 and Etoh et al., *Biochem. Biophys. Res. Comm.* 136: 51–56, 1986). Preferred cross-linking domains are the carboxy-terminal 103 amino acids of loricrin (Hohl et al., ibid.) and the ten-amino acid repeat beginning with glutamine, amino acid number 496 of involucrin (Simon et al. *J. Biol. Chem.* 263: 18093–18098, 1988). A particularly preferred cross-linking domain comprises the 400 amino-terminal amino acids of the fibrinogen $\alpha$ chain (Doolittle et al., *Nature* 280: 464–468, 1979; Rixon et al., *Biochemistry* 22: 3250–3256, 1983). More particularly, the amino acid sequence of Sequence ID No. 6 from Glycine, amino acid number 928 to Proline, amino acid number 1336 is preferred.

Although the hybrid proteins of the present invention may consist essentially of covalently linked cross-linking and tissue binding domains, they may further contain domains that facilitate end-to-end covalent cross-linking. The $\gamma$ chain of fibrinogen contains a domain that facilitates end-to-end cross-linking to another $\gamma$ chain via $\epsilon$-($\gamma$-glutamyl)lysine bonds. This domain includes at least the 19 carboxy-terminal amino acids and more preferably includes the amino-terminal 275 amino acids of the fibrinogen $\gamma$ chain. The $\alpha$ chain of fibrinogen contains an amino-terminal domain that is involved in interchain disulfide bond formation between $\alpha$ chains. This domain includes the amino-terminal portion of the $\alpha$ chain of fibrinogen from glycine, amino acid 36 to glycine, amino acid 67 of Sequence ID Number 4.

As will be evident to one skilled in the art, the hybrid proteins of the present invention may contain domains of human and other animal proteins. Proteins containing domains suitable for use in the present invention from human and other animals and the DNA molecules encoding such proteins have been reported. Involucrin, loricrin, fibrinogen and fibronectin, for example, have been studied in a variety of animals. DNA sequences encoding primate, canine and porcine involucrin have been reported (Djian and Green, *Mol. Biol. Evol.* 9: 417–432, 1992; Djian and Green, *Proc. Natl. Acad. Sci. USA* 88: 5321–5325, 1991 and Tseng and Green, *Mol. Biol. Evol.* 7: 293–302, 1990). Mehrel et al. (*Cell* 61: 1103–1112, 1990) have reported a DNA sequence encoding mouse loricrin. DNA sequences encoding rat and frog fibrinogen gamma chain have been reported (Haidaris and Courtney, *Blood* 79: 1218–1224, 1992 and Bhattacharya et al., *Mol. Cell. Endocrinol.* 72: 213–220, 1990; respectively). DNA sequences encoding chicken and lamprey fibrinogen $\alpha$ chains have been reported by Weissbach and Greininger (*Proc. Natl. Acad. Sci. USA* 87: 5198–5202, 1990) and Pan and Doolittle (*Proc. Natl. Acad. Sci. USA* 89: 2066–2070, 1992), respectively. DNA sequences encoding bovine and rat fibronectin have been reported by Petersen et al. (*Proc. Natl. Acad. Sci. USA* 80: 137–141, 1983) and Schwarzbauer et al., (*Cell* 35: 421–431, 1983). In general, it is preferred to prepare proteins that contain component domains from a single species to minimize the possibility of immunogenicity. Thus, the present invention provides hybrid proteins that can be used in human and veterinary medicine.

According to the present invention hybrid proteins having cross-linking and tissue adhesive activities are produced recombinantly from host cells transformed with a DNA construct comprising a DNA segment encoding a cross-linking domain from a first protein joined to a DNA segment encoding a tissue-binding domain from a second protein. As used within the context of the present invention, two or more DNA coding sequences are said to be joined when, as a result of in-frame fusions between the DNA coding sequences or as a result of the removal of intervening sequences by normal cellular processing, the DNA coding sequences can be translated into a polypeptide fusion. Unless otherwise noted, the DNA segments may be joined in any order to result in a DNA coding sequence that can be translated into a polypeptide chain. Thus, the DNA segment encoding the tissue-binding domain may be joined to the 5' or the 3' end of the DNA segment encoding the cross-linking domain. However, as will be evident to one skilled in the art, the production of hybrid proteins that additionally include domains that facilitate end-to-end cross-linking will require that the DNA segments encoding such domains be positioned at the 5' and 3' termini of the molecules.

Thus the present invention also provides isolated DNA molecules encoding hybrid proteins comprising a cross-linking domain from a first protein covalently linked to a tissue-binding domain from a second protein. In general, cDNA sequences are preferred for carrying out the present invention due to their lack of intervening sequences which can lead to aberrant RNA processing and reduced expression levels. DNA molecules encoding human fibronectin (Dufour et al., *Exper. Cell Res.* 193: 331–338, 1991) and a human fibrinogen α chain (Rixon et al., *Biochemistry* 22: 3250–3256, 1983) may be obtained from libraries prepared from liver cells according to standard laboratory procedures. It will be understood however, that suitable DNA sequences can also be obtained from genomic clones or can be synthesized de novo according to conventional procedures. If partial clones are obtained, it is necessary to join them in proper reading frame to produce a full length clone, using such techniques as endonuclease cleavage, ligation, and loop-out mutagenesis.

DNA sequences encoding hybrid proteins of the present invention may be prepared from cloned DNAs using conventional procedures of endonuclease cleavage, exonuclease digestion, ligation and in vitro mutagenesis. Alternatively, DNA sequences encoding the cross-linking and tissue-binding domains, such as those mentioned above, may be synthesized using standard laboratory techniques.

An exemplary DNA molecule encoding a hybrid protein having cross-linking and tissue-binding activities may be prepared by joining a DNA segment encoding at least the cell-binding domain of fibronectin and a DNA segment encoding at least an inter-chain cross-linking domain of fibrinogen at a convenient restriction site using synthetic adapters to facilitate in-frame joining of the DNA segments. Alternatively, such DNA segments encoding hybrid proteins of the present invention may be prepared by joining the two domains at a convenient restriction site followed by loop-out mutagenesis to precisely remove unnecessary sequences and directly join the DNA segment encoding the cell-binding domain of fibronectin with the DNA segment encoding the cross-linking domain of fibrinogen.

DNA segments encoding the hybrid proteins of the instant invention are inserted into DNA constructs. As used within the context of the present invention, a DNA construct is understood to refer to a DNA molecule, or a clone of such a molecule, either single- or double-stranded, which has been modified through human intervention to contain segments of DNA combined and juxtaposed in a manner that would not otherwise exist in nature. DNA constructs of the present invention comprise a first DNA segment encoding a hybrid protein operably linked to additional DNA segments required for the expression of the first DNA segment. Within the context of the present invention, additional DNA segments will generally include promoters and transcription terminators, and may further include enhancers and other elements.

DNA constructs may also contain DNA segments necessary to direct the secretion of a polypeptide or protein of interest. Such DNA segments may include at least one secretory signal sequence. Secretory signal sequences, also called leader sequences, prepro sequences and/or pre sequences, are amino acid sequences that act to direct the secretion of mature polypeptides or proteins from a cell. Such sequences are characterized by a core of hydrophobic amino acids and are typically (but not exclusively) found at the amino termini of newly synthesized proteins. DNA segments encoding secretory signal sequences are placed in-frame and in the correct spatial relationship to the DNA segment encoding the protein of interest in order to direct the secretion of the protein. Very often the secretory peptide is cleaved from the mature protein during secretion. Such secretory peptides contain processing sites that allow cleavage of the secretory peptides from the mature proteins as they pass through the secretory pathway. A preferred processing site is a dibasic cleavage site, such as that recognized by the *Saccharomyces cerevisiae* KEX2 gene. A particularly preferred processing site is a Lys-Arg processing site. Processing sites may be encoded within the secretory peptide or may be added to the peptide by, for example, in vitro mutagenesis.

Preferred secretory signals include the α factor signal sequence (pre-pro sequence: Kurjan and Herskowitz, *Cell* 30: 933–943, 1982; Kurjan et al., U.S. Pat. No. 4,546,082; Brake, U.S. Pat. No. 4,870,008), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlsen et al., *Molecular and Cellular Biology* 3: 439–447, 1983). Alternately, a secretory signal sequence may be synthesized according to the rules established, for example, by von Heinje (*European Journal of Biochemistry* 133: 17–21, 1983; *Journal of Molecular Biology* 184: 99–105, 1985; *Nucleic Acids Research* 14: 4683–4690, 1986).

Secretory signal sequences may be used singly or may be combined. For example, a DNA segment encoding a first secretory signal sequence may be used in combination with a DNA segment encoding the third domain of barrier (described in U.S. Pat. No. 5,037,243, which is incorporated by reference herein in its entirety). The DNA segment encoding the third domain of barrier may be positioned in proper reading frame 3' of the DNA segment of interest or 5' to the DNA segment and in proper reading frame with both the DNA segment encoding the secretory signal sequence and the DNA segment of interest.

The choice of suitable promoters, terminators and secretory signals is well within the level of ordinary skill in the art. Methods for expressing cloned genes in *Saccharomyces cerevisiae* are generally known in the art (see, "Gene Expression Technology," *Methods in Enzymology*, Vol. 185, Goeddel (ed.), Academic Press, San Diego, Calif., 1990 and "Guide to Yeast Genetics and Molecular Biology," *Methods in Enzymology*, Guthrie and Fink (eds.), Academic Press, San Diego, Calif., 1991; which are incorporated herein by reference). Transformation systems for other yeasts, including *Hansenula polymorphic, Schizosaccharomyces pombe, Kluyveromyces lactis, Kluyveromyces fragilis, Ustilago maydis, Pichia pastoris, Pichia quillermondil* and *Candida maltosa* are known in the art. See, for example, Gleeson et al., *J. Gen. Microbiol.* 132: 3459–3465, 1986 and Cregg, U.S. Pat. No. 4,882,279.

Proteins of the present invention can also be expressed in filamentous fungi, for example, strains of the fungi Aspergillus (McKnight et al., U.S. Pat. No. 4,935,349, which is incorporated herein by reference) Methods for transforming *Acremonium chrysogenum* are disclosed by Sumino et al., U.S. Pat. No. 5,162,228, which is incorporated herein by reference.

Other higher eukaryotic cells may also be used as hosts, including insect cells, plant cells and avian cells. Transformation of insect cells and production of foreign proteins therein is disclosed by Guarino et al., U.S. Pat. No. 5,162,222 and Bang et al., U.S. Pat. No. 4,775,624, which are incorporated herein by reference. The use of *Agrobacterium rhizogenes* as a vector for expressing genes in plant cells has been reviewed by Sinkar et al., *J. Biosci. (Bangalore)* 11: 47–58, 1987.

Expression of cloned genes in cultured mammalian cells and in *E. coli*, for example, is discussed in detail in Sambrook et al. (*Molecular Cloning: A Laboratory Manual*, Second Edition, Cold Spring Harbor, N.Y., 1989; which is incorporated herein by reference). In addition to *E. coli*, Bacillus and other genera are useful prokaryotic hosts for expressing foreign proteins. As would be evident to one skilled in the art, one could express the proteins of the instant invention in other host cells such as avian, insect and plant cells using regulatory sequences, vectors and methods well established in the literature.

In yeast, suitable vectors for use in the present invention include YRp7 (Struhl et al., *Proc. Natl. Acad. Sci. USA* 76: 1035–1039, 1978), YEp13 (Broach et al., Gene 8: 121–133, 1979), POT vectors (Kawasaki et al, U.S. Pat. No. 4,931,373, which is incorporated by reference herein), pJDB249 and pJDB219 (Beggs, *Nature* 275: 104–108, 1978) and derivatives thereof. Preferred promoters for use in yeast include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, N.Y., 1982; Ammerer, *Meth. Enzymol.* 101: 192–201, 1983). In this regard, particularly preferred promoters are the TPI1 promoter (Kawasaki, U.S. Pat. No. 4,599,311, 1986) and the ADH2-4$^c$ promoter (Russell et al., *Nature* 304: 652–654, 1983; Irani and Kilgore, U.S. patent application Ser. No. 07/631,763, Calif. 1,304,020 and EP 284 044, which are incorporated herein by reference). The expression units may also include a transcriptional terminator. A preferred transcriptional terminator is the TPI1 terminator (Alber and Kawasaki, ibid.).

Host cells containing DNA constructs of the present invention are then cultured to produce the hybrid proteins. The cells are cultured according to standard methods in a culture medium containing nutrients required for growth of the particular host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by a selectable marker on the DNA construct or co-transfected with the DNA construct.

Selection of a medium appropriate for the particular host cell used is within the level of ordinary skill in the art. Yeast cells, for example, are preferably cultured in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide or ammonium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1M and 1.5M, preferably at 0.5M or 1.0M. Cultured mammalian cells are generally cultured in commercially available serum-containing or serum-free media.

The recombinant hybrid proteins expressed using the methods described herein are isolated and purified by conventional procedures, including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like. Methods of protein purification are known in the art (see generally, Scopes, R., *Protein Purification*, Springer-Verlag, N.Y. (1982), which is incorporated herein by reference) and may be applied to the purification of the recombinant proteins of the present invention.

The hybrid proteins of the present invention may be used as components of tissue adhesives. It is preferred that the tissue adhesives be formulated to provide a concentration of the hybrid proteins of the present invention of between about 5 mg/ml to 100 mg/ml, with concentrations in the range of 35 to 50 mg/ml being particularly preferred. As disclosed above, tissue adhesives generally contain factor XIII and thrombin. Additional components may also be included in the tissue adhesive formulations. These additional components include growth factors such as PDGF, bFGF, TGFa, or EGF and protease inhibitors, such as aprotinin, transexamic acid, alpha-2 plasmin inhibitor, alpha-1-antitrypsin or the Pittsburgh mutant of alpha-1-antitrypsin (Arg-358 alpha-1-antitrypsin). The tissue adhesives may also contain salts, buffering agents, reducing agents, bulking agents, and solubility enhancers. Albumin, NaCl, $CaCl_2$, citrate and phosphate buffers, for example, may be included. Preferably, the tissue adhesives of the present invention are prepared as lyophilized powders, liquid concentrates of ready-to-use liquids. Lyophilized powders are preferred for ease of handling and storage.

The following examples are offered by way of illustration and not by way of limitation.

EXAMPLES

Example 1
Subcloning and Modification of ADH2 Promoters

An ADH2-4$^c$ promoter was constructed as described in co-pending U.S. patent application Ser. No. 07/631,763, Calif. 1,304,020 and EP 284 044, which are incorporated herein by reference. A DNA construct comprising the complete ADH2-4$^c$ promoter mutagenized at the 3' end to place an Eco RI site in place of the translation start codon, designated p410-4$^c$ (deposited with the American Type Culture Collection (12301 Parklawn Dr., Rockville, Md. 20852) under accession number 68861) was used as the source of the ADH2-4$^c$ promoter.

A PAP-I cDNA (U.S. Pat. No. 4,937,324) was joined with the ADH2-4$^c$ promoter. Plasmid pAP1.7, comprising the 1.7 kb cDNA in pUC18, was cut with Nco I and Bam HI, and the linearized plasmid was isolated through two rounds of gel purification. The ADH2-4$^c$ promoter from p410-4$^c$ was joined to the 5' end of the PAP-I cDNA via an Eco RI-Nco I adapter. The 1.2 kb Bam HI-Eco RI promoter fragment from p410–4$^c$, Eco RI-Nco I adapter and the Nco I-Bam HI linearized pAP1.7 plasmid were ligated. The resultant plasmid was designed pPR1. The presence of the correct promoter fusion was confirmed by DNA sequencing.

A yeast expression vector comprising the ADH2-4$^c$ promoter, the PAP-I cDNA and the TPI1 terminator was constructed. Plasmid pZUC13 (comprising the *S. cerevisiae* chromosomal LEU2 gene and the origin of replication from *S. cerevisiae* 2 micron plasmid inserted into pUC13 and constructed in a manner analogous to pZUC12, described in published EP 195,691, using the plasmid pMT212, which is described in published EP 163 529) was cut with Bam HI. Plasmid pPR1 was digested completely digested with Bam HI and partially digested with Sac I to isolate the 2.1 kb ADH2-4$^c$ promoter-PAP-I cDNA fragment. Plasmid pTT1 (described in detail below) was digested with Sac I and Bam HI to isolate the 0.69 bp TPI1 terminator fragment. The Bam HI-Sac I fragment from pPR1 and the Sac I-Bam HI fragment from pTT1 were ligated with the Bam HI-linearized pZUC13. A plasmid containing the expression unit was designated pZ3.

Example 2
Subcloning of the TPI1 terminator

The yeast TPI1 terminator fragment was obtained from plasmid p270 described by Murray and Kelly (U.S. Pat. 4,766,073, which is incorporated by reference herein in its entirety). Plasmid p270 contains the TPI1 terminator inserted as and Xba I-Bam HI fragment into YEp13. Alternatively, the TPI1 terminator may be obtained from plasmid pM220 (deposited with American Type Culture Collection as an *E. coli* RR1 transformant under accession number 39853) by digesting the plasmid with Xba I, and Bam HI and purifying the TPI1 terminator fragment (~700 bp).

The TPI1 terminator was removed from plasmid p270 as a Xba I-Bam HI fragment. This fragment was cloned into pUC19 along with another fragment containing the TPI1 promoter fused to the CAT (chloramphenicol acetyl transferase) gene to obtain a TPI1 terminator fragment with an Eco RV end. The resultant plasmid was designated pCAT. The TPI1 terminator was then cut from pCAT as an Eco RV-Bam HI fragment and cloned into pIC19H (Marsh et al., *Gene* 32: 481–486, 1984) which had been cut with the same enzymes, to obtain pTT1 (disclosed in U.S. Pat. No. 4,937,324, which is incorporated herein by reference).

Example 3
Construction of Yeast Vectors pDPOT and pRPOT

Plasmid pDPOT was derived from plasmid pCPOT (ATCC No. 39685) by replacing the 750 bp Sph I-Bam HI fragment of pCPOT containing 2 micron and pBR322 sequences with a 186 bp Sph I-Bam HI fragment derived from the pBR322 tetracycline resistance gene.

Plasmid pRPOT was derived from plasmid pDPOT by replacing the Sph I-Bam HI fragment with a polylinker. Plasmid pDPOT was digested with Sph I and Bam HI to isolate the 10.8 kb fragment. Oligonucleotides ZC1551 and ZC1552 (Sequence ID Nos. 7 and 8) were designed to form an adapter with a Bam HI adhesive end and an Sph I adhesive end flanking Sma I, Sst I and Xho I restriction sites. Oligonucleotides ZC1551 and ZC1552 (Sequence ID Nos. 7 and 8) were kinased and annealed to form the Bam HI-Sph I adapter. The 10.8 kb pDPOT fragment was circularized by ligation with the ZC1551/ZC1552 adapter (Sequence ID Nos. 7 and 8). The resultant plasmid was termed pRPOT.

Example 4
Construction of a Fibrinogen:Fibronectin Hybrid cDNA Expression Vector A. Construction of pFN14A A DNA construct containing a DNA segment encoding the fibronectin cell-binding domain operably linked to the ADH2-4$^c$ promoter in plasmid pUC19 was constructed. The fibronectin coding sequence was obtained from plasmid pFH103 (Dufour et al., *Exper. Cell Res.* 193: 331–338, 1991). Plasmid pFH103 was digested with Nco I and Xba I to isolate the 4 kb fragment containing the fibronectin coding sequence. Oligonucleotides ZC2052 and ZC2053 (Sequence ID Nos. 9 and 10) were designed to provide, upon annealing, an adapter containing a 5' Eco RI adhesive end, an internal Nco I site, a DNA segment encoding a methionine and amino acids 979 through 981 of Sequence ID Number 2 and a 3' Nco I adhesive end that destroys the Nco I site. Oligonucleotides ZC2052 and ZC2053 (Sequence ID Nos. 9 and 10) were annealed and ligated with the 4 kb Nco I-Xba I fibronectin fragment into Eco RI-Xba I linearized pUC19. The resultant plasmid was designated pFN4.

Plasmid pFN4 was digested with Hind III and Apa I to isolate the 3.3 kb fibronectin fragment. Oligonucleotides ZC2493 and ZC2491 (Sequence ID Nos. 12 and 11) were designed to provide, when annealed, an Apa I-Xba I adapter encoding the amino acids Pro and Phe followed by a stop codon. The oligonucleotides were annealed and combined with the 3.3 kb Hind III-Apa I fragment and Hind III-Xba I linearized pUC19 to form plasmid pFN7. Plasmid pFN7 comprises a DNA segment encoding amino acids 1273–2186 of Sequence ID Number 2 followed by an in-frame stop codon.

The ADH2-4$^c$ promoter was joined to the 5' end of the fibronectin cDNA in plasmid pFN5. Plasmid pFN4 was digested with Nco I and Hind III to isolate the 0.89 kb fibronectin coding sequence. Plasmid pZ3 (described in detail above) was digested with Bam HI and Nco I to isolate the 1.25 kb ADH2-4$^c$ promoter fragment. The 1.25 kb Bam HI-Nco I promoter fragment and the Nco I-Hind III fibronectin coding sequence fragment were ligated to Bam HI-Hind III linearized pUC19 to form plasmid pFN5.

Plasmid pFN5 was digested with Bam HI and Hind III to isolate the 2.1 kb promoter-fibronectin fragment. Plasmid pFN7 was digested with Hind III and Xba I to isolate the 2.8 kb fibronectin fragment that was modified to encode a stop codon following the Pro-Phe sequence. The TPI1 terminator sequence was obtained from pTT1 as a 0.7 kb Xba I-Sal I fragment. The 2.1 kb Bam HI-Hind III promoter-fibronectin fragment, the 2.8 kb Hind III-Xba I fibronectin fragment and the 0.7 kb TPI1 terminator fragment were joined in a four-part ligation with Bam HI-Xho I linearized pRPOT. A plasmid containing the fibronectin expression unit in the pRPOT vector was designated pR1.

The original clone pFH103 contained a frame-shift mutation in the EIIIB region of the fibronectin cDNA. The mutation was corrected by the replacement of the region with an analogous region from the plasmid pFHΔ3 (obtained from Jean Paul Thiery, Laboratoire de Physiopathologie du Developpement, CNRS URA 1337, Ecole Normale Superiure, 46 rue d'Ulm, 75230 Paris Cedex 05, France). Plasmid pFHΔ3 was derived from pFH103 by excising the 3211 bp Xba I-Asp 718I fragment of fibronectin, blunting of the resultant adhesive ends and religating. Plasmid pFHΔ3 contains a DNA segment encoding the signal and propeptides, the first three and one half type I repeats, and the carboxy-terminal half of human fibronectin from the middle of the EIIIB segment.

Plasmid pR1 was digested with Bam HI and Kpn I to isolate the 2.2 kb promoter-fibronectin fragment. Plasmid pFHΔ3 was digested with Kpn I and Apa I to isolate the internal fibronectin fragment that corrects the frame-shift mutation present in the parent cDNA from pFH103. Plasmid pR1 was digested with Apa I and Bam HI to isolate the TPI1 terminator fragment. The 2.2 kb Bam HI-Kpn I promoter-fibronectin fragment, the 2.75 kb Kpn I-Apa I internal fibronectin fragment and the 0.69 kb Apa I-Bam HI TPI1 terminator fragment were joined in a four-part ligation with Bam HI-linearized pDPOT. The resulting construction was designated pD32.

A DNA segment encoding the ADH2-4$^c$ promoter and initiation methionine from plasmid pD32 was subcloned into pIC19H (Marsh et al., Gene 32: 481–486, 1984) as a 1.25 kb Bam HI-Nco I fragment. Plasmid pD32 was also digested with Nco I and Bgl II to isolate the 3 kb fibronectin cDNA fragment encoding amino acids 979–1972 of Sequence ID Number 2. The 1.25 kb Bam HI-Nco I fragment and the Nco I-Bgl II fragment were ligated with Bam HI-linearized pIC19H. A plasmid containing a Bam HI site proximal to the ADH2-4$^c$ promoter was designated pFN14A.

B. Construction of Plasmid pD38

An expression vector comprising a DNA segment encoding a fibronectin-fibrinogen hybrid protein operably linked to the ADH2-4$^c$ promoter and the TPI1 terminator was constructed. To assemble the DNA sequence encoding the hybrid protein, a DNA segment encoding approximately the carboxy-terminal 409 amino acids of the α chain of fibrinogen was first subcloned.

A fibrinogen α chain cDNA was obtained from Dominic W. Chung (Department of Biochemistry, University of Washington, Seattle, Wash.) in plasmid pHIα3 (Rixon et al., Biochemistry 22: 3250–3256, 1983). Sequence analysis of the cDNA insert in plasmid pHIα-3 revealed a deletion of codons 1348–1350 of the published sequence resulting in the deletion of Serine, amino acid 417.

The DNA segment encoding the carboxy-terminus of the fibrinogen a chain was subcloned into plasmid pUC19. Plasmid pHIα-3 was digested with Asp 718 and Ssp I to isolate the approximately 2 kb fragment encoding the carboxy-terminus of the fibrinogen a chain from amino acid 244 to amino acid 643 and some 3' untranslated sequence of Sequence ID Number 4. Plasmid pTT1 was digested with Eco RV and Sal I to isolate the approximately 700 bp TPI1 terminator fragment. The 2 kb fibrinogen α chain sequence and the TPI1 terminator sequence were ligated with pUC19 that had been linearized with Asp 718 and Sal I. The ligation mixture was transformed into E. coli, and plasmid DNA was prepared and analyzed by restriction endonuclease and DNA sequence analysis. DNA sequence analysis of a candidate clone revealed that the Sal I site joining the TPI1 terminator sequence and the pUC19 polylinker site was not present. Plasmid DNA from the candidate clone was digested with Asp 718 and Bam HI to liberate the approximately 1.9 kb fibrinogen-TPI1 terminator fragment.

To join the fibronectin coding sequence with the fibrinogen α chain sequence, synthetic oligonucleotides were synthesized to provide, when annealed, a Sal I-Asp 718 adapter encoding an internal Afl II restriction site, and a sequence encoding amino acids 1886 through 1903 of fibronectin (Sequence ID Number 2), a glycine residue and amino acids 235 through 243 of the fibrinogen a chain (Sequence ID Number 4). Oligonucleotides ZC3521 and ZC3522 (Sequence ID Nos. 13 and 14) were annealed. The 1.9 kb Asp 718-Bam HI fibrinogen-TPI1 terminator fragment and the Sal I-Asp 718 ZC3521/ZC3522 adapter (Sequence ID Nos. 13 and 14) were ligated with pUC19 that had been linearized with Sal I and Bam HI. The resultant plasmid was designated pFG4.

The DNA segment encoding the fibronectin-fibrinogen α chain sequence in plasmid pFG4 was joined with the DNA segment encoding the amino-terminal fibronectin sequence (from amino acid 989 to amino acid 1885 of Sequence ID Number 2) in plasmid pFN14A to construct plasmid pD37. Plasmid pFN14A was digested with Bgl II and Afl II to isolate the approximately 3.9 kb ADH2-4$^c$ promoter-fibronectin fragment. Plasmid pFG4 was digested with Afl II and Bam HI to isolate the approximately 2 kb fibronectin-fibrinogen-TPI1 terminator fragment. The 3.9 kb Bgl II-Afl II fragment and the 2 kb Afl II-Bam HI fragment were ligated with Bam HI-linearized pDPOT. A plasmid with the expression unit inserted with the direction of transcription in the same direction as the POT1 gene in the pDPOT vector was designated pD37.

To place the expression unit present in pD37 in the opposite orientation, such that the direction of transcription of the expression unit was in the opposite direction to that of the POT1 gene, plasmid pD37 was digested with Nco I and Xba I to isolate the approximately 4 kb fibronectin-fibrinogen α chain fragment. Plasmid pFN14A was digested with Bam HI and Nco I to isolate the approximately 1.3 kb ADH2-4$^c$ promoter fragment. Plasmid pTT1 was digested with Bam HI and Xba I to isolate the approximately 700 bp TPI1 terminator fragment. The Bam HI-Nco I ADH2-4$^c$ promoter fragment, the Nco I-Xba I fibronectin-fibrinogen α chain fragment and the Xba I-Bam HI TPI1 terminator fragment were ligated with Bam HI-linearized pDPOT that had been treated with calf alkaline phosphatase to prevent recircularization. A plasmid containing the expression unit in the opposite orientation relative to the POT1 gene was designated pD38. The nucleotide sequence and deduced amino acid sequence of the DNA segment encoding the fibronectin-fibrinogen hybrid of plasmid pD38 is shown in Sequence ID Number 5. Plasmid pD38 was deposited on Dec. 15, 1992 with the American Type Culture Collection (12301 Parklawn Drive, Rockville, Md.) as an E. coli transformant under accession Number 69164.

Example 5

Expression of a Fibronectin-Fibrinogen Hybrid Protein in Yeast

Plasmid pD38 was transformed into the Saccharomyces cerevisiae host strain ZM118 (MATa/MATα ura3/ura3

Δtpil::URA3/Δtpil::URA3 leu2-3,112/leu2-3,112 bar1/bar1 pep4:: URA3/pep4::URA3 [cir°]) using essentially the method described by Hinnen et al. (*Proc. Natl. Acad. Sci. USA* 75: 1929–1933, 1978). Transformants were selected for their ability to grow on medium containing glucose as the sole carbon source.

The ZM118[pD38] transformant was scaled up in a 60 liter fermenter to facilitate purification of the hybrid protein. A single ZM118[pD38] colony was selected from a YEPD+Ade+Leu plate (Table 1) and inoculated into -LeuTrpThrD medium (Table 1). The culture was incubated for approximately 52 hours after which the cells were harvested. The cells were washed in T. E. buffer (Sambrook et al., ibid.), resuspended in T. E. buffer+30% glycerol, and aliquotted into 1 ml seed vials. The seed vials were stored at −80° C. One seed vial was used to inoculate 100 ml of YEPD+Ade+Leu (Table 1). The culture was grown for approximately 28 hours to a final $A_{660}$ of 7.7. The 100 ml culture of ZM118 [pD38] was inoculated into a 10 liter fermenter with a final volume of 6.0 liters of medium containing 10 g/L $(NH_4)_2SO_4$, 5 g/L $KH_2PO_4$, 5 g/L $MgSO_4 \cdot 7H_2O$, 1 g/L NaCl, 0.5 g/L $CaCl_2 \cdot 2H_2O$, 3.68 g/L A.A.I. (Table 1), 4.2 g/L citric acid, 60 g/L glucose, 10 ml/L Trace Metal Solution (Table 1), 0.4 ml/L PPG-2025 (Polypropylene glycol, MW 2025, Union Carbide Corp, Danbury, Conn.) that had been pH adjusted to pH 5.0 with NaOH. In addition to the inoculation culture, 30 ml of Vitamin solution was added (Table 1). The culture was grown for 23 hours at 30° C. with the addition of 2M NaOH to maintain pH of approximately 5.

TABLE 1

Media Recipes

—LeuThrTrp Amino Acid Mixture 4 g adenine
3 g L-arginine
5 g L-aspartic acid
2 g L-histidine free base
6 g L-isoleucine
4 g L-lysine-mono hydrochloride
2 g L-methionine
6 g L-phenylalanine
5 g L-serine
5 g L-tyrosine
4 g uracil
6 g L-valine
Mix all the ingredients and grind with a mortar and pestle until the mixture is finely ground.

—LeuTrpThrD 20 g glucose
6.7 g Yeast Nitrogen Base without amino acids (DIFCO Laboratories, Detroit, MI)
0.6 g —LeuThrTrp Amino Acid Mixture
18 g Agar
Mix all the ingredients in distilled water. Add distilled water to a final volume of 1 liter. Autoclave 15 minutes. Pour plates and allow to solidify.

YEPD + Ade + Leu Plates 20 g glucose
20 g Bacto Peptone (DIFCO Laboratories)
10 g Bacto Yeast Extract (DIFCO Laboratories)
18 g agar
4 ml 1% adenine
8 ml 1% L-leucine TABLE 1-continued Media Recipes Mix all ingredients in distilled water, and bring to a final volume of 1 liter. Autoclave 25 minutes and pour plates.

YEPD + Ade + Leu Medium 20 g glucose
20 g Bacto Peptone (DIFCO Laboratories)
10 g Bacto Yeast Extract (DIFCO Laboratories)
4 ml 1% adenine
8 ml 1% L-leucine
Mix all ingredients in distilled water, and bring to a final volume of 1 liter. Autoclave 25 minutes.

A. A. I.

4.0 g adenine
5.0 g L-alanine
2.0 g L-arginine
5.0 g L-asparagine
5.0 g L-aspartic acid
5.0 g L-cysteine
5.0 g L-glutamine
5.0 g L-glutamic acid
5.0 g L-glycine
8.0 g L-histidine
5.0 g L-isoleucine
3.0 g L-lysine-mono hydrochloride
2.0 g L-methionine
5.0 g L-phenylalanine
5.0 g L-proline
5.0 g L-serine
5.0 g L-threonine
2.0 g L-tryptophan
3.0 g L-tyrosine
3.0 g uracil
5.0 g L-valine
Mix all the ingredients and grind with a mortar and pestle until the mixture is finely ground. Store at room temperature.

Trace Metal Solution 0.68 g $ZnCl_2$
5.4 g $FeCl_3 \cdot 6H_2O$
1.91 g $MnCl_2 \cdot 4H_2O$
0.22 g $CuSO_4 \cdot 5H_2O$
0.258 g $CoCl_2$
0.062 g $H_3BO_3$
0.002 g $(NH_4)_6Mo_2O_2$
0.002 g KI
10.0 ml 37% HCl
Dissolve solids in water and bring to a final volume of 1 liter.

Vitamin Solution 25 mg d-biotin
400 mg thiamine
400 mg pyridoxine
7.5 g meso-inositol
7.5 g Ca pantothenate
300 mg niacinamide
50 mg folic acid
100 mg riboflavin
500 mg choline
Dissolve solids in water and bring to a final volume of 1 liter.

A 60 liter fermenter with a final volume of 50 liters of medium containing 60 g/L yeast extract (Universal Foods, Milwaukee, Wis.), 2.5 g/L $MgSO_4 \cdot 7H_2O$ (Mallinkrodt Inc., St. Louis, Mo.), 1 g/L $CaCl_2 \cdot 2H_2O$ (Mallinkrodt, Inc.), 1 g/L KCl (Mallinkrodt, Inc.), 10 ml/L of Trace Metal Solution (Table 1), 0.5 ml/L PPG-2025 (Union Carbide) that had been adjusted to a pH of 5.0 with $H_3PO_4$ was prepared, and the medium was sterilized. After sterilization, 5.0 liters of the 23 hour fermentation culture and 500 ml of Vitamin Solution (Table 1) were inoculated into the medium. During the fermentation, a solution of 50% glucose, 5% $(NH_4)_2SO_4$, 0.05% citric acid was fed into the fermenter at a rate of 150 ml/hour, and the pH was maintained at approximately pH 5 by the addition of 2M $NH_4OH$. PPG-2025 was added as needed to control foaming. At approximately 49 hours post inoculation, an ethanol feed was begun by the addition of ethanol to the fermenter at a rate of 150 ml/min. The culture was grown for a total of 67.25 hours at 30° C.

At the end of the fermentation, 50 liters of the culture was diluted to 100 liters with water. The cells were removed from the spent medium by centrifuging 50 liters at a time through a Westfalia CSA 19 centrifuge (Westfalia, Oelde, Germany) at a flow rate of 4 liters/min. The cells were rinsed with water. From the centrifugation, approximately 20 liters of cell slurry containing approximately 35% cells was obtained. Salts were added to the slurry to achieve a final concentration of the following salts: 50 mM NaCl, 10 mM $Na_2HPO_4$, 5 mM EDTA. The cell slurry was passed through a Dynomill bead mill using 0.5 mm lead-free glass beads (Willy A Bachofen AG MashinenFabrik, Basle, Switzerland) at a rate of 4 liters per minute. The Dynomill was rinsed with Lysis buffer (50 mM NaCl, 10 mM $Na_2HPO_4$, 5 mM EDTA, pH 7.2) to a final volume of 80 liters. The final slurry had a pH of 6.8, a temperature of approximately 10° C. and a conductivity of 5 ms/cm.

The cell slurry was subjected to centrifugation as described above, and the cell pellet was rinsed with lysis buffer. After centrifugation approximately 20 liters of cell slurry was obtained. The cell slurry was extracted by first adjusting the concentration of the cell debris to approximately 40–50% with lysis buffer. Solid urea, NaCl and EDTA were added to the cell slurry to achieve a final concentration of approximately 8M urea, 0.3M NaCl and 10 mM EDTA. The approximate salt concentrations were obtained by the addition of 450 g/L of urea, 18 g/L of NaCl and 4.2 g/L of EDTA. The cell slurry was adjusted to pH 7.8 with 0.5M NaOH. The solids were dissolved into the slurry and the pellets were extracted for a total of 50 minutes. Following extraction, the mixture was diluted 1 to 4 with water, adjusted to a conductivity of 12.5 ms/cm with NaCl and adjusted to a pH of 9.5 with 0.5M NaOH.

The extracted slurry was centrifuged as described above with the lysis buffer rinse. The pH of the supernatant was adjusted to pH 9.5 with 0.5M NaOH. The supernatant was analyzed by SDS polyacrylamide gel electrophoresis (SDS-PAGE) using the PHAST System Separation and Control Unit (Pharmacia LKB Biotechnology Inc., Piscataway, N.J.), and the protein was visualized using Coomassie Blue staining. A 2 liter Q-sepharose column (Pharmacia) was equilibrated at 5 liters/hour with successive washes of the following solutions: 8 liters of 3M urea, 1M NaCl, 50 mM glycine, pH 11.5; 5 liters of 0.5M NaOH; 1.5 liters of water; 5 liters of 0.1M HCl; and 6.0 liters of Wash buffer (50 mM glycine, 90 mM NaCl, pH 9.5 with a conductivity of 12.5 ms/cm). The supernatant (110 liters) was then applied to the column at 5 liters per hour.

The column ran dry after loading the supernatant. The gel was resuspended in Wash buffer and repacked. The repacked column was washed with 4 liters of 50 mM glycine, 90 mM NaCl, 5 mM EDTA, pH 10.0. The material was eluted with elution buffer (50 mM glycine, 5 mM EDTA (pH 9.9) with a final concentration of NaCl giving a conductivity of 30.2 cm/ms (approximately 270 mM NaCl)) at 100 ml per minute. The approximately 600 ml fractions were collected after the conductivity of the eluant reached the conductivity of the elution buffer. Fractions were analyzed by SDS-PAGE analysis as described above and fractions 1 through 10 were pooled.

The pooled fractions were then applied to a 2 liter phenyl Sepharose column (Pharmacia) that had been equilibrated by successive washes at 5 liters per hour with the following solutions: 3 liters of 0.5M NaOH; 3 liters of water; 3 liters of 2M urea, 50 mM glycine, pH 10.5; 1.5 liters of water; 3 liters of 0.1M HCl; and 3 liters of Equilibration buffer (50 mM glycine, 2.5M NaCl, 2 mM EDTA (pH 10.0) with a conductivity of 180 ms/cm). The pooled peak fractions, which had been adjusted to a conductivity of 180 ms/cm with NaCl and a pH of 10.0 with 0.5M NaOH, were loaded onto the phenyl sepharose column. Following the loading of the peak fractions, the column was washed with Equilibration buffer. The column was eluted with 6 liters of 50 mM glycine, 2 mM EDTA (pH 10.25) with a NaCl concentration giving the solution a conductivity of 96 ms/cm. The conductivity of the eluant was measured throughout the elution. The conductivity of the eluant upon starting the elution was 180 ms/cm. In the third fraction, the conductivity of the eluant dropped to 96 ms/cm. At this point, the elution buffer was changed to a buffer having the conductivity of 42 ms/cm. The eluant was collected through fraction number 8.

Example 6
Cross-Linking Assay Using the Hybrid Fibrinogen-Fibronectin Protein

The ability of the purified fibrinogen-fibronectin hybrid protein to form transglutminase-catalyzed interchain cross links was assessed. The transglutaminase activity was provided by the addition of recombinant factor XIII and thrombin or by the addition of recombinant factor XIIIa.

A. Preparation of Factor XIII

Recombinant factor XIII was prepared essentially as described in co-pending U.S. patent application Ser. No. 07/927,196, which is incorporated by reference herein in its entirety. Briefly, factor XIII was isolated from a strain of the yeast *Saccharomyces cerevisiae* that had been transformed with an expression vector capable of directing the expression of factor XIII. The factor XIII-producing cells were harvested and lysed, and a cleared lysate was prepared. The lysate was fractionated by anion exchange chromatography at neutral to slightly alkaline pH using a column of derivatized agarose, such as DEAE FAST-FLOW SEPHAROSE (Pharmacia LKB Biotechnology, Piscataway, N.J.) or the like. Factor XIII was then precipitated from the column eluate by concentrating the eluate and adjusting the pH to between 5.2 and 5.5, such as by diafiltration against ammonium succinate buffer. The precipitate was then dissolved and further purified using conventional chromatographic techniques, such as gel filtration and hydrophobic interaction chromatography. The purified factor XIII was dialyzed, filtered, aliquotted and lyophilized. The factor XIIIa content was determined (Bishop et al., *Biochemistry* 29: 1861–1869, 1990, which is incorporated by reference herein in its entirety) by fluorometric assay of the dissolved, thrombin-activated material.

Factor XIII was activated to factor XIIIa by adding 2 U of thrombin per 100 mg of factor XIII. The factor XIII was dissolved in buffer (20 mM sodium borate (pH 8.3), 1 mM $CaCl_2$). The thrombin was added, and the reaction was incubated at room temperature for twenty minutes.

B. Cross-Linking Assays

The level of cross-linking between the hybrid proteins was measured as a rise in the absorbance at 350 nm over time in reaction mixtures containing the hybrid protein, factor XIII and thrombin or the hybrid protein and factor XIIIa. Control reactions were prepared containing factor XIII and thrombin or factor XIIIa alone. Cross-linking reactions were carried out in 1 ml cuvettes. For cross-linking reactions containing factor XIII and thrombin, each reaction mixture was set up by placing 110 μl containing 40 Units of factor XIII, 36.7 μl containing 13 Units of factor XIII or 12.2 μl containing 4 Units of factor XIII (described above) in one corner of the cuvette and 20 μl containing 4 Units of thrombin (Sigma) in the opposite corner such that the solutions were not mixed. The reaction was initiated by the addition of 1 ml of 2 mg/ml hybrid protein in buffer (10 mM Tris (pH 7.6), 20 mM sodium borate, 140 mM NaCl, 10 mM CaCl$_2$). The absorbance of each reaction was read at 350 nm with the addition of protein being the first absorbance point.

For cross-linking reactions containing factor XIIIa, each reaction was set up by placing 110 μl containing 40 Units of factor XIIIa, 36.7 μl containing 13 Units of factor XIIIa or 12.2 μl containing 4 Units of factor XIIIa in the cuvette and adding 1 ml of 2 mg/ml hybrid in buffer (10 mM Tris (pH 7.6), 140 mM NaCl, 10 mM CaCl$_2$). The absorbance of the solution was read at 350 nm as described above. Analysis of the data generated from the absorbance time courses showed a sharp increase in absorbance in the presence of hybrid protein and the active transglutaminase relative to the rise in absorbance in the absence of hybrid protein (FIGS. 2–5). The results indicated that the hybrid protein is capable of transglutaminase-induced cross-linking.

From the foregoing it will be appreciated that, although specific embodiments of the invention have been described herein for the purpose of illustration, various modifications may be made without deviation from the spirit and scope of the invention. Accordingly, the invention is not to be limited except as by the following claims.

---

I claim:

1. A hybrid protein comprising a tissue-binding domain from a first protein selected from the group consisting of human thrombospondin and human fibronectin covalently linked to a cross-linking domain from a second protein selected from the group consisting of human loricrin, human involucrin, and human fibrinogen α chain, wherein said hybrid protein has tissue-binding activity and is cross-linkable.

2. A hybrid protein according to claim 1 wherein the tissue-binding domain of the first protein is a heparin binding domain of thrombospondin, a heparin binding domain of fibronectin, a collagen binding domain of fibronectin or a cell binding domain of fibronectin.

3. A hybrid protein according to claim 1 wherein the tissue-binding domain of the first protein comprises the amino acid sequence of SEQ ID NO. 6 from Alanine, amino acid 2 to Glutamic acid, amino acid number 926.

4. A hybrid protein according to claim 1 wherein the cross-linking domain of the second protein comprises the amino acid sequence of SEQ ID NO. 6 from Glycine, amino acid number 928 to Proline, amino acid number 1336.

5. A hybrid protein according to claim 1 comprising the amino acid sequence of SEQ ID NO. 6 from alanine, amino acid number 2 to Proline, amino acid number 1336.

6. An isolated DNA molecule encoding a hybrid protein comprising a first DNA segment encoding a tissue-binding domain from a first protein selected from the group consisting of human thrombospondin and human fibronectin joined to a second DNA segment encoding a cross-linking domain from a second protein selected from the group consisting of human loricrin, human involucrin, and human fibrinogen α chain, wherein said hybrid protein has tissue-binding activity and is cross-linkable.

7. A DNA molecule according to claim 6 wherein the first DNA segment encodes a heparin binding domain of thrombospondin, a heparin binding domain of fibronectin, a collagen binding domain of fibronectin, a collagen binding domain of fibronectin or a cell binding domain of fibronectin.

8. A DNA molecule according to claim 6 wherein the first DNA segment comprises the nucleotide sequence of SEQ ID NO. 5 from nucleotide 3 to nucleotide 2780.

9. A DNA molecule according to claim 6 wherein the first DNA segment encodes the amino acid sequence of SEQ ID NO. 6 from methionine, amino acid number 1 to glutamic acid, amino acid number 926.

10. A DNA molecule according to claim 6 wherein the second DNA segment comprises the nucleotide sequence of SEQ ID NO. 5 from nucleotide 2784 to nucleotide 4013.

11. A DNA molecule according to claim 6 wherein the second DNA segment encodes the amino acid sequence of SEQ ID NO. 6 from glycine, amino acid number 928 to proline, amino acid number 1336.

12. A DNA molecule according to claim 6 wherein the DNA molecule encodes the amino acid sequence of SEQ ID NO. 6 from Methionine, amino acid number 1 to Proline, amino acid number 1336.

13. A DNA molecule according to claim 6 wherein the DNA molecule comprises the nucleotide sequence of SEQ ID NO. 5 from nucleotide 3 to nucleotide 4013.

14. A DNA construct comprising a DNA molecule encoding a hybrid protein, wherein said DNA molecule comprises a first DNA segment encoding a tissue-binding domain from a first protein selected from the group consisting of human thrombospondin and human fibronectin joined to a second DNA segment encoding a cross-linking domain from a second protein selected from the group consisting of human loricrin, human involucrin, and human fibrinogen α chain, wherein said DNA molecule is operably linked to other DNA segments required for the expression of the DNA molecule, wherein said hybrid protein has tissue-binding activity and is cross-linkable.

15. A DNA construct according to claim 14 wherein the first DNA segment encodes a heparin binding domain of thrombospondin, a heparin binding domain of fibronectin, a collagen binding domain of fibronectin or a cell binding domain of fibronectin.

16. A DNA construct according to claim 14 wherein the first DNA segment comprises the nucleotide sequence of SEQ ID NO. 5 from nucleotide 3 to nucleotide 2780.

17. A DNA construct according to claim 14 wherein the first DNA segment encodes the amino acid sequence of SEQ ID NO. 6 from methionine, amino acid 1 to Glutamic acid, amino acid number 926.

18. A DNA construct according to claim 14 wherein the second DNA segment comprises the nucleotide sequence of SEQ ID NO. 5 from nucleotide 2784 to nucleotide 4013.

19. A DNA construct according to claim 14 wherein the second DNA segment encodes the amino acid sequence of SEQ ID NO. 6 from glycine, amino acid number 928 to proline, amino acid number 1336.

20. A DNA construct according to claim 14 wherein the DNA molecule comprises the nucleotide sequence of SEQ ID NO. 5 from nucleotide 1 to nucleotide 4013.

21. A DNA construct according to claim 14 wherein the DNA molecule encodes the amino acid sequence of SEQ ID NO. 6 from Methionine, amino acid number 1 to Proline, amino acid number 1336.

22. A host cell containing a DNA construct according to claim 16.

23. A method for producing a hybrid protein comprising culturing a host cell according to claim 22 under conditions promoting the expression of the first DNA segment.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 7803 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 6..7346

( x i ) SEQUENCE DESCRIPTION: SEQ ID NO:1:

```
TCAAC ATG CTT AGG GGT CCG GGG CCC GGG CTG CTG CTG CTG GCC GTC         47
      Met Leu Arg Gly Pro Gly Pro Gly Leu Leu Leu Leu Ala Val
      1               5                   10

CTG TGC CTG GGG ACA GCG GTG CCC TCC ACG GGA GCC TCG AAG AGC AAG       95
Leu Cys Leu Gly Thr Ala Val Pro Ser Thr Gly Ala Ser Lys Ser Lys
15                  20                  25                  30

AGG CAG GCT CAG CAA ATG GTT CAG CCC CAG TCC CCG GTG GCT GTC AGT      143
Arg Gln Ala Gln Gln Met Val Gln Pro Gln Ser Pro Val Ala Val Ser
                35                  40                  45

CAA AGC AAG CCC GGT TGT TAT GAC AAT GGA AAA CAC TAT CAG ATA AAT      191
Gln Ser Lys Pro Gly Cys Tyr Asp Asn Gly Lys His Tyr Gln Ile Asn
            50                  55                  60

CAA CAG TGG GAG CGG ACC TAC CTA GGT AAT GTG TTG GTT TGT ACT TGT      239
Gln Gln Trp Glu Arg Thr Tyr Leu Gly Asn Val Leu Val Cys Thr Cys
65                  70                  75

TAT GGA GGA AGC CGA GGT TTT AAC TGC GAA AGT AAA CCT GAA GCT GAA      287
Tyr Gly Gly Ser Arg Gly Phe Asn Cys Glu Ser Lys Pro Glu Ala Glu
        80                  85                  90

GAG ACT TGC TTT GAC AAG TAC ACT GGG AAC ACT TAC CGA GTG GGT GAC      335
Glu Thr Cys Phe Asp Lys Tyr Thr Gly Asn Thr Tyr Arg Val Gly Asp
95                  100                 105                 110

ACT TAT GAG CGT CCT AAA GAC TCC ATG ATC TGG GAC TGT ACC TGC ATC      383
Thr Tyr Glu Arg Pro Lys Asp Ser Met Ile Trp Asp Cys Thr Cys Ile
                115                 120                 125

GGG GCT GGG CGA GGG AGA ATA AGC TGT ACC ATC GCA AAC CGC TGC CAT      431
```

|  |  |  |  |  |  |  |  |  |  |  |  |  |  |  |  |
|---|---|---|---|---|---|---|---|---|---|---|---|---|---|---|---|
| Gly | Ala | Gly | Arg<br>130 | Gly | Arg | Ile | Ser | Cys<br>135 | Thr | Ile | Ala | Asn | Arg<br>140 | Cys | His |

| GAA | GGG | GGT | CAG | TCC | TAC | AAG | ATT | GGT | GAC | ACC | TGG | AGG | AGA | CCA | CAT | 479 |
|---|---|---|---|---|---|---|---|---|---|---|---|---|---|---|---|---|
| Glu | Gly | Gly<br>145 | Gln | Ser | Tyr | Lys | Ile<br>150 | Gly | Asp | Thr | Trp | Arg<br>155 | Arg | Pro | His |  |

| GAG | ACT | GGT | GGT | TAC | ATG | TTA | GAG | TGT | GTG | TGT | CTT | GGT | AAT | GGA | AAA | 527 |
|---|---|---|---|---|---|---|---|---|---|---|---|---|---|---|---|---|
| Glu | Thr<br>160 | Gly | Gly | Tyr | Met | Leu<br>165 | Glu | Cys | Val | Cys | Leu<br>170 | Gly | Asn | Gly | Lys |  |

| GGA | GAA | TGG | ACC | TGC | AAG | CCC | ATA | GCT | GAG | AAG | TGT | TTT | GAT | CAT | GCT | 575 |
|---|---|---|---|---|---|---|---|---|---|---|---|---|---|---|---|---|
| Gly<br>175 | Glu | Trp | Thr | Cys | Lys<br>180 | Pro | Ile | Ala | Glu | Lys<br>185 | Cys | Phe | Asp | His | Ala<br>190 |  |

| GCT | GGG | ACT | TCC | TAT | GTG | GTC | GGA | GAA | ACG | TGG | GAG | AAG | CCC | TAC | CAA | 623 |
|---|---|---|---|---|---|---|---|---|---|---|---|---|---|---|---|---|
| Ala | Gly | Thr | Ser | Tyr<br>195 | Val | Val | Gly | Glu | Thr<br>200 | Trp | Glu | Lys | Pro | Tyr<br>205 | Gln |  |

| GGC | TGG | ATG | ATG | GTA | GAT | TGT | ACT | TGC | CTG | GGA | GAA | GGC | AGC | GGA | CGC | 671 |
|---|---|---|---|---|---|---|---|---|---|---|---|---|---|---|---|---|
| Gly | Trp | Met | Met<br>210 | Val | Asp | Cys | Thr | Cys<br>215 | Leu | Gly | Glu | Gly | Ser<br>220 | Gly | Arg |  |

| ATC | ACT | TGC | ACT | TCT | AGA | AAT | AGA | TGC | AAC | GAT | CAG | GAC | ACA | AGG | ACA | 719 |
|---|---|---|---|---|---|---|---|---|---|---|---|---|---|---|---|---|
| Ile | Thr | Cys<br>225 | Thr | Ser | Arg | Asn | Arg<br>230 | Cys | Asn | Asp | Gln | Asp<br>235 | Thr | Arg | Thr |  |

| TCC | TAT | AGA | ATT | GGA | GAC | ACC | TGG | AGC | AAG | AAG | GAT | AAT | CGA | GGA | AAC | 767 |
|---|---|---|---|---|---|---|---|---|---|---|---|---|---|---|---|---|
| Ser | Tyr<br>240 | Arg | Ile | Gly | Asp | Thr<br>245 | Trp | Ser | Lys | Lys | Asp<br>250 | Asn | Arg | Gly | Asn |  |

| CTG | CTC | CAG | TGC | ATC | TGC | ACA | GGC | AAC | GGC | CGA | GGA | GAG | TGG | AAG | TGT | 815 |
|---|---|---|---|---|---|---|---|---|---|---|---|---|---|---|---|---|
| Leu<br>255 | Leu | Gln | Cys | Ile | Cys<br>260 | Thr | Gly | Asn | Gly | Arg<br>265 | Gly | Glu | Trp | Lys | Cys<br>270 |  |

| GAG | AGG | CAC | ACC | TCT | GTG | CAG | ACC | ACA | TCG | AGC | GGA | TCT | GGC | CCC | TTC | 863 |
|---|---|---|---|---|---|---|---|---|---|---|---|---|---|---|---|---|
| Glu | Arg | His | Thr | Ser<br>275 | Val | Gln | Thr | Thr | Ser<br>280 | Ser | Gly | Ser | Gly | Pro<br>285 | Phe |  |

| ACC | GAT | GTT | CGT | GCA | GCT | GTT | TAC | CAA | CCG | CAG | CCT | CAC | CCC | CAG | CCT | 911 |
|---|---|---|---|---|---|---|---|---|---|---|---|---|---|---|---|---|
| Thr | Asp | Val | Arg<br>290 | Ala | Ala | Val | Tyr | Gln<br>295 | Pro | Gln | Pro | His | Pro<br>300 | Gln | Pro |  |

| CCT | CCC | TAT | GGC | CAC | TGT | GTC | ACA | GAC | AGT | GGT | GTG | GTC | TAC | TCT | GTG | 959 |
|---|---|---|---|---|---|---|---|---|---|---|---|---|---|---|---|---|
| Pro | Pro | Tyr<br>305 | Gly | His | Cys | Val | Thr<br>310 | Asp | Ser | Gly | Val | Val<br>315 | Tyr | Ser | Val |  |

| GGG | ATG | CAG | TGG | TTG | AAG | ACA | CAA | GGA | AAT | AAG | CAA | ATG | CTT | TGC | ACG | 1007 |
|---|---|---|---|---|---|---|---|---|---|---|---|---|---|---|---|---|
| Gly | Met<br>320 | Gln | Trp | Leu | Lys | Thr<br>325 | Gln | Gly | Asn | Lys | Gln<br>330 | Met | Leu | Cys | Thr |  |

| TGC | CTG | GGC | AAC | GGA | GTC | AGC | TGC | CAA | GAG | ACA | GCT | GTA | ACC | CAG | ACT | 1055 |
|---|---|---|---|---|---|---|---|---|---|---|---|---|---|---|---|---|
| Cys<br>335 | Leu | Gly | Asn | Gly | Val<br>340 | Ser | Cys | Gln | Glu | Thr<br>345 | Ala | Val | Thr | Gln | Thr<br>350 |  |

| TAC | GGT | GGC | AAC | TTA | AAT | GGA | GAG | CCA | TGT | GTC | TTA | CCA | TTC | ACC | TAC | 1103 |
|---|---|---|---|---|---|---|---|---|---|---|---|---|---|---|---|---|
| Tyr | Gly | Gly | Asn | Leu<br>355 | Asn | Gly | Glu | Pro | Cys<br>360 | Val | Leu | Pro | Phe | Thr<br>365 | Tyr |  |

| AAT | GGC | AGG | ACG | TTC | TAC | TCC | TGC | ACC | ACG | GAA | GGG | CGA | CAG | GAC | GGA | 1151 |
|---|---|---|---|---|---|---|---|---|---|---|---|---|---|---|---|---|
| Asn | Gly | Arg | Thr<br>370 | Phe | Tyr | Ser | Cys | Thr<br>375 | Thr | Glu | Gly | Arg | Gln<br>380 | Asp | Gly |  |

| CAT | CTT | TGG | TGC | AGC | ACA | ACT | TCG | AAT | TAT | GAG | CAG | GAC | CAG | AAA | TAC | 1199 |
|---|---|---|---|---|---|---|---|---|---|---|---|---|---|---|---|---|
| His | Leu | Trp<br>385 | Cys | Ser | Thr | Thr | Ser<br>390 | Asn | Tyr | Glu | Gln | Asp<br>395 | Gln | Lys | Tyr |  |

| TCT | TTC | TGC | ACA | GAC | CAC | ACT | GTT | TTG | GTT | CAG | ACT | CAA | GGA | GGA | AAT | 1247 |
|---|---|---|---|---|---|---|---|---|---|---|---|---|---|---|---|---|
| Ser | Phe<br>400 | Cys | Thr | Asp | His | Thr<br>405 | Val | Leu | Val | Gln | Thr<br>410 | Gln | Gly | Gly | Asn |  |

| TCC | AAT | GGT | GCC | TTG | TGC | CAC | TTC | CCC | TTC | CTA | TAC | AAC | AAC | CAC | AAT | 1295 |
|---|---|---|---|---|---|---|---|---|---|---|---|---|---|---|---|---|
| Ser<br>415 | Asn | Gly | Ala | Leu | Cys<br>420 | His | Phe | Pro | Phe | Leu<br>425 | Tyr | Asn | Asn | His | Asn<br>430 |  |

| TAC | ACT | GAT | TGC | ACT | TCT | GAG | GGC | AGA | AGA | GAC | AAC | ATG | AAG | TGG | TGT | 1343 |
|---|---|---|---|---|---|---|---|---|---|---|---|---|---|---|---|---|
| Tyr | Thr | Asp | Cys | Thr<br>435 | Ser | Glu | Gly | Arg | Arg<br>440 | Asp | Asn | Met | Lys | Trp<br>445 | Cys |  |

| GGG | ACC | ACA | CAG | AAC | TAT | GAT | GCC | GAC | CAG | AAG | TTT | GGG | TTC | TGC | CCC | 1391 |
|---|---|---|---|---|---|---|---|---|---|---|---|---|---|---|---|---|

```
Gly Thr Thr Gln Asn Tyr Asp Ala Asp Gln Lys Phe Gly Phe Cys Pro
            450                 455                 460

ATG GCT GCC CAC GAG GAA ATC TGC ACA ACC AAT GAA GGG GTC ATG TAC       1439
Met Ala Ala His Glu Glu Ile Cys Thr Thr Asn Glu Gly Val Met Tyr
        465                 470                 475

CGC ATT GGA GAT CAG TGG GAT AAG CAG CAT GAC ATG GGT CAC ATG ATG       1487
Arg Ile Gly Asp Gln Trp Asp Lys Gln His Asp Met Gly His Met Met
        480                 485                 490

AGG TGC ACG TGT GTT GGG AAT GGT CGT GGG GAA TGG ACA TGC ATT GCC       1535
Arg Cys Thr Cys Val Gly Asn Gly Arg Gly Glu Trp Thr Cys Ile Ala
495                 500                 505                 510

TAC TCG CAA CTT CGA GAT CAG TGC ATT GTT GAT GAC ATC ACT TAC AAT       1583
Tyr Ser Gln Leu Arg Asp Gln Cys Ile Val Asp Asp Ile Thr Tyr Asn
                515                 520                 525

GTG AAC GAC ACA TTC CAC AAG CGT CAT GAA GAG GGG CAC ATG CTG AAC       1631
Val Asn Asp Thr Phe His Lys Arg His Glu Glu Gly His Met Leu Asn
            530                 535                 540

TGT ACA TGC TTC GGT CAG GGT CGG GGC AGG TGG AAG TGT GAT CCC GTC       1679
Cys Thr Cys Phe Gly Gln Gly Arg Gly Arg Trp Lys Cys Asp Pro Val
            545                 550                 555

GAC CAA TGC CAG GAT TCA GAG ACT GGG ACG TTT TAT CAA ATT GGA GAT       1727
Asp Gln Cys Gln Asp Ser Glu Thr Gly Thr Phe Tyr Gln Ile Gly Asp
        560                 565                 570

TCA TGG GAG AAG TAT GTG CAT GGT GTC AGA TAC CAG TGC TAC TGC TAT       1775
Ser Trp Glu Lys Tyr Val His Gly Val Arg Tyr Gln Cys Tyr Cys Tyr
575                 580                 585                 590

GGC CGT GGC ATT GGG GAG TGG CAT TGC CAA CCT TTA CAG ACC TAT CCA       1823
Gly Arg Gly Ile Gly Glu Trp His Cys Gln Pro Leu Gln Thr Tyr Pro
                595                 600                 605

AGC TCA AGT GGT CCT GTC GAA GTA TTT ATC ACT GAG ACT CCG AGT CAG       1871
Ser Ser Ser Gly Pro Val Glu Val Phe Ile Thr Glu Thr Pro Ser Gln
            610                 615                 620

CCC AAC TCC CAC CCC ATC CAG TGG AAT GCA CCA CAG CCA TCT CAC ATT       1919
Pro Asn Ser His Pro Ile Gln Trp Asn Ala Pro Gln Pro Ser His Ile
            625                 630                 635

TCC AAG TAC ATT CTC AGG TGG AGA CCT AAA AAT TCT GTA GGC CGT TGG       1967
Ser Lys Tyr Ile Leu Arg Trp Arg Pro Lys Asn Ser Val Gly Arg Trp
640                 645                 650

AAG GAA GCT ACC ATA CCA GGC CAC TTA AAC TCC TAC ACC ATC AAA GGC       2015
Lys Glu Ala Thr Ile Pro Gly His Leu Asn Ser Tyr Thr Ile Lys Gly
655                 660                 665                 670

CTG AAG CCT GGT GTG GTA TAC GAG GGC CAG CTC ATC AGC ATC CAG CAG       2063
Leu Lys Pro Gly Val Val Tyr Glu Gly Gln Leu Ile Ser Ile Gln Gln
                675                 680                 685

TAC GGC CAC CAA GAA GTG ACT CGC TTT GAC TTC ACC ACC ACC AGC ACC       2111
Tyr Gly His Gln Glu Val Thr Arg Phe Asp Phe Thr Thr Thr Ser Thr
            690                 695                 700

AGC ACA CCT GTG ACC AGC AAC ACC GTG ACA GGA GAG ACG ACT CCC TTT       2159
Ser Thr Pro Val Thr Ser Asn Thr Val Thr Gly Glu Thr Thr Pro Phe
            705                 710                 715

TCT CCT CTT GTG GCC ACT TCT GAA TCT GTG ACC GAA ATC ACA GCC AGT       2207
Ser Pro Leu Val Ala Thr Ser Glu Ser Val Thr Glu Ile Thr Ala Ser
        720                 725                 730

AGC TTT GTG GTC TCC TGG GTC TCA GCT TCC GAC ACC GTG TCG GGA TTC       2255
Ser Phe Val Val Ser Trp Val Ser Ala Ser Asp Thr Val Ser Gly Phe
735                 740                 745                 750

CGG GTG GAA TAT GAG CTG AGT GAG GAG GGA GAT GAG CCA CAG TAC CTG       2303
Arg Val Glu Tyr Glu Leu Ser Glu Glu Gly Asp Glu Pro Gln Tyr Leu
                755                 760                 765

GAT CTT CCA AGC ACA GCC ACT TCT GTG AAC ATC CCT GAC CTG CTT CCT       2351
```

|     |     |     |     |     |     |     |     |     |     |     |     |     |     |     |     |
|-----|-----|-----|-----|-----|-----|-----|-----|-----|-----|-----|-----|-----|-----|-----|-----|
| Asp | Leu | Pro | Ser | Thr | Ala | Thr | Ser | Val | Asn | Ile | Pro | Asp | Leu | Leu | Pro |
|     |     |     |     770 |     |     |     775 |     |     |     |     |     780 |     |     |

| GGC | CGA | AAA | TAC | ATT | GTA | AAT | GTC | TAT | CAG | ATA | TCT | GAG | GAT | GGG | GAG | 2399 |
|-----|-----|-----|-----|-----|-----|-----|-----|-----|-----|-----|-----|-----|-----|-----|-----|------|
| Gly | Arg | Lys | Tyr | Ile | Val | Asn | Val | Tyr | Gln | Ile | Ser | Glu | Asp | Gly | Glu |      |
|     |     | 785 |     |     |     | 790 |     |     |     |     | 795 |     |     |     |     |      |

| CAG | AGT | TTG | ATC | CTG | TCT | ACT | TCA | CAA | ACA | ACA | GCG | CCT | GAT | GCC | CCT | 2447 |
| Gln | Ser | Leu | Ile | Leu | Ser | Thr | Ser | Gln | Thr | Thr | Ala | Pro | Asp | Ala | Pro |      |
|     | 800 |     |     |     |     | 805 |     |     |     |     | 810 |     |     |     |     |      |

| CCT | GAC | CCG | ACT | GTG | GAC | CAA | GTT | GAT | GAC | ACC | TCA | ATT | GTT | GTT | CGC | 2495 |
| Pro | Asp | Pro | Thr | Val | Asp | Gln | Val | Asp | Asp | Thr | Ser | Ile | Val | Val | Arg |      |
| 815 |     |     |     | 820 |     |     |     |     | 825 |     |     |     |     |     | 830 |      |

| TGG | AGC | AGA | CCC | CAG | GCT | CCC | ATC | ACA | GGG | TAC | AGA | ATA | GTC | TAT | TCG | 2543 |
| Trp | Ser | Arg | Pro | Gln | Ala | Pro | Ile | Thr | Gly | Tyr | Arg | Ile | Val | Tyr | Ser |      |
|     |     |     |     | 835 |     |     |     |     | 840 |     |     |     |     | 845 |     |      |

| CCA | TCA | GTA | GAA | GGT | AGC | AGC | ACA | GAA | CTC | AAC | CTT | CCT | GAA | ACT | GCA | 2591 |
| Pro | Ser | Val | Glu | Gly | Ser | Ser | Thr | Glu | Leu | Asn | Leu | Pro | Glu | Thr | Ala |      |
|     |     |     | 850 |     |     |     |     | 855 |     |     |     |     | 860 |     |     |      |

| AAC | TCC | GTC | ACC | CTC | AGT | GAC | TTG | CAA | CCT | GGT | GTT | CAG | TAT | AAC | ATC | 2639 |
| Asn | Ser | Val | Thr | Leu | Ser | Asp | Leu | Gln | Pro | Gly | Val | Gln | Tyr | Asn | Ile |      |
|     |     | 865 |     |     |     |     | 870 |     |     |     |     | 875 |     |     |     |      |

| ACT | ATC | TAT | GCT | GTG | GAA | GAA | AAT | CAA | GAA | AGT | ACA | CCT | GTT | GTC | ATT | 2687 |
| Thr | Ile | Tyr | Ala | Val | Glu | Glu | Asn | Gln | Glu | Ser | Thr | Pro | Val | Val | Ile |      |
|     | 880 |     |     |     |     | 885 |     |     |     |     | 890 |     |     |     |     |      |

| CAA | CAA | GAA | ACC | ACT | GGC | ACC | CCA | CGC | TCA | GAT | ACA | GTG | CCC | TCT | CCC | 2735 |
| Gln | Gln | Glu | Thr | Thr | Gly | Thr | Pro | Arg | Ser | Asp | Thr | Val | Pro | Ser | Pro |      |
| 895 |     |     |     |     | 900 |     |     |     |     | 905 |     |     |     |     | 910 |      |

| AGG | GAC | CTG | CAG | TTT | GTG | GAA | GTG | ACA | GAC | GTG | AAG | GTC | ACC | ATC | ATG | 2783 |
| Arg | Asp | Leu | Gln | Phe | Val | Glu | Val | Thr | Asp | Val | Lys | Val | Thr | Ile | Met |      |
|     |     |     |     | 915 |     |     |     |     | 920 |     |     |     |     | 925 |     |      |

| TGG | ACA | CCG | CCT | GAG | AGT | GCA | GTG | ACC | GGC | TAC | CGT | GTG | GAT | GTG | ATC | 2831 |
| Trp | Thr | Pro | Pro | Glu | Ser | Ala | Val | Thr | Gly | Tyr | Arg | Val | Asp | Val | Ile |      |
|     |     |     | 930 |     |     |     |     | 935 |     |     |     |     | 940 |     |     |      |

| CCC | GTC | AAC | CTG | CCT | GGC | GAG | CAC | GGG | CAG | AGG | CTG | CCC | ATC | AGC | AGG | 2879 |
| Pro | Val | Asn | Leu | Pro | Gly | Glu | His | Gly | Gln | Arg | Leu | Pro | Ile | Ser | Arg |      |
|     |     | 945 |     |     |     |     | 950 |     |     |     |     | 955 |     |     |     |      |

| AAC | ACC | TTT | GCA | GAA | GTC | ACC | GGG | CTG | TCC | CCT | GGG | GTC | ACC | TAT | TAC | 2927 |
| Asn | Thr | Phe | Ala | Glu | Val | Thr | Gly | Leu | Ser | Pro | Gly | Val | Thr | Tyr | Tyr |      |
|     | 960 |     |     |     |     | 965 |     |     |     |     | 970 |     |     |     |     |      |

| TTC | AAA | GTC | TTT | GCA | GTG | AGC | CAT | GGG | AGG | GAG | AGC | AAG | CCT | CTG | ACT | 2975 |
| Phe | Lys | Val | Phe | Ala | Val | Ser | His | Gly | Arg | Glu | Ser | Lys | Pro | Leu | Thr |      |
| 975 |     |     |     |     | 980 |     |     |     |     | 985 |     |     |     |     | 990 |      |

| GCT | CAA | CAG | ACA | ACC | AAA | CTG | GAT | GCT | CCC | ACT | AAC | CTC | CAG | TTT | GTC | 3023 |
| Ala | Gln | Gln | Thr | Thr | Lys | Leu | Asp | Ala | Pro | Thr | Asn | Leu | Gln | Phe | Val |      |
|     |     |     |     | 995 |     |     |     |     | 1000 |     |     |     |     | 1005 |     |      |

| AAT | GAA | ACT | GAT | TCT | ACT | GTC | CTG | GTG | AGA | TGG | ACT | CCA | CCT | CGG | GCC | 3071 |
| Asn | Glu | Thr | Asp | Ser | Thr | Val | Leu | Val | Arg | Trp | Thr | Pro | Pro | Arg | Ala |      |
|     |     |     | 1010 |     |     |     |     | 1015 |     |     |     |     | 1020 |     |     |      |

| CAG | ATA | ACA | GGA | TAC | CGA | CTG | ACC | GTG | GGC | CTT | ACC | CGA | AGA | GGC | CAG | 3119 |
| Gln | Ile | Thr | Gly | Tyr | Arg | Leu | Thr | Val | Gly | Leu | Thr | Arg | Arg | Gly | Gln |      |
|     |     |     | 1025 |     |     |     |     | 1030 |     |     |     |     | 1035 |     |     |      |

| CCC | AGG | CAG | TAC | AAT | GTG | GGT | CCC | TCT | GTC | TCC | AAG | TAC | CCC | CTG | AGG | 3167 |
| Pro | Arg | Gln | Tyr | Asn | Val | Gly | Pro | Ser | Val | Ser | Lys | Tyr | Pro | Leu | Arg |      |
|     | 1040 |     |     |     |     | 1045 |     |     |     |     | 1050 |     |     |     |     |      |

| AAT | CTG | CAG | CCT | GCA | TCT | GAG | TAC | ACC | GTA | TCC | CTC | GTG | GCC | ATA | AAG | 3215 |
| Asn | Leu | Gln | Pro | Ala | Ser | Glu | Tyr | Thr | Val | Ser | Leu | Val | Ala | Ile | Lys |      |
| 1055 |     |     |     |     | 1060 |     |     |     |     | 1065 |     |     |     |     | 1070 |      |

| GGC | AAC | CAA | GAG | AGC | CCC | AAA | GCC | ACT | GGA | GTC | TTT | ACC | ACA | CTG | CAG | 3263 |
| Gly | Asn | Gln | Glu | Ser | Pro | Lys | Ala | Thr | Gly | Val | Phe | Thr | Thr | Leu | Gln |      |
|     |     |     |     | 1075 |     |     |     |     | 1080 |     |     |     |     | 1085 |     |      |

| CCT | GGG | AGC | TCT | ATT | CCA | CCT | TAC | AAC | ACC | GAG | GTG | ACT | GAG | ACC | ACC | 3311 |

|  |  |  |  |  |  |  |  |  |  |  |  |  |  |  |  |
|---|---|---|---|---|---|---|---|---|---|---|---|---|---|---|---|
| Pro | Gly | Ser | Ser | Ile | Pro | Pro | Tyr | Asn | Thr | Glu | Val | Thr | Glu | Thr | Thr |
|  |  |  | 1090 |  |  |  | 1095 |  |  |  | 1100 |  |  |  |  |

| ATC | GTG | ATC | ACA | TGG | ACG | CCT | GCT | CCA | AGA | ATT | GGT | TTT | AAG | CTG | GGT | 3359 |
|---|---|---|---|---|---|---|---|---|---|---|---|---|---|---|---|---|
| Ile | Val | Ile | Thr | Trp | Thr | Pro | Ala | Pro | Arg | Ile | Gly | Phe | Lys | Leu | Gly |  |
|  |  |  | 1105 |  |  |  | 1110 |  |  |  | 1115 |  |  |  |  |  |

| GTA | CGA | CCA | AGC | CAG | GGA | GGA | GAG | GCA | CCA | CGA | GAA | GTG | ACT | TCA | GAC | 3407 |
|---|---|---|---|---|---|---|---|---|---|---|---|---|---|---|---|---|
| Val | Arg | Pro | Ser | Gln | Gly | Gly | Glu | Ala | Pro | Arg | Glu | Val | Thr | Ser | Asp |  |
|  |  | 1120 |  |  |  | 1125 |  |  |  | 1130 |  |  |  |  |  |  |

| TCA | GGA | AGC | ATC | GTT | GTG | TCC | GGC | TTG | ACT | CCA | GGA | GTA | GAA | TAC | GTC | 3455 |
|---|---|---|---|---|---|---|---|---|---|---|---|---|---|---|---|---|
| Ser | Gly | Ser | Ile | Val | Val | Ser | Gly | Leu | Thr | Pro | Gly | Val | Glu | Tyr | Val |  |
| 1135 |  |  |  | 1140 |  |  |  | 1145 |  |  |  |  | 1150 |  |  |  |

| TAC | ACC | ATC | CAA | GTC | CTG | AGA | GAT | GGA | CAG | GAA | AGA | GAT | GCG | CCA | ATT | 3503 |
|---|---|---|---|---|---|---|---|---|---|---|---|---|---|---|---|---|
| Tyr | Thr | Ile | Gln | Val | Leu | Arg | Asp | Gly | Gln | Glu | Arg | Asp | Ala | Pro | Ile |  |
|  |  |  | 1155 |  |  |  | 1160 |  |  |  | 1165 |  |  |  |  |  |

| GTA | AAC | AAA | GTG | GTG | ACA | CCA | TTG | TCT | CCA | CCA | ACA | AAC | TTG | CAT | CTG | 3551 |
|---|---|---|---|---|---|---|---|---|---|---|---|---|---|---|---|---|
| Val | Asn | Lys | Val | Val | Thr | Pro | Leu | Ser | Pro | Pro | Thr | Asn | Leu | His | Leu |  |
|  |  |  | 1170 |  |  |  | 1175 |  |  |  | 1180 |  |  |  |  |  |

| GAG | GCA | AAC | CCT | GAC | ACT | GGA | GTG | CTC | ACA | GTC | TCC | TGG | GAG | AGG | AGC | 3599 |
|---|---|---|---|---|---|---|---|---|---|---|---|---|---|---|---|---|
| Glu | Ala | Asn | Pro | Asp | Thr | Gly | Val | Leu | Thr | Val | Ser | Trp | Glu | Arg | Ser |  |
|  |  | 1185 |  |  |  | 1190 |  |  |  | 1195 |  |  |  |  |  |  |

| ACC | ACC | CCA | GAC | ATT | ACT | GGT | TAT | AGA | ATT | ACC | ACA | ACC | CCT | ACA | AAC | 3647 |
|---|---|---|---|---|---|---|---|---|---|---|---|---|---|---|---|---|
| Thr | Thr | Pro | Asp | Ile | Thr | Gly | Tyr | Arg | Ile | Thr | Thr | Thr | Pro | Thr | Asn |  |
| 1200 |  |  |  |  |  | 1205 |  |  |  | 1210 |  |  |  |  |  |  |

| GGC | CAG | CAG | GGA | AAT | TCT | TTG | GAA | GAA | GTG | GTC | CAT | GCT | GAT | CAG | AGC | 3695 |
|---|---|---|---|---|---|---|---|---|---|---|---|---|---|---|---|---|
| Gly | Gln | Gln | Gly | Asn | Ser | Leu | Glu | Glu | Val | Val | His | Ala | Asp | Gln | Ser |  |
| 1215 |  |  |  | 1220 |  |  |  |  | 1225 |  |  |  |  | 1230 |  |  |

| TCC | TGC | ACT | TTT | GAT | AAC | CTG | AGT | CCC | GGC | CTG | GAG | TAC | AAT | GTC | AGT | 3743 |
|---|---|---|---|---|---|---|---|---|---|---|---|---|---|---|---|---|
| Ser | Cys | Thr | Phe | Asp | Asn | Leu | Ser | Pro | Gly | Leu | Glu | Tyr | Asn | Val | Ser |  |
|  |  |  |  | 1235 |  |  |  |  | 1240 |  |  |  |  | 1245 |  |  |

| GTT | TAC | ACT | GTC | AAG | GAT | GAC | AAG | GAA | AGT | GTC | CCT | ATC | TCT | GAT | ACC | 3791 |
|---|---|---|---|---|---|---|---|---|---|---|---|---|---|---|---|---|
| Val | Tyr | Thr | Val | Lys | Asp | Asp | Lys | Glu | Ser | Val | Pro | Ile | Ser | Asp | Thr |  |
|  |  |  | 1250 |  |  |  |  | 1255 |  |  |  |  | 1260 |  |  |  |

| ATC | ATC | CCA | GAG | GTG | CCC | CAA | CTC | ACT | GAC | CTA | AGC | TTT | GTT | GAT | ATA | 3839 |
|---|---|---|---|---|---|---|---|---|---|---|---|---|---|---|---|---|
| Ile | Ile | Pro | Glu | Val | Pro | Gln | Leu | Thr | Asp | Leu | Ser | Phe | Val | Asp | Ile |  |
|  |  |  | 1265 |  |  |  |  | 1270 |  |  |  |  | 1275 |  |  |  |

| ACC | GAT | TCA | AGC | ATC | GGC | CTG | AGG | TGG | ACC | CCG | CTA | AAC | TCT | TCC | ACC | 3887 |
|---|---|---|---|---|---|---|---|---|---|---|---|---|---|---|---|---|
| Thr | Asp | Ser | Ser | Ile | Gly | Leu | Arg | Trp | Thr | Pro | Leu | Asn | Ser | Ser | Thr |  |
| 1280 |  |  |  |  |  | 1285 |  |  |  |  | 1290 |  |  |  |  |  |

| ATT | ATT | GGG | TAC | CGC | ATC | ACA | GTA | GTT | GCG | GCA | GGA | GAA | GGT | ATC | CCT | 3935 |
|---|---|---|---|---|---|---|---|---|---|---|---|---|---|---|---|---|
| Ile | Ile | Gly | Tyr | Arg | Ile | Thr | Val | Val | Ala | Ala | Gly | Glu | Gly | Ile | Pro |  |
| 1295 |  |  |  |  | 1300 |  |  |  |  | 1305 |  |  |  |  | 1310 |  |

| ATT | TTT | GAA | GAT | TTT | GTG | TAC | TCC | TCA | GTA | GGA | TAC | TAC | ACA | GTC | ACA | 3983 |
|---|---|---|---|---|---|---|---|---|---|---|---|---|---|---|---|---|
| Ile | Phe | Glu | Asp | Phe | Val | Tyr | Ser | Ser | Val | Gly | Tyr | Tyr | Thr | Val | Thr |  |
|  |  |  |  | 1315 |  |  |  |  | 1320 |  |  |  |  | 1325 |  |  |

| GGG | CTG | GAG | CCG | GGC | ATT | GAC | TAT | GAT | ATC | AGC | GTT | ATC | ACT | CTC | ATT | 4031 |
|---|---|---|---|---|---|---|---|---|---|---|---|---|---|---|---|---|
| Gly | Leu | Glu | Pro | Gly | Ile | Asp | Tyr | Asp | Ile | Ser | Val | Ile | Thr | Leu | Ile |  |
|  |  |  | 1330 |  |  |  |  | 1335 |  |  |  |  | 1340 |  |  |  |

| AAT | GGC | GGC | GAG | AGT | GCC | CCT | ACT | ACA | CTG | ACA | CAA | CAA | ACG | GCT | GTT | 4079 |
|---|---|---|---|---|---|---|---|---|---|---|---|---|---|---|---|---|
| Asn | Gly | Gly | Glu | Ser | Ala | Pro | Thr | Thr | Leu | Thr | Gln | Gln | Thr | Ala | Val |  |
|  |  | 1345 |  |  |  | 1350 |  |  |  | 1355 |  |  |  |  |  |  |

| CCT | CCT | CCC | ACT | GAC | CTG | CGA | TTC | ACC | AAC | ATT | GGT | CCA | GAC | ACC | ATG | 4127 |
|---|---|---|---|---|---|---|---|---|---|---|---|---|---|---|---|---|
| Pro | Pro | Pro | Thr | Asp | Leu | Arg | Phe | Thr | Asn | Ile | Gly | Pro | Asp | Thr | Met |  |
|  |  | 1360 |  |  |  | 1365 |  |  |  | 1370 |  |  |  |  |  |  |

| CGT | GTC | ACC | TGG | GCT | CCA | CCC | CCA | TCC | ATT | GAT | TTA | ACC | AAC | TTC | CTG | 4175 |
|---|---|---|---|---|---|---|---|---|---|---|---|---|---|---|---|---|
| Arg | Val | Thr | Trp | Ala | Pro | Pro | Pro | Ser | Ile | Asp | Leu | Thr | Asn | Phe | Leu |  |
| 1375 |  |  |  |  | 1380 |  |  |  | 1385 |  |  |  |  | 1390 |  |  |

| GTG | CGT | TAC | TCA | CCT | GTG | AAA | AAT | GAG | GAA | GAT | GTT | GCA | GAG | TTG | TCA | 4223 |
|---|---|---|---|---|---|---|---|---|---|---|---|---|---|---|---|---|
| Val | Arg | Tyr | Ser | Pro | Val | Lys | Asn | Glu | Glu | Asp | Val | Ala | Glu | Leu | Ser |  |
|  |  |  | 1395 |  |  |  |  | 1400 |  |  |  |  | 1405 |  |  |  |

| ATT | TCT | CCT | TCA | GAC | AAT | GCA | GTG | GTC | TTA | ACA | AAT | CTC | CTG | CCT | GGT | 4271 |
|---|---|---|---|---|---|---|---|---|---|---|---|---|---|---|---|---|

```
Ile Ser Pro Ser Asp Asn Ala Val Val Leu Thr Asn Leu Leu Pro Gly
        1410            1415               1420

ACA GAA TAT GTA GTG AGT GTC TCC AGT GTC TAC GAA CAA CAT GAG AGC    4319
Thr Glu Tyr Val Val Ser Val Ser Ser Val Tyr Glu Gln His Glu Ser
    1425            1430                1435

ACA CCT CTT AGA GGA AGA CAG AAA ACA GGT CTT GAT TCC CCA ACT GGC    4367
Thr Pro Leu Arg Gly Arg Gln Lys Thr Gly Leu Asp Ser Pro Thr Gly
    1440            1445                1450

ATT GAC TTT TCT GAT ATT ACT GCC AAC TCT TTT ACT GTG CAC TGG ATT    4415
Ile Asp Phe Ser Asp Ile Thr Ala Asn Ser Phe Thr Val His Trp Ile
1455            1460                1465                1470

GCT CCT CGA GCC ACC ATC ACT GGC TAC AGG ATC CGC CAT CAT CCC GAG    4463
Ala Pro Arg Ala Thr Ile Thr Gly Tyr Arg Ile Arg His His Pro Glu
            1475                1480                1485

CAC TTC AGT GGG AGA CCT CGA GAA GAT CGG GTG CCC CAC TCT CGG AAT    4511
His Phe Ser Gly Arg Pro Arg Glu Asp Arg Val Pro His Ser Arg Asn
                1490                1495                1500

TCC ATC ACC CTC ACC AAC CTC ACT CCA GGC ACA GAG TAT GTG GTC AGC    4559
Ser Ile Thr Leu Thr Asn Leu Thr Pro Gly Thr Glu Tyr Val Val Ser
        1505                1510                1515

ATC GTT GCT CTT AAT GGC AGA GAG GAA AGT CCC TTA TTG ATT GGC CAA    4607
Ile Val Ala Leu Asn Gly Arg Glu Glu Ser Pro Leu Leu Ile Gly Gln
    1520                1525                1530

CAA TCA ACA GTT TCT GAT GTT CCG AGG GAC CTG GAA GTT GTT GCT GCG    4655
Gln Ser Thr Val Ser Asp Val Pro Arg Asp Leu Glu Val Val Ala Ala
1535            1540                1545                1550

ACC CCC ACC AGC CTA CTG ATC AGC TGG GAT GCT CCT GCT GTC ACA GTG    4703
Thr Pro Thr Ser Leu Leu Ile Ser Trp Asp Ala Pro Ala Val Thr Val
            1555                1560                1565

AGA TAT TAC AGG ATC ACT TAC GGA GAA ACA GGA GGA AAT AGC CCT GTC    4751
Arg Tyr Tyr Arg Ile Thr Tyr Gly Glu Thr Gly Gly Asn Ser Pro Val
        1570                1575                1580

CAG GAG TTC ACT GTG CCT GGG AGC AAG TCT ACA GCT ACC ATC AGC GGC    4799
Gln Glu Phe Thr Val Pro Gly Ser Lys Ser Thr Ala Thr Ile Ser Gly
    1585                1590                1595

CTT AAA CCT GGA GTT GAT TAT ACC ATC ACT GTG TAT GCT GTC ACT GGC    4847
Leu Lys Pro Gly Val Asp Tyr Thr Ile Thr Val Tyr Ala Val Thr Gly
    1600                1605                1610

CGT GGA GAC AGC CCC GCA AGC AGC AAG CCA ATT TCC ATT AAT TAC CGA    4895
Arg Gly Asp Ser Pro Ala Ser Ser Lys Pro Ile Ser Ile Asn Tyr Arg
1615                1620                1625                1630

ACA GAA ATT GAC AAA CCA TCC CAG ATG CAA GTG ACC GAT GTT CAG GAC    4943
Thr Glu Ile Asp Lys Pro Ser Gln Met Gln Val Thr Asp Val Gln Asp
            1635                1640                1645

AAC AGC ATT AGT GTC AAG TGG CTG CCT TCA AGT TCC CCT GTT ACT GGT    4991
Asn Ser Ile Ser Val Lys Trp Leu Pro Ser Ser Ser Pro Val Thr Gly
        1650                1655                1660

TAC AGA GTA ACC ACC ACT CCC AAA AAT GGA CCA GGA CCA ACA AAA ACT    5039
Tyr Arg Val Thr Thr Thr Pro Lys Asn Gly Pro Gly Pro Thr Lys Thr
    1665                1670                1675

AAA ACT GCA GGT CCA GAT CAA ACA GAA ATG ACT ATT GAA GGC TTG CAG    5087
Lys Thr Ala Gly Pro Asp Gln Thr Glu Met Thr Ile Glu Gly Leu Gln
    1680                1685                1690

CCC ACA GTG GAG TAT GTG GTT AGT GTC TAT GCT CAG AAT CCA AGC GGA    5135
Pro Thr Val Glu Tyr Val Val Ser Val Tyr Ala Gln Asn Pro Ser Gly
1695                1700                1705                1710

GAG AGT CAG CCT CTG GTT CAG ACT GCA GTA ACC AAC ATT GAT CGC CCT    5183
Glu Ser Gln Pro Leu Val Gln Thr Ala Val Thr Asn Ile Asp Arg Pro
            1715                1720                1725

AAA GGA CTG GCA TTC ACT GAT GTG GAT GTC GAT TCC ATC AAA ATT GCT    5231
```

```
Lys Gly Leu Ala Phe Thr Asp Val Asp Val Asp Ser Ile Lys Ile Ala
                1730                1735                1740

TGG GAA AGC CCA CAG GGG CAA GTT TCC AGG TAC AGG GTG ACC TAC TCG            5279
Trp Glu Ser Pro Gln Gly Gln Val Ser Arg Tyr Arg Val Thr Tyr Ser
        1745                1750                1755

AGC CCT GAG GAT GGA ATC CAT GAG CTA TTC CCT GCA CCT GAT GGT GAA            5327
Ser Pro Glu Asp Gly Ile His Glu Leu Phe Pro Ala Pro Asp Gly Glu
    1760                1765                1770

GAA GAC ACT GCA GAG CTG CAA GGC CTC AGA CCG GGT TCT GAG TAC ACA            5375
Glu Asp Thr Ala Glu Leu Gln Gly Leu Arg Pro Gly Ser Glu Tyr Thr
1775                1780                1785                1790

GTC AGT GTG GTT GCC TTG CAC GAT GAT ATG GAG AGC CAG CCC CTG ATT            5423
Val Ser Val Val Ala Leu His Asp Asp Met Glu Ser Gln Pro Leu Ile
                1795                1800                1805

GGA ACC CAG TCC ACA GCT ATT CCT GCA CCA ACT GAC CTG AAG TTC ACT            5471
Gly Thr Gln Ser Thr Ala Ile Pro Ala Pro Thr Asp Leu Lys Phe Thr
        1810                1815                1820

CAG GTC ACA CCC ACA AGC CTG AGC GCC CAG TGG ACA CCA CCC AAT GTT            5519
Gln Val Thr Pro Thr Ser Leu Ser Ala Gln Trp Thr Pro Pro Asn Val
    1825                1830                1835

CAG CTC ACT GGA TAT CGA GTG CGG GTG ACC CCC AAG GAG AAG ACC GGA            5567
Gln Leu Thr Gly Tyr Arg Val Arg Val Thr Pro Lys Glu Lys Thr Gly
1840                1845                1850

CCA ATG AAA GAA ATC AAC CTT GCT CCT GAC AGC TCA TCC GTG GTT GTA            5615
Pro Met Lys Glu Ile Asn Leu Ala Pro Asp Ser Ser Ser Val Val Val
1855                1860                1865                1870

TCA GGA CTT ATG GTG GCC ACC AAA TAT GAA GTG AGT GTC TAT GCT CTT            5663
Ser Gly Leu Met Val Ala Thr Lys Tyr Glu Val Ser Val Tyr Ala Leu
            1875                1880                1885

AAG GAC ACT TTG ACA AGC AGA CCA GCT CAG GGT GTT GTC ACC ACT CTG            5711
Lys Asp Thr Leu Thr Ser Arg Pro Ala Gln Gly Val Val Thr Thr Leu
        1890                1895                1900

GAG AAT GTC AGC CCA CCA AGA AGG GCT CGT GTG ACA GAT GCT ACT GAG            5759
Glu Asn Val Ser Pro Pro Arg Arg Ala Arg Val Thr Asp Ala Thr Glu
    1905                1910                1915

ACC ACC ATC ACC ATT AGC TGG AGA ACC AAG ACT GAG ACG ATC ACT GGC            5807
Thr Thr Ile Thr Ile Ser Trp Arg Thr Lys Thr Glu Thr Ile Thr Gly
1920                1925                1930

TTC CAA GTT GAT GCC GTT CCA GCC AAT GGC CAG ACT CCA ATC CAG AGA            5855
Phe Gln Val Asp Ala Val Pro Ala Asn Gly Gln Thr Pro Ile Gln Arg
1935                1940                1945                1950

ACC ATC AAG CCA GAT GTC AGA AGC TAC ACC ATC ACA GGT TTA CAA CCA            5903
Thr Ile Lys Pro Asp Val Arg Ser Tyr Thr Ile Thr Gly Leu Gln Pro
            1955                1960                1965

GGC ACT GAC TAC AAG ATC TAC CTG TAC ACC TTG AAT GAC AAT GCT CGG            5951
Gly Thr Asp Tyr Lys Ile Tyr Leu Tyr Thr Leu Asn Asp Asn Ala Arg
        1970                1975                1980

AGC TCC CCT GTG GTC ATC GAC GCC TCC ACT GCC ATT GAT GCA CCA TCC            5999
Ser Ser Pro Val Val Ile Asp Ala Ser Thr Ala Ile Asp Ala Pro Ser
    1985                1990                1995

AAC CTG CGT TTC CTG GCC ACC ACA CCC AAT TCC TTG CTG GTA TCA TGG            6047
Asn Leu Arg Phe Leu Ala Thr Thr Pro Asn Ser Leu Leu Val Ser Trp
2000                2005                2010

CAG CCG CCA CGT GCC AGG ATT ACC GGC TAC ATC ATC AAG TAT GAG AAG            6095
Gln Pro Pro Arg Ala Arg Ile Thr Gly Tyr Ile Ile Lys Tyr Glu Lys
2015                2020                2025                2030

CCT GGG TCT CCT CCC AGA GAA GTG GTC CCT CGG CCC CGC CCT GGT GTC            6143
Pro Gly Ser Pro Pro Arg Glu Val Val Pro Arg Pro Arg Pro Gly Val
            2035                2040                2045

ACA GAG GCT ACT ATT ACT GGC CTG GAA CCG GGA ACC GAA TAT ACA ATT            6191
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Thr | Glu | Ala | Thr | Ile | Thr | Gly | Leu | Glu | Pro | Gly | Thr | Glu | Tyr | Thr | Ile  |
|     |     |     |     | 2050|     |     |     | 2055|     |     |     |     | 2060|     |      |
| TAT | GTC | ATT | GCC | CTG | AAG | AAT | AAT | CAG | AAG | AGC | GAG | CCC | CTG | ATT | GGA  | 6239 |
| Tyr | Val | Ile | Ala | Leu | Lys | Asn | Asn | Gln | Lys | Ser | Glu | Pro | Leu | Ile | Gly  |
|     |     |     |     | 2065|     |     |     | 2070|     |     |     |     | 2075|     |      |
| AGG | AAA | AAG | ACA | GAC | GAG | CTT | CCC | CAA | CTG | GTA | ACC | CTT | CCA | CAC | CCC  | 6287 |
| Arg | Lys | Lys | Thr | Asp | Glu | Leu | Pro | Gln | Leu | Val | Thr | Leu | Pro | His | Pro  |
|     |     |     | 2080|     |     |     |     | 2085|     |     |     |     | 2090|     |      |
| AAT | CTT | CAT | GGA | CCA | GAG | ATC | TTG | GAT | GTT | CCT | TCC | ACA | GTT | CAA | AAG  | 6335 |
| Asn | Leu | His | Gly | Pro | Glu | Ile | Leu | Asp | Val | Pro | Ser | Thr | Val | Gln | Lys  |
| 2095|     |     |     |     | 2100|     |     |     |     | 2105|     |     |     |     | 2110 |
| ACC | CCT | TTC | GTC | ACC | CAC | CCT | GGG | TAT | GAC | ACT | GGA | AAT | GGT | ATT | CAG  | 6383 |
| Thr | Pro | Phe | Val | Thr | His | Pro | Gly | Tyr | Asp | Thr | Gly | Asn | Gly | Ile | Gln  |
|     |     |     |     | 2115|     |     |     |     | 2120|     |     |     |     | 2125|      |
| CTT | CCT | GGC | ACT | TCT | GGT | CAG | CAA | CCC | AGT | GTT | GGG | CAA | CAA | ATG | ATC  | 6431 |
| Leu | Pro | Gly | Thr | Ser | Gly | Gln | Gln | Pro | Ser | Val | Gly | Gln | Gln | Met | Ile  |
|     |     |     |     | 2130|     |     |     |     | 2135|     |     |     |     | 2140|      |
| TTT | GAG | GAA | CAT | GGT | TTT | AGG | CGG | ACC | ACA | CCG | CCC | ACA | ACG | GCC | ACC  | 6479 |
| Phe | Glu | Glu | His | Gly | Phe | Arg | Arg | Thr | Thr | Pro | Pro | Thr | Thr | Ala | Thr  |
|     |     |     |     | 2145|     |     |     |     | 2150|     |     |     |     | 2155|      |
| CCC | ATA | AGG | CAT | AGG | CCA | AGA | CCA | TAC | CCG | CCG | AAT | GTA | GGA | CAA | GAA  | 6527 |
| Pro | Ile | Arg | His | Arg | Pro | Arg | Pro | Tyr | Pro | Pro | Asn | Val | Gly | Gln | Glu  |
|     | 2160|     |     |     |     | 2165|     |     |     |     | 2170|     |     |     |      |
| GCT | CTC | TCT | CAG | ACA | ACC | ATC | TCA | TGG | GCC | CCA | TTC | CAG | GAC | ACT | TCT  | 6575 |
| Ala | Leu | Ser | Gln | Thr | Thr | Ile | Ser | Trp | Ala | Pro | Phe | Gln | Asp | Thr | Ser  |
| 2175|     |     |     |     | 2180|     |     |     |     | 2185|     |     |     |     | 2190 |
| GAG | TAC | ATC | ATT | TCA | TGT | CAT | CCT | GTT | GGC | ACT | GAT | GAA | GAA | CCC | TTA  | 6623 |
| Glu | Tyr | Ile | Ile | Ser | Cys | His | Pro | Val | Gly | Thr | Asp | Glu | Glu | Pro | Leu  |
|     |     |     |     | 2195|     |     |     |     | 2200|     |     |     |     | 2205|      |
| CAG | TTC | AGG | GTT | CCT | GGA | ACT | TCT | ACC | AGT | GCC | ACT | CTG | ACA | GGC | CTC  | 6671 |
| Gln | Phe | Arg | Val | Pro | Gly | Thr | Ser | Thr | Ser | Ala | Thr | Leu | Thr | Gly | Leu  |
|     |     |     |     | 2210|     |     |     |     | 2215|     |     |     |     | 2220|      |
| ACC | AGA | GGT | GCC | ACC | TAC | AAC | ATC | ATA | GTG | GAG | GCA | CTG | AAA | GAC | CAG  | 6719 |
| Thr | Arg | Gly | Ala | Thr | Tyr | Asn | Ile | Ile | Val | Glu | Ala | Leu | Lys | Asp | Gln  |
|     |     |     | 2225|     |     |     |     | 2230|     |     |     |     | 2235|     |      |
| CAG | AGG | CAT | AAG | GTT | CGG | GAA | GAG | GTT | GTT | ACC | GTG | GGC | AAC | TCT | GTC  | 6767 |
| Gln | Arg | His | Lys | Val | Arg | Glu | Glu | Val | Val | Thr | Val | Gly | Asn | Ser | Val  |
|     | 2240|     |     |     |     | 2245|     |     |     |     | 2250|     |     |     |      |
| AAC | GAA | GGC | TTG | AAC | CAA | CCT | ACG | GAT | GAC | TCG | TGC | TTT | GAC | CCC | TAC  | 6815 |
| Asn | Glu | Gly | Leu | Asn | Gln | Pro | Thr | Asp | Asp | Ser | Cys | Phe | Asp | Pro | Tyr  |
| 2255|     |     |     |     | 2260|     |     |     |     | 2265|     |     |     |     | 2270 |
| ACA | GTT | TCC | CAT | TAT | GCC | GTT | GGA | GAT | GAG | TGG | GAA | CGA | ATG | TCT | GAA  | 6863 |
| Thr | Val | Ser | His | Tyr | Ala | Val | Gly | Asp | Glu | Trp | Glu | Arg | Met | Ser | Glu  |
|     |     |     |     | 2275|     |     |     |     | 2280|     |     |     |     | 2285|      |
| TCA | GGC | TTT | AAA | CTG | TTG | TGC | CAG | TGC | TTA | GGC | TTT | GGA | AGT | GGT | CAT  | 6911 |
| Ser | Gly | Phe | Lys | Leu | Leu | Cys | Gln | Cys | Leu | Gly | Phe | Gly | Ser | Gly | His  |
|     |     |     |     | 2290|     |     |     |     | 2295|     |     |     |     | 2300|      |
| TTC | AGA | TGT | GAT | TCA | TCT | AGA | TGG | TGC | CAT | GAC | AAT | GGT | GTG | AAC | TAC  | 6959 |
| Phe | Arg | Cys | Asp | Ser | Ser | Arg | Trp | Cys | His | Asp | Asn | Gly | Val | Asn | Tyr  |
|     |     |     | 2305|     |     |     |     | 2310|     |     |     |     | 2315|     |      |
| AAG | ATT | GGA | GAG | AAG | TGG | GAC | CGT | CAG | GGA | GAA | AAT | GGC | CAG | ATG | ATG  | 7007 |
| Lys | Ile | Gly | Glu | Lys | Trp | Asp | Arg | Gln | Gly | Glu | Asn | Gly | Gln | Met | Met  |
|     |     | 2320|     |     |     |     | 2325|     |     |     |     | 2330|     |     |      |
| AGC | TGC | ACA | TGT | CTT | GGG | AAC | GGA | AAA | GGA | GAA | TTC | AAG | TGT | GAC | CCT  | 7055 |
| Ser | Cys | Thr | Cys | Leu | Gly | Asn | Gly | Lys | Gly | Glu | Phe | Lys | Cys | Asp | Pro  |
| 2335|     |     |     |     | 2340|     |     |     |     | 2345|     |     |     |     | 2350 |
| CAT | GAG | GCA | ACG | TGT | TAC | GAT | GAT | GGG | AAG | ACA | TAC | CAC | GTA | GGA | GAA  | 7103 |
| His | Glu | Ala | Thr | Cys | Tyr | Asp | Asp | Gly | Lys | Thr | Tyr | His | Val | Gly | Glu  |
|     |     |     | 2355|     |     |     |     | 2360|     |     |     |     | 2365|     |      |
| CAG | TGG | CAG | AAG | GAA | TAT | CTC | GGT | GCC | ATT | TGC | TCC | TGC | ACA | TGC | TTT  | 7151 |

```
Gln  Trp  Gln  Lys  Glu  Tyr  Leu  Gly  Ala  Ile  Cys  Ser  Cys  Thr  Cys  Phe
          2370                    2375                    2380

GGA  GGC  CAG  CGG  GGC  TGG  CGC  TGT  GAC  AAC  TGC  CGC  AGA  CCT  GGG  GGT       7199
Gly  Gly  Gln  Arg  Gly  Trp  Arg  Cys  Asp  Asn  Cys  Arg  Arg  Pro  Gly  Gly
          2385                    2390                    2395

GAA  CCC  AGT  CCC  GAA  GGC  ACT  ACT  GGC  CAG  TCC  TAC  AAC  CAG  TAT  TCT       7247
Glu  Pro  Ser  Pro  Glu  Gly  Thr  Thr  Gly  Gln  Ser  Tyr  Asn  Gln  Tyr  Ser
          2400                    2405                    2410

CAG  AGA  TAC  CAT  CAG  AGA  ACA  AAC  ACT  AAT  GTT  AAT  TGC  CCA  ATT  GAG       7295
Gln  Arg  Tyr  His  Gln  Arg  Thr  Asn  Thr  Asn  Val  Asn  Cys  Pro  Ile  Glu
2415                2420                    2425                         2430

TGC  TTC  ATG  CCT  TTA  GAT  GTA  CAG  GCT  GAC  AGA  GAA  GAT  TCC  CGA  GAG       7343
Cys  Phe  Met  Pro  Leu  Asp  Val  Gln  Ala  Asp  Arg  Glu  Asp  Ser  Arg  Glu
               2435                    2440                    2445

TAAATCATCT  TTCCAATCCA  GAGGAACAAG  CATGTCTCTC  TGCCAAGATC  CATCTAAACT               7403

GGAGTGATGT  TAGCAGACCC  AGCTTAGAGT  TCTTCTTTCT  TTCTTAAGCC  CTTTGCTCTG               7463

GAGGAAGTTC  TCCAGCTTCA  GCTCAACTCA  CAGCTTCTCC  AAGCATCACC  CTGGGAGTTT               7523

CCTGAGGGTT  TTCTCATAAA  TGAGGGCTGC  ACATTGCCTG  TTCTGCTTCG  AAGTATTCAA               7583

TACCGCTCAG  TATTTTAAAT  GAAGTGATTC  TAAGATTTGG  TTTGGGATCA  ATAGGAAAGC               7643

ATATGCAGCC  AACCAAGATG  CAAATGTTTT  GAAATGATAT  GACCAAAATT  TTAAGTAGGA               7703

AAGTCACCCA  AACACTTCTG  CTTTCACTTA  AGTGTCTGGC  CCGCAATACT  GTAGGAACAA               7763

GCATGATCTT  GTTACTGTGA  TATTTAAAT   ATCCACAGTA                                       7803
```

(2) INFORMATION FOR SEQ ID NO:2:

(i) SEQUENCE CHARACTERISTICS:
        (A) LENGTH: 2446 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Leu  Arg  Gly  Pro  Gly  Pro  Gly  Leu  Leu  Leu  Leu  Ala  Val  Leu  Cys
 1              5                   10                      15

Leu  Gly  Thr  Ala  Val  Pro  Ser  Thr  Gly  Ala  Ser  Lys  Ser  Lys  Arg  Gln
               20                   25                      30

Ala  Gln  Gln  Met  Val  Gln  Pro  Gln  Ser  Pro  Val  Ala  Val  Ser  Gln  Ser
               35                   40                      45

Lys  Pro  Gly  Cys  Tyr  Asp  Asn  Gly  Lys  His  Tyr  Gln  Ile  Asn  Gln  Gln
     50                   55                      60

Trp  Glu  Arg  Thr  Tyr  Leu  Gly  Asn  Val  Leu  Val  Cys  Thr  Cys  Tyr  Gly
 65                  70                      75                         80

Gly  Ser  Arg  Gly  Phe  Asn  Cys  Glu  Ser  Lys  Pro  Glu  Ala  Glu  Glu  Thr
               85                   90                      95

Cys  Phe  Asp  Lys  Tyr  Thr  Gly  Asn  Thr  Tyr  Arg  Val  Gly  Asp  Thr  Tyr
               100                  105                     110

Glu  Arg  Pro  Lys  Asp  Ser  Met  Ile  Trp  Asp  Cys  Thr  Cys  Ile  Gly  Ala
               115                  120                     125

Gly  Arg  Gly  Arg  Ile  Ser  Cys  Thr  Ile  Ala  Asn  Arg  Cys  His  Glu  Gly
     130                  135                     140

Gly  Gln  Ser  Tyr  Lys  Ile  Gly  Asp  Thr  Trp  Arg  Arg  Pro  His  Glu  Thr
145                  150                  155                         160

Gly  Gly  Tyr  Met  Leu  Glu  Cys  Val  Cys  Leu  Gly  Asn  Gly  Lys  Gly  Glu
               165                  170                     175
```

-continued

| | | | | | | | | | | | | | | |
|---|---|---|---|---|---|---|---|---|---|---|---|---|---|---|
| Trp | Thr | Cys | Lys 180 | Pro | Ile | Ala | Glu | Lys 185 | Cys | Phe | Asp | His | Ala 190 | Ala | Gly |
| Thr | Ser | Tyr 195 | Val | Val | Gly | Glu | Thr 200 | Trp | Glu | Lys | Pro | Tyr 205 | Gln | Gly | Trp |
| Met | Met 210 | Val | Asp | Cys | Thr | Cys 215 | Leu | Gly | Glu | Gly | Ser 220 | Gly | Arg | Ile | Thr |
| Cys 225 | Thr | Ser | Arg | Asn | Arg 230 | Cys | Asn | Asp | Gln | Thr 235 | Arg | Thr | Ser | Tyr 240 |
| Arg | Ile | Gly | Asp | Thr 245 | Trp | Ser | Lys | Lys | Asp 250 | Asn | Arg | Gly | Asn | Leu 255 | Leu |
| Gln | Cys | Ile | Cys 260 | Thr | Gly | Asn | Gly | Arg 265 | Gly | Glu | Trp | Lys | Cys 270 | Glu | Arg |
| His | Thr | Ser 275 | Val | Gln | Thr | Thr | Ser 280 | Ser | Gly | Ser | Gly | Pro 285 | Phe | Thr | Asp |
| Val | Arg 290 | Ala | Ala | Val | Tyr | Gln 295 | Pro | Gln | Pro | His | Pro 300 | Gln | Pro | Pro | Pro |
| Tyr 305 | Gly | His | Cys | Val | Thr 310 | Asp | Ser | Gly | Val | Val 315 | Tyr | Ser | Val | Gly | Met 320 |
| Gln | Trp | Leu | Lys | Thr 325 | Gln | Gly | Asn | Lys | Met 330 | Leu | Cys | Thr | Cys 335 | Leu |
| Gly | Asn | Gly | Val 340 | Ser | Cys | Gln | Glu | Thr 345 | Ala | Val | Thr | Gln | Thr 350 | Tyr | Gly |
| Gly | Asn | Leu 355 | Asn | Gly | Glu | Pro | Cys 360 | Val | Leu | Pro | Phe | Thr 365 | Tyr | Asn | Gly |
| Arg | Thr 370 | Phe | Tyr | Ser | Cys | Thr 375 | Thr | Glu | Gly | Arg | Gln 380 | Asp | Gly | His | Leu |
| Trp 385 | Cys | Ser | Thr | Thr | Ser 390 | Asn | Tyr | Glu | Gln | Asp 395 | Gln | Lys | Tyr | Ser | Phe 400 |
| Cys | Thr | Asp | His | Thr 405 | Val | Leu | Val | Gln | Thr 410 | Gln | Gly | Gly | Asn | Ser 415 | Asn |
| Gly | Ala | Leu | Cys 420 | His | Phe | Pro | Phe | Leu 425 | Tyr | Asn | Asn | His | Asn 430 | Tyr | Thr |
| Asp | Cys | Thr 435 | Ser | Glu | Gly | Arg | Arg 440 | Asp | Asn | Met | Lys | Trp 445 | Cys | Gly | Thr |
| Thr | Gln 450 | Asn | Tyr | Asp | Ala | Asp 455 | Gln | Lys | Phe | Gly | Phe 460 | Cys | Pro | Met | Ala |
| Ala 465 | His | Glu | Glu | Ile | Cys 470 | Thr | Thr | Asn | Glu | Gly 475 | Val | Met | Tyr | Arg | Ile 480 |
| Gly | Asp | Gln | Trp | Asp 485 | Lys | Gln | His | Asp | Met 490 | Gly | His | Met | Met | Arg 495 | Cys |
| Thr | Cys | Val | Gly 500 | Asn | Gly | Arg | Gly | Glu 505 | Trp | Thr | Cys | Ile | Ala 510 | Tyr | Ser |
| Gln | Leu | Arg 515 | Asp | Gln | Cys | Ile | Val 520 | Asp | Asp | Ile | Thr | Tyr 525 | Asn | Val | Asn |
| Asp | Thr 530 | Phe | His | Lys | Arg | His 535 | Glu | Glu | Gly | His | Met 540 | Leu | Asn | Cys | Thr |
| Cys 545 | Phe | Gly | Gln | Gly | Arg 550 | Gly | Arg | Trp | Lys | Cys 555 | Asp | Pro | Val | Asp 560 | Gln |
| Cys | Gln | Asp | Ser | Glu 565 | Thr | Gly | Thr | Phe | Tyr 570 | Gln | Ile | Gly | Asp | Ser 575 | Trp |
| Glu | Lys | Tyr | Val 580 | His | Gly | Val | Arg | Tyr 585 | Gln | Cys | Tyr | Cys 590 | Tyr | Gly | Arg |
| Gly | Ile | Gly 595 | Glu | Trp | His | Cys | Gln 600 | Pro | Leu | Gln | Thr | Tyr 605 | Pro | Ser | Ser |

```
Ser  Gly  Pro  Val  Glu  Val  Phe  Ile  Thr  Glu  Thr  Pro  Ser  Gln  Pro  Asn
     610                 615                      620

Ser  His  Pro  Ile  Gln  Trp  Asn  Ala  Pro  Gln  Pro  Ser  His  Ile  Ser  Lys
625                      630                 635                           640

Tyr  Ile  Leu  Arg  Trp  Arg  Pro  Lys  Asn  Ser  Val  Gly  Arg  Trp  Lys  Glu
                    645                 650                      655

Ala  Thr  Ile  Pro  Gly  His  Leu  Asn  Ser  Tyr  Thr  Ile  Lys  Gly  Leu  Lys
               660                 665                           670

Pro  Gly  Val  Val  Tyr  Glu  Gly  Gln  Leu  Ile  Ser  Ile  Gln  Gln  Tyr  Gly
               675                 680                 685

His  Gln  Glu  Val  Thr  Arg  Phe  Asp  Phe  Thr  Thr  Thr  Ser  Thr  Ser  Thr
     690                 695                      700

Pro  Val  Thr  Ser  Asn  Thr  Val  Thr  Gly  Glu  Thr  Thr  Pro  Phe  Ser  Pro
705                      710                 715                           720

Leu  Val  Ala  Thr  Ser  Glu  Ser  Val  Thr  Glu  Ile  Thr  Ala  Ser  Ser  Phe
                    725                 730                      735

Val  Val  Ser  Trp  Val  Ser  Ala  Ser  Asp  Thr  Val  Ser  Gly  Phe  Arg  Val
               740                 745                      750

Glu  Tyr  Glu  Leu  Ser  Glu  Glu  Gly  Asp  Glu  Pro  Gln  Tyr  Leu  Asp  Leu
          755                      760                 765

Pro  Ser  Thr  Ala  Thr  Ser  Val  Asn  Ile  Pro  Asp  Leu  Leu  Pro  Gly  Arg
     770                 775                      780

Lys  Tyr  Ile  Val  Asn  Val  Tyr  Gln  Ile  Ser  Glu  Asp  Gly  Glu  Gln  Ser
785                      790                 795                           800

Leu  Ile  Leu  Ser  Thr  Ser  Gln  Thr  Thr  Ala  Pro  Asp  Ala  Pro  Pro  Asp
                    805                 810                      815

Pro  Thr  Val  Asp  Gln  Val  Asp  Asp  Thr  Ser  Ile  Val  Val  Arg  Trp  Ser
               820                 825                      830

Arg  Pro  Gln  Ala  Pro  Ile  Thr  Gly  Tyr  Arg  Ile  Val  Tyr  Ser  Pro  Ser
          835                      840                 845

Val  Glu  Gly  Ser  Ser  Thr  Glu  Leu  Asn  Leu  Pro  Glu  Thr  Ala  Asn  Ser
     850                 855                      860

Val  Thr  Leu  Ser  Asp  Leu  Gln  Pro  Gly  Val  Gln  Tyr  Asn  Ile  Thr  Ile
865                      870                 875                           880

Tyr  Ala  Val  Glu  Glu  Asn  Gln  Glu  Ser  Thr  Pro  Val  Val  Ile  Gln  Gln
                    885                 890                      895

Glu  Thr  Thr  Gly  Thr  Pro  Arg  Ser  Asp  Thr  Val  Pro  Ser  Pro  Arg  Asp
               900                 905                      910

Leu  Gln  Phe  Val  Glu  Val  Thr  Asp  Val  Lys  Val  Thr  Ile  Met  Trp  Thr
          915                      920                 925

Pro  Pro  Glu  Ser  Ala  Val  Thr  Gly  Tyr  Arg  Val  Asp  Val  Ile  Pro  Val
     930                 935                      940

Asn  Leu  Pro  Gly  Glu  His  Gly  Gln  Arg  Leu  Pro  Ile  Ser  Arg  Asn  Thr
945                      950                 955                           960

Phe  Ala  Glu  Val  Thr  Gly  Leu  Ser  Pro  Gly  Val  Thr  Tyr  Tyr  Phe  Lys
                    965                 970                      975

Val  Phe  Ala  Val  Ser  His  Gly  Arg  Glu  Ser  Lys  Pro  Leu  Thr  Ala  Gln
               980                 985                      990

Gln  Thr  Thr  Lys  Leu  Asp  Ala  Pro  Thr  Asn  Leu  Gln  Phe  Val  Asn  Glu
          995                      1000                1005

Thr  Asp  Ser  Thr  Val  Leu  Val  Arg  Trp  Thr  Pro  Pro  Arg  Ala  Gln  Ile
     1010                1015                     1020

Thr  Gly  Tyr  Arg  Leu  Thr  Val  Gly  Leu  Thr  Arg  Arg  Gly  Gln  Pro  Arg
```

-continued

```
            1025                1030                1035                1040
Gln Tyr Asn Val Gly Pro Ser Val Ser Lys Tyr Pro Leu Arg Asn Leu
                       1045                1050                1055
Gln Pro Ala Ser Glu Tyr Thr Val Ser Leu Val Ala Ile Lys Gly Asn
                       1060                1065                1070
Gln Glu Ser Pro Lys Ala Thr Gly Val Phe Thr Thr Leu Gln Pro Gly
                       1075                1080                1085
Ser Ser Ile Pro Pro Tyr Asn Thr Glu Val Thr Glu Thr Thr Ile Val
                       1090                1095                1100
Ile Thr Trp Thr Pro Ala Pro Arg Ile Gly Phe Lys Leu Gly Val Arg
1105                   1110                1115                1120
Pro Ser Gln Gly Gly Glu Ala Pro Arg Glu Val Thr Ser Asp Ser Gly
                       1125                1130                1135
Ser Ile Val Val Ser Gly Leu Thr Pro Gly Val Glu Tyr Val Tyr Thr
                       1140                1145                1150
Ile Gln Val Leu Arg Asp Gly Gln Glu Arg Asp Ala Pro Ile Val Asn
                       1155                1160                1165
Lys Val Val Thr Pro Leu Ser Pro Pro Thr Asn Leu His Leu Glu Ala
                       1170                1175                1180
Asn Pro Asp Thr Gly Val Leu Thr Val Ser Trp Glu Arg Ser Thr Thr
1185                   1190                1195                1200
Pro Asp Ile Thr Gly Tyr Arg Ile Thr Thr Thr Pro Thr Asn Gly Gln
                       1205                1210                1215
Gln Gly Asn Ser Leu Glu Glu Val Val His Ala Asp Gln Ser Ser Cys
                       1220                1225                1230
Thr Phe Asp Asn Leu Ser Pro Gly Leu Glu Tyr Asn Val Ser Val Tyr
                       1235                1240                1245
Thr Val Lys Asp Asp Lys Glu Ser Val Pro Ile Ser Asp Thr Ile Ile
                       1250                1255                1260
Pro Glu Val Pro Gln Leu Thr Asp Leu Ser Phe Val Asp Ile Thr Asp
1265                   1270                1275                1280
Ser Ser Ile Gly Leu Arg Trp Thr Pro Leu Asn Ser Ser Thr Ile Ile
                       1285                1290                1295
Gly Tyr Arg Ile Thr Val Val Ala Ala Gly Glu Gly Ile Pro Ile Phe
                       1300                1305                1310
Glu Asp Phe Val Tyr Ser Ser Val Gly Tyr Tyr Thr Val Thr Gly Leu
                       1315                1320                1325
Glu Pro Gly Ile Asp Tyr Asp Ile Ser Val Ile Thr Leu Ile Asn Gly
                       1330                1335                1340
Gly Glu Ser Ala Pro Thr Thr Leu Thr Gln Gln Thr Ala Val Pro Pro
1345                   1350                1355                1360
Pro Thr Asp Leu Arg Phe Thr Asn Ile Gly Pro Asp Thr Met Arg Val
                       1365                1370                1375
Thr Trp Ala Pro Pro Pro Ser Ile Asp Leu Thr Asn Phe Leu Val Arg
                       1380                1385                1390
Tyr Ser Pro Val Lys Asn Glu Glu Asp Val Ala Glu Leu Ser Ile Ser
                       1395                1400                1405
Pro Ser Asp Asn Ala Val Val Leu Thr Asn Leu Leu Pro Gly Thr Glu
                       1410                1415                1420
Tyr Val Val Ser Val Ser Ser Val Tyr Glu Gln His Glu Ser Thr Pro
1425                   1430                1435                1440
Leu Arg Gly Arg Gln Lys Thr Gly Leu Asp Ser Pro Thr Gly Ile Asp
                       1445                1450                1455
```

```
Phe Ser Asp Ile Thr Ala Asn Ser Phe Thr Val His Trp Ile Ala Pro
            1460                1465                1470
Arg Ala Thr Ile Thr Gly Tyr Arg Ile Arg His His Pro Glu His Phe
            1475                1480                1485
Ser Gly Arg Pro Arg Glu Asp Arg Val Pro His Ser Arg Asn Ser Ile
            1490                1495                1500
Thr Leu Thr Asn Leu Thr Pro Gly Thr Glu Tyr Val Val Ser Ile Val
1505                1510                1515                1520
Ala Leu Asn Gly Arg Glu Glu Ser Pro Leu Leu Ile Gly Gln Gln Ser
            1525                1530                1535
Thr Val Ser Asp Val Pro Arg Asp Leu Glu Val Val Ala Ala Thr Pro
            1540                1545                1550
Thr Ser Leu Leu Ile Ser Trp Asp Ala Pro Ala Val Thr Val Arg Tyr
            1555                1560                1565
Tyr Arg Ile Thr Tyr Gly Glu Thr Gly Gly Asn Ser Pro Val Gln Glu
            1570                1575                1580
Phe Thr Val Pro Gly Ser Lys Ser Thr Ala Thr Ile Ser Gly Leu Lys
1585                1590                1595                1600
Pro Gly Val Asp Tyr Thr Ile Thr Val Tyr Ala Val Thr Gly Arg Gly
            1605                1610                1615
Asp Ser Pro Ala Ser Ser Lys Pro Ile Ser Ile Asn Tyr Arg Thr Glu
            1620                1625                1630
Ile Asp Lys Pro Ser Gln Met Gln Val Thr Asp Val Gln Asp Asn Ser
            1635                1640                1645
Ile Ser Val Lys Trp Leu Pro Ser Ser Ser Pro Val Thr Gly Tyr Arg
            1650                1655                1660
Val Thr Thr Thr Pro Lys Asn Gly Pro Gly Pro Thr Lys Thr Lys Thr
1665                1670                1675                1680
Ala Gly Pro Asp Gln Thr Glu Met Thr Ile Glu Gly Leu Gln Pro Thr
            1685                1690                1695
Val Glu Tyr Val Val Ser Val Tyr Ala Gln Asn Pro Ser Gly Glu Ser
            1700                1705                1710
Gln Pro Leu Val Gln Thr Ala Val Thr Asn Ile Asp Arg Pro Lys Gly
            1715                1720                1725
Leu Ala Phe Thr Asp Val Asp Val Asp Ser Ile Lys Ile Ala Trp Glu
            1730                1735                1740
Ser Pro Gln Gly Gln Val Ser Arg Tyr Arg Val Thr Tyr Ser Ser Pro
1745                1750                1755                1760
Glu Asp Gly Ile His Glu Leu Phe Pro Ala Pro Asp Gly Glu Glu Asp
            1765                1770                1775
Thr Ala Glu Leu Gln Gly Leu Arg Pro Gly Ser Glu Tyr Thr Val Ser
            1780                1785                1790
Val Val Ala Leu His Asp Asp Met Glu Ser Gln Pro Leu Ile Gly Thr
            1795                1800                1805
Gln Ser Thr Ala Ile Pro Ala Pro Thr Asp Leu Lys Phe Thr Gln Val
            1810                1815                1820
Thr Pro Thr Ser Leu Ser Ala Gln Trp Thr Pro Pro Asn Val Gln Leu
1825                1830                1835                1840
Thr Gly Tyr Arg Val Arg Val Thr Pro Lys Glu Lys Thr Gly Pro Met
            1845                1850                1855
Lys Glu Ile Asn Leu Ala Pro Asp Ser Ser Ser Val Val Val Ser Gly
            1860                1865                1870
Leu Met Val Ala Thr Lys Tyr Glu Val Ser Val Tyr Ala Leu Lys Asp
            1875                1880                1885
```

```
Thr Leu Thr Ser Arg Pro Ala Gln Gly Val Val Thr Thr Leu Glu Asn
    1890                1895                1900

Val Ser Pro Pro Arg Arg Ala Arg Val Thr Asp Ala Thr Glu Thr Thr
1905                1910                1915                1920

Ile Thr Ile Ser Trp Arg Thr Lys Thr Glu Thr Ile Thr Gly Phe Gln
                1925                1930                1935

Val Asp Ala Val Pro Ala Asn Gly Gln Thr Pro Ile Gln Arg Thr Ile
            1940                1945                1950

Lys Pro Asp Val Arg Ser Tyr Thr Ile Thr Gly Leu Gln Pro Gly Thr
            1955                1960                1965

Asp Tyr Lys Ile Tyr Leu Tyr Thr Leu Asn Asp Asn Ala Arg Ser Ser
    1970                1975                1980

Pro Val Val Ile Asp Ala Ser Thr Ala Ile Asp Ala Pro Ser Asn Leu
1985                1990                1995                2000

Arg Phe Leu Ala Thr Thr Pro Asn Ser Leu Leu Val Ser Trp Gln Pro
                2005                2010                2015

Pro Arg Ala Arg Ile Thr Gly Tyr Ile Ile Lys Tyr Glu Lys Pro Gly
            2020                2025                2030

Ser Pro Pro Arg Glu Val Val Pro Arg Pro Arg Pro Gly Val Thr Glu
            2035                2040                2045

Ala Thr Ile Thr Gly Leu Glu Pro Gly Thr Glu Tyr Thr Ile Tyr Val
    2050                2055                2060

Ile Ala Leu Lys Asn Asn Gln Lys Ser Glu Pro Leu Ile Gly Arg Lys
2065                2070                2075                2080

Lys Thr Asp Glu Leu Pro Gln Leu Val Thr Leu Pro His Pro Asn Leu
                2085                2090                2095

His Gly Pro Glu Ile Leu Asp Val Pro Ser Thr Val Gln Lys Thr Pro
            2100                2105                2110

Phe Val Thr His Pro Gly Tyr Asp Thr Gly Asn Gly Ile Gln Leu Pro
            2115                2120                2125

Gly Thr Ser Gly Gln Gln Pro Ser Val Gly Gln Gln Met Ile Phe Glu
            2130                2135                2140

Glu His Gly Phe Arg Arg Thr Thr Pro Pro Thr Thr Ala Thr Pro Ile
2145                2150                2155                2160

Arg His Arg Pro Arg Pro Tyr Pro Pro Asn Val Gly Gln Glu Ala Leu
                2165                2170                2175

Ser Gln Thr Thr Ile Ser Trp Ala Pro Phe Gln Asp Thr Ser Glu Tyr
                2180                2185                2190

Ile Ile Ser Cys His Pro Val Gly Thr Asp Glu Glu Pro Leu Gln Phe
            2195                2200                2205

Arg Val Pro Gly Thr Ser Thr Ser Ala Thr Leu Thr Gly Leu Thr Arg
2210                2215                2220

Gly Ala Thr Tyr Asn Ile Ile Val Glu Ala Leu Lys Asp Gln Gln Arg
2225                2230                2235                2240

His Lys Val Arg Glu Glu Val Val Thr Val Gly Asn Ser Val Asn Glu
            2245                2250                2255

Gly Leu Asn Gln Pro Thr Asp Asp Ser Cys Phe Asp Pro Tyr Thr Val
            2260                2265                2270

Ser His Tyr Ala Val Gly Asp Glu Trp Glu Arg Met Ser Glu Ser Gly
        2275                2280                2285

Phe Lys Leu Leu Cys Gln Cys Leu Gly Phe Gly Ser Gly His Phe Arg
        2290                2295                2300

Cys Asp Ser Ser Arg Trp Cys His Asp Asn Gly Val Asn Tyr Lys Ile
```

```
2305                    2310                    2315                    2320
Gly Glu Lys Trp Asp Arg Gln Gly Glu Asn Gly Gln Met Met Ser Cys
                2325                    2330                    2335
Thr Cys Leu Gly Asn Gly Lys Gly Glu Phe Lys Cys Asp Pro His Glu
                2340                    2345                    2350
Ala Thr Cys Tyr Asp Asp Gly Lys Thr Tyr His Val Gly Glu Gln Trp
                2355                    2360                    2365
Gln Lys Glu Tyr Leu Gly Ala Ile Cys Ser Cys Thr Cys Phe Gly Gly
            2370                    2375                    2380
Gln Arg Gly Trp Arg Cys Asp Asn Cys Arg Arg Pro Gly Gly Glu Pro
2385                    2390                    2395                    2400
Ser Pro Glu Gly Thr Thr Gly Gln Ser Tyr Asn Gln Tyr Ser Gln Arg
                2405                    2410                    2415
Tyr His Gln Arg Thr Asn Thr Asn Val Asn Cys Pro Ile Glu Cys Phe
                2420                    2425                    2430
Met Pro Leu Asp Val Gln Ala Asp Arg Glu Asp Ser Arg Glu
                2435                    2440                    2445
```

( 2 ) INFORMATION FOR SEQ ID NO:3:

( i ) SEQUENCE CHARACTERISTICS:
        ( A ) LENGTH: 2179 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 31..1962

( x i ) SEQUENCE DESCRIPTION: SEQ ID NO:3:

```
GTCTAGGAGC CAGCCCCACC CTTAGAAAAG ATG TTT TCC ATG AGG ATC GTC TGC        54
                                 Met Phe Ser Met Arg Ile Val Cys
                                  1               5

CTA GTT CTA AGT GTG GTG GGC ACA GCA TGG ACT GCA GAT AGT GGT GAA        102
Leu Val Leu Ser Val Val Gly Thr Ala Trp Thr Ala Asp Ser Gly Glu
     10              15                  20

GGT GAC TTT CTA GCT GAA GGA GGA GGC GTG CGT GGC CCA AGG GTT GTG        150
Gly Asp Phe Leu Ala Glu Gly Gly Gly Val Arg Gly Pro Arg Val Val
 25              30                  35                      40

GAA AGA CAT CAA TCT GCC TGC AAA GAT TCA GAC TGG CCC TTC TGC TCT        198
Glu Arg His Gln Ser Ala Cys Lys Asp Ser Asp Trp Pro Phe Cys Ser
                 45                  50                  55

GAT GAA GAC TGG AAC TAC AAA TGC CCT TCT GGC TGC AGG ATG AAA GGG        246
Asp Glu Asp Trp Asn Tyr Lys Cys Pro Ser Gly Cys Arg Met Lys Gly
             60                  65                  70

TTG ATT GAT GAA GTC AAT CAA GAT TTT ACA AAC AGA ATA AAT AAG CTC        294
Leu Ile Asp Glu Val Asn Gln Asp Phe Thr Asn Arg Ile Asn Lys Leu
         75                  80                  85

AAA AAT TCA CTA TTT GAA TAT CAG AAG AAC AAT AAG GAT TCT CAT TCG        342
Lys Asn Ser Leu Phe Glu Tyr Gln Lys Asn Asn Lys Asp Ser His Ser
     90                  95                  100

TTG ACC ACT AAT ATA ATG GAA ATT TTG AGA GGC GAT TTT TCC TCA GCC        390
Leu Thr Thr Asn Ile Met Glu Ile Leu Arg Gly Asp Phe Ser Ser Ala
105              110                 115                     120

AAT AAC CGT GAT AAT ACC TAC AAC CGA GTG TCA GAG GAT CTG AGA AGC        438
Asn Asn Arg Asp Asn Thr Tyr Asn Arg Val Ser Glu Asp Leu Arg Ser
                 125                 130                 135

AGA ATT GAA GTC CTG AAG CGC AAA GTC ATA GAA AAA GTA CAG CAT ATC        486
Arg Ile Glu Val Leu Lys Arg Lys Val Ile Glu Lys Val Gln His Ile
             140                 145                 150
```

| | | | | | | | | | | | | | | | | |
|---|---|---|---|---|---|---|---|---|---|---|---|---|---|---|---|---|
| CAG | CTT | CTG | CAG | AAA | AAT | GTT | AGA | GCT | CAG | TTG | GTT | GAT | ATG | AAA | CGA | 534 |
| Gln | Leu | Leu | Gln | Lys | Asn | Val | Arg | Ala | Gln | Leu | Val | Asp | Met | Lys | Arg | |
| | | 155 | | | | 160 | | | | | 165 | | | | | |
| CTG | GAG | GTG | GAC | ATT | GAT | ATT | AAG | ATC | CGA | TCT | TGT | CGA | GGG | TCA | TGG | 582 |
| Leu | Glu | Val | Asp | Ile | Asp | Ile | Lys | Ile | Arg | Ser | Cys | Arg | Gly | Ser | Trp | |
| | 170 | | | | | 175 | | | | | 180 | | | | | |
| AGT | AGG | GCT | TTA | GCT | CGT | GAA | GTA | GAT | CTG | AAG | GAC | TAT | GAA | GAT | CAG | 630 |
| Ser | Arg | Ala | Leu | Ala | Arg | Glu | Val | Asp | Leu | Lys | Asp | Tyr | Glu | Asp | Gln | |
| 185 | | | | | 190 | | | | | 195 | | | | | 200 | |
| CAG | AAG | CAA | CTT | GAA | CAG | GTC | ATT | GCC | AAA | GAC | TTA | CTT | CCC | TCT | AGA | 678 |
| Gln | Lys | Gln | Leu | Glu | Gln | Val | Ile | Ala | Lys | Asp | Leu | Leu | Pro | Ser | Arg | |
| | | | | 205 | | | | | 210 | | | | | 215 | | |
| GAT | AGG | CAA | CAC | TTA | CCA | CTG | ATA | AAA | ATG | AAA | CCA | GTT | CCA | GAC | TTG | 726 |
| Asp | Arg | Gln | His | Leu | Pro | Leu | Ile | Lys | Met | Lys | Pro | Val | Pro | Asp | Leu | |
| | | | 220 | | | | | 225 | | | | | 230 | | | |
| GTT | CCC | GGA | AAT | TTT | AAG | AGC | CAG | CTT | CAG | AAG | GTA | CCC | CCA | GAG | TGG | 774 |
| Val | Pro | Gly | Asn | Phe | Lys | Ser | Gln | Leu | Gln | Lys | Val | Pro | Pro | Glu | Trp | |
| | | 235 | | | | | 240 | | | | | 245 | | | | |
| AAG | GCA | TTA | ACA | GAC | ATG | CCG | CAG | ATG | AGA | ATG | GAG | TTA | GAG | AGA | CCT | 822 |
| Lys | Ala | Leu | Thr | Asp | Met | Pro | Gln | Met | Arg | Met | Glu | Leu | Glu | Arg | Pro | |
| | 250 | | | | | 255 | | | | | 260 | | | | | |
| GGT | GGA | AAT | GAG | ATT | ACT | CGA | GGA | GGC | TCC | ACC | TCT | TAT | GGA | ACC | GGA | 870 |
| Gly | Gly | Asn | Glu | Ile | Thr | Arg | Gly | Gly | Ser | Thr | Ser | Tyr | Gly | Thr | Gly | |
| 265 | | | | | 270 | | | | | 275 | | | | | 280 | |
| TCA | GAG | ACG | GAA | AGC | CCC | AGG | AAC | CCT | AGC | AGT | GCT | GGA | AGC | TGG | AAC | 918 |
| Ser | Glu | Thr | Glu | Ser | Pro | Arg | Asn | Pro | Ser | Ser | Ala | Gly | Ser | Trp | Asn | |
| | | | | 285 | | | | | 290 | | | | | 295 | | |
| TCT | GGG | AGC | TCT | GGA | CCT | GGA | AGT | ACT | GGA | AAC | CGA | AAC | CCT | GGG | AGC | 966 |
| Ser | Gly | Ser | Ser | Gly | Pro | Gly | Ser | Thr | Gly | Asn | Arg | Asn | Pro | Gly | Ser | |
| | | | 300 | | | | | 305 | | | | | 310 | | | |
| TCT | GGG | ACT | GGA | GGG | ACT | GCA | ACC | TGG | AAA | CCT | GGG | AGC | TCT | GGA | CCT | 1014 |
| Ser | Gly | Thr | Gly | Gly | Thr | Ala | Thr | Trp | Lys | Pro | Gly | Ser | Ser | Gly | Pro | |
| | | 315 | | | | | 320 | | | | | 325 | | | | |
| GGA | AGT | GCT | GGA | AGC | TGG | AAC | TCT | GGG | AGC | TCT | GGA | ACT | GGA | AGT | ACT | 1062 |
| Gly | Ser | Ala | Gly | Ser | Trp | Asn | Ser | Gly | Ser | Ser | Gly | Thr | Gly | Ser | Thr | |
| | | 330 | | | | | 335 | | | | | 340 | | | | |
| GGA | AAC | CAA | AAC | CCT | GGA | AGT | CCT | AGA | CCT | GGT | AGT | ACC | GGA | ACC | TGG | 1110 |
| Gly | Asn | Gln | Asn | Pro | Gly | Ser | Pro | Arg | Pro | Gly | Ser | Thr | Gly | Thr | Trp | |
| 345 | | | | | 350 | | | | | 355 | | | | | 360 | |
| AAT | CCT | GGC | AGC | TCT | GAA | CGC | GGA | AGT | GCT | GGG | CAC | TGG | ACC | TCT | GAG | 1158 |
| Asn | Pro | Gly | Ser | Ser | Glu | Arg | Gly | Ser | Ala | Gly | His | Trp | Thr | Ser | Glu | |
| | | | | 365 | | | | | 370 | | | | | 375 | | |
| AGC | TCT | GTA | TCT | GGT | AGT | ACT | GGA | CAA | TGG | CAC | TCT | GAA | TCT | GGA | AGT | 1206 |
| Ser | Ser | Val | Ser | Gly | Ser | Thr | Gly | Gln | Trp | His | Ser | Glu | Ser | Gly | Ser | |
| | | | 380 | | | | | 385 | | | | | 390 | | | |
| TTT | AGG | CCA | GAT | AGC | CCA | GGC | TCT | GGG | AAC | GCG | AGG | CCT | AAC | AAC | CCA | 1254 |
| Phe | Arg | Pro | Asp | Ser | Pro | Gly | Ser | Gly | Asn | Ala | Arg | Pro | Asn | Asn | Pro | |
| | | 395 | | | | | 400 | | | | | 405 | | | | |
| GAC | TGG | GGC | ACA | TTT | GAA | GAG | GTG | TCA | GGA | AAT | GTA | AGT | CCA | GGG | ACA | 1302 |
| Asp | Trp | Gly | Thr | Phe | Glu | Glu | Val | Ser | Gly | Asn | Val | Ser | Pro | Gly | Thr | |
| | 410 | | | | | 415 | | | | | 420 | | | | | |
| AGG | AGA | GAG | TAC | CAC | ACA | GAA | AAA | CTG | GTC | ACT | AAA | GGA | GAT | AAA | GAG | 1350 |
| Arg | Arg | Glu | Tyr | His | Thr | Glu | Lys | Leu | Val | Thr | Lys | Gly | Asp | Lys | Glu | |
| 425 | | | | 430 | | | | | 435 | | | | | | 440 | |
| CTC | AGG | ACT | GGT | AAA | GAG | AAG | GTC | ACC | TCT | GGT | AGC | ACA | ACC | ACC | ACG | 1398 |
| Leu | Arg | Thr | Gly | Lys | Glu | Lys | Val | Thr | Ser | Gly | Ser | Thr | Thr | Thr | Thr | |
| | | | | 445 | | | | 450 | | | | | | 455 | | |
| CGT | CGT | TCA | TGC | TCT | AAA | ACC | GTT | ACT | AAG | ACT | GTT | ATT | GGT | CCT | GAT | 1446 |
| Arg | Arg | Ser | Cys | Ser | Lys | Thr | Val | Thr | Lys | Thr | Val | Ile | Gly | Pro | Asp | |
| | | | 460 | | | | | 465 | | | | | 470 | | | |

-continued

```
GGT  CAC  AAA  GAA  GTT  ACC  AAA  GAA  GTG  GTG  ACC  TCC  GAA  GAT  GGT  TCT    1494
Gly  His  Lys  Glu  Val  Thr  Lys  Glu  Val  Val  Thr  Ser  Glu  Asp  Gly  Ser
          475                     480                          485

GAC  TGT  CCC  GAG  GCA  ATG  GAT  TTA  GGC  ACA  TTG  TCT  GGC  ATA  GGT  ACT    1542
Asp  Cys  Pro  Glu  Ala  Met  Asp  Leu  Gly  Thr  Leu  Ser  Gly  Ile  Gly  Thr
     490                          495                          500

CTG  GAT  GGG  TTC  CGT  CAT  AGG  CAC  CCT  GAT  GAA  GCT  GCC  TTC  TTC  GAC    1590
Leu  Asp  Gly  Phe  Arg  His  Arg  His  Pro  Asp  Glu  Ala  Ala  Phe  Phe  Asp
505                          510                     515                     520

ACT  GCC  TCA  ACT  GGA  AAA  ACA  TTC  CCA  GGT  TTC  TTC  TCA  CCT  ATG  TTA    1638
Thr  Ala  Ser  Thr  Gly  Lys  Thr  Phe  Pro  Gly  Phe  Phe  Ser  Pro  Met  Leu
                    525                     530                     535

GGA  GAG  TTT  GTC  AGT  GAG  ACT  GAG  TCT  AGG  GGC  TCA  GAA  TCT  GGC  ATC    1686
Gly  Glu  Phe  Val  Ser  Glu  Thr  Glu  Ser  Arg  Gly  Ser  Glu  Ser  Gly  Ile
               540                          545                     550

TTC  ACA  AAT  ACA  AAG  GAA  TCC  AGT  TCT  CAT  CAC  CCT  GGG  ATA  GCT  GAA    1734
Phe  Thr  Asn  Thr  Lys  Glu  Ser  Ser  Ser  His  His  Pro  Gly  Ile  Ala  Glu
          555                          560                     565

TTC  CCT  TCC  CGT  GGT  AAA  TCT  TCA  AGT  TAC  AGC  AAA  CAA  TTT  ACT  AGT    1782
Phe  Pro  Ser  Arg  Gly  Lys  Ser  Ser  Ser  Tyr  Ser  Lys  Gln  Phe  Thr  Ser
     570                     575                     580

AGC  ACG  AGT  TAC  AAC  AGA  GGA  GAC  TCC  ACA  TTT  GAA  AGC  AAG  AGC  TAT    1830
Ser  Thr  Ser  Tyr  Asn  Arg  Gly  Asp  Ser  Thr  Phe  Glu  Ser  Lys  Ser  Tyr
585                          590                     595                     600

AAA  ATG  GCA  GAT  GAG  GCC  GGA  AGT  GAA  GCC  GAT  CAT  GAA  GGA  ACA  CAT    1878
Lys  Met  Ala  Asp  Glu  Ala  Gly  Ser  Glu  Ala  Asp  His  Glu  Gly  Thr  His
                    605                     610                     615

AGC  ACC  AAG  AGA  GGG  CAT  GCT  AAA  TCT  CGC  CCT  GTC  AGA  GGT  ATC  CAC    1926
Ser  Thr  Lys  Arg  Gly  His  Ala  Lys  Ser  Arg  Pro  Val  Arg  Gly  Ile  His
               620                     625                     630

ACT  TCT  CCT  TTG  GGG  AAG  CCT  TCC  CTG  TCC  CCC  TAGACTAAGT  TAAATATTTC     1979
Thr  Ser  Pro  Leu  Gly  Lys  Pro  Ser  Leu  Ser  Pro
          635                     640

TGCACAGTGT  TCCCATGGCC  CCTTGCATTT  CCTTCTTAAC  TCTCTGTTAC  ACGTCATTGA            2039

AACTACACTT  TTTTGGTCTG  TTTTTGTGCT  AGACTGTAAG  TTCCTTGGGG  GCAGGGCCTT            2099

TGTCTGTCTC  ATCTCTGTAT  TCCCAAATGC  CTAACAGTAC  AGAGCCATGA  CTCAATAAAT            2159

ACATGTTAAA  TGGATGAATG                                                            2179
```

( 2 ) INFORMATION FOR SEQ ID NO:4:

( i ) SEQUENCE CHARACTERISTICS:
        ( A ) LENGTH: 643 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Phe  Ser  Met  Arg  Ile  Val  Cys  Leu  Val  Leu  Ser  Val  Val  Gly  Thr
 1                    5                     10                          15

Ala  Trp  Thr  Ala  Asp  Ser  Gly  Glu  Gly  Asp  Phe  Leu  Ala  Glu  Gly  Gly
                    20                     25                     30

Gly  Val  Arg  Gly  Pro  Arg  Val  Val  Glu  Arg  His  Gln  Ser  Ala  Cys  Lys
               35                     40                     45

Asp  Ser  Asp  Trp  Pro  Phe  Cys  Ser  Asp  Glu  Asp  Trp  Asn  Tyr  Lys  Cys
     50                     55                     60

Pro  Ser  Gly  Cys  Arg  Met  Lys  Gly  Leu  Ile  Asp  Glu  Val  Asn  Gln  Asp
65                     70                     75                          80
```

```
Phe  Thr  Asn  Arg  Ile  Asn  Lys  Leu  Lys  Asn  Ser  Leu  Phe  Glu  Tyr  Gln
                         85                       90                       95

Lys  Asn  Asn  Lys  Asp  Ser  His  Ser  Leu  Thr  Thr  Asn  Ile  Met  Glu  Ile
               100                      105                     110

Leu  Arg  Gly  Asp  Phe  Ser  Ser  Ala  Asn  Asn  Arg  Asp  Asn  Thr  Tyr  Asn
               115                 120                          125

Arg  Val  Ser  Glu  Asp  Leu  Arg  Ser  Arg  Ile  Glu  Val  Leu  Lys  Arg  Lys
     130                      135                     140

Val  Ile  Glu  Lys  Val  Gln  His  Ile  Gln  Leu  Leu  Gln  Lys  Asn  Val  Arg
145                      150                     155                          160

Ala  Gln  Leu  Val  Asp  Met  Lys  Arg  Leu  Glu  Val  Asp  Ile  Asp  Ile  Lys
                    165                      170                     175

Ile  Arg  Ser  Cys  Arg  Gly  Ser  Trp  Ser  Arg  Ala  Leu  Ala  Arg  Glu  Val
               180                      185                          190

Asp  Leu  Lys  Asp  Tyr  Glu  Asp  Gln  Gln  Lys  Gln  Leu  Glu  Gln  Val  Ile
               195                      200                     205

Ala  Lys  Asp  Leu  Leu  Pro  Ser  Arg  Asp  Arg  Gln  His  Leu  Pro  Leu  Ile
     210                      215                     220

Lys  Met  Lys  Pro  Val  Pro  Asp  Leu  Val  Pro  Gly  Asn  Phe  Lys  Ser  Gln
225                      230                     235                          240

Leu  Gln  Lys  Val  Pro  Pro  Glu  Trp  Lys  Ala  Leu  Thr  Asp  Met  Pro  Gln
                    245                      250                     255

Met  Arg  Met  Glu  Leu  Glu  Arg  Pro  Gly  Gly  Asn  Glu  Ile  Thr  Arg  Gly
               260                      265                     270

Gly  Ser  Thr  Ser  Tyr  Gly  Thr  Gly  Ser  Glu  Thr  Glu  Ser  Pro  Arg  Asn
               275                      280                     285

Pro  Ser  Ser  Ala  Gly  Ser  Trp  Asn  Ser  Gly  Ser  Ser  Gly  Pro  Gly  Ser
     290                      295                     300

Thr  Gly  Asn  Arg  Asn  Pro  Gly  Ser  Ser  Gly  Thr  Gly  Gly  Thr  Ala  Thr
305                      310                     315                          320

Trp  Lys  Pro  Gly  Ser  Ser  Gly  Pro  Gly  Ser  Ala  Gly  Ser  Trp  Asn  Ser
                    325                      330                     335

Gly  Ser  Ser  Gly  Thr  Gly  Ser  Thr  Gly  Asn  Gln  Asn  Pro  Gly  Ser  Pro
               340                      345                     350

Arg  Pro  Gly  Ser  Thr  Gly  Thr  Trp  Asn  Pro  Gly  Ser  Ser  Glu  Arg  Gly
          355                      360                     365

Ser  Ala  Gly  His  Trp  Thr  Ser  Glu  Ser  Ser  Val  Ser  Gly  Ser  Thr  Gly
     370                      375                     380

Gln  Trp  His  Ser  Glu  Ser  Gly  Ser  Phe  Arg  Pro  Asp  Ser  Pro  Gly  Ser
385                      390                     395                          400

Gly  Asn  Ala  Arg  Pro  Asn  Asn  Pro  Asp  Trp  Gly  Thr  Phe  Glu  Glu  Val
               405                      410                     415

Ser  Gly  Asn  Val  Ser  Pro  Gly  Thr  Arg  Arg  Glu  Tyr  His  Thr  Glu  Lys
               420                      425                     430

Leu  Val  Thr  Lys  Gly  Asp  Lys  Glu  Leu  Arg  Thr  Gly  Lys  Glu  Lys  Val
          435                      440                     445

Thr  Ser  Gly  Ser  Thr  Thr  Thr  Thr  Arg  Arg  Ser  Cys  Ser  Lys  Thr  Val
     450                      455                     460

Thr  Lys  Thr  Val  Ile  Gly  Pro  Asp  Gly  His  Lys  Glu  Val  Thr  Lys  Glu
465                      470                     475                          480

Val  Val  Thr  Ser  Glu  Asp  Gly  Ser  Asp  Cys  Pro  Glu  Ala  Met  Asp  Leu
               485                      490                     495

Gly  Thr  Leu  Ser  Gly  Ile  Gly  Thr  Leu  Asp  Gly  Phe  Arg  His  Arg  His
               500                      505                     510
```

```
Pro  Asp  Glu  Ala  Ala  Phe  Phe  Asp  Thr  Ala  Ser  Thr  Gly  Lys  Thr  Phe
          515                      520                     525

Pro  Gly  Phe  Phe  Ser  Pro  Met  Leu  Gly  Glu  Phe  Val  Ser  Glu  Thr  Glu
          530                      535                     540

Ser  Arg  Gly  Ser  Glu  Ser  Gly  Ile  Phe  Thr  Asn  Thr  Lys  Glu  Ser  Ser
545                      550                     555                          560

Ser  His  His  Pro  Gly  Ile  Ala  Glu  Phe  Pro  Ser  Arg  Gly  Lys  Ser  Ser
                    565                      570                     575

Ser  Tyr  Ser  Lys  Gln  Phe  Thr  Ser  Ser  Thr  Ser  Tyr  Asn  Arg  Gly  Asp
               580                      585                     590

Ser  Thr  Phe  Glu  Ser  Lys  Ser  Tyr  Lys  Met  Ala  Asp  Glu  Ala  Gly  Ser
          595                      600                     605

Glu  Ala  Asp  His  Glu  Gly  Thr  His  Ser  Thr  Lys  Arg  Gly  His  Ala  Lys
          610                      615                     620

Ser  Arg  Pro  Val  Arg  Gly  Ile  His  Thr  Ser  Pro  Leu  Gly  Lys  Pro  Ser
625                      630                     635                          640

Leu  Ser  Pro
```

( 2 ) INFORMATION FOR SEQ ID NO:5:

( i ) SEQUENCE CHARACTERISTICS:
        ( A ) LENGTH: 4027 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 3..4013

( x i ) SEQUENCE DESCRIPTION: SEQ ID NO:5:

```
AC  ATG  GCA  GTG  AGT  CAT  GGG  AGG  GAG  AGC  AAG  CCT  CTG  ACT  GCT  CAA        47
    Met  Ala  Val  Ser  His  Gly  Arg  Glu  Ser  Lys  Pro  Leu  Thr  Ala  Gln
    1                   5                        10                       15

CAG  ACA  ACC  AAA  CTG  GAT  GCT  CCC  ACT  AAC  CTC  CAG  TTT  GTC  AAT  GAA        95
Gln  Thr  Thr  Lys  Leu  Asp  Ala  Pro  Thr  Asn  Leu  Gln  Phe  Val  Asn  Glu
                    20                       25                        30

ACT  GAT  TCT  ACT  GTC  CTG  GTG  AGA  TGG  ACT  CCA  CCT  CGG  GCC  CAG  ATA       143
Thr  Asp  Ser  Thr  Val  Leu  Val  Arg  Trp  Thr  Pro  Pro  Arg  Ala  Gln  Ile
               35                       40                        45

ACA  GGA  TAC  CGA  CTG  ACC  GTG  GGC  CTT  ACC  CGA  AGA  GGC  CAG  CCC  AGG       191
Thr  Gly  Tyr  Arg  Leu  Thr  Val  Gly  Leu  Thr  Arg  Arg  Gly  Gln  Pro  Arg
          50                       55                        60

CAG  TAC  AAT  GTG  GGT  CCC  TCT  GTC  TCC  AAG  TAC  CCC  CTG  AGG  AAT  CTG       239
Gln  Tyr  Asn  Val  Gly  Pro  Ser  Val  Ser  Lys  Tyr  Pro  Leu  Arg  Asn  Leu
     65                       70                        75

CAG  CCT  GCA  TCT  GAG  TAC  ACC  GTA  TCC  CTC  GTG  GCC  ATA  AAG  GGC  AAC       287
Gln  Pro  Ala  Ser  Glu  Tyr  Thr  Val  Ser  Leu  Val  Ala  Ile  Lys  Gly  Asn
80                        85                       90                           95

CAA  GAG  AGC  CCC  AAA  GCC  ACT  GGA  GTC  TTT  ACC  ACA  CTG  CAG  CCT  GGG       335
Gln  Glu  Ser  Pro  Lys  Ala  Thr  Gly  Val  Phe  Thr  Thr  Leu  Gln  Pro  Gly
                    100                      105                       110

AGC  TCT  ATT  CCA  CCT  TAC  AAC  ACC  GAG  GTG  ACT  GAG  ACC  ACC  ATC  GTG       383
Ser  Ser  Ile  Pro  Pro  Tyr  Asn  Thr  Glu  Val  Thr  Glu  Thr  Thr  Ile  Val
               115                      120                       125

ATC  ACA  TGG  ACG  CCT  GCT  CCA  AGA  ATT  GGT  TTT  AAG  CTG  GGT  GTA  CGA       431
Ile  Thr  Trp  Thr  Pro  Ala  Pro  Arg  Ile  Gly  Phe  Lys  Leu  Gly  Val  Arg
          130                      135                       140

CCA  AGC  CAG  GGA  GGA  GAG  GCA  CCA  CGA  GAA  GTG  ACT  TCA  GAC  TCA  GGA       479
Pro  Ser  Gln  Gly  Gly  Glu  Ala  Pro  Arg  Glu  Val  Thr  Ser  Asp  Ser  Gly
```

|     |     |     |     |     |     | 145 |     |     |     |     |     | 150 |     |     |     |     |     | 155 |     |     |
|---|---|---|---|---|---|---|---|---|---|---|---|---|---|---|---|---|---|---|---|---|

```
AGC  ATC  GTT  GTG  TCC  GGC  TTG  ACT  CCA  GGA  GTA  GAA  TAC  GTC  TAC  ACC                527
Ser  Ile  Val  Val  Ser  Gly  Leu  Thr  Pro  Gly  Val  Glu  Tyr  Val  Tyr  Thr
160                 165                 170                  175

ATC  CAA  GTC  CTG  AGA  GAT  GGA  CAG  GAA  AGA  GAT  GCG  CCA  ATT  GTA  AAC                575
Ile  Gln  Val  Leu  Arg  Asp  Gly  Gln  Glu  Arg  Asp  Ala  Pro  Ile  Val  Asn
                    180                 185                                 190

AAA  GTG  GTG  ACA  CCA  TTG  TCT  CCA  CCA  ACA  AAC  TTG  CAT  CTG  GAG  GCA                623
Lys  Val  Val  Thr  Pro  Leu  Ser  Pro  Pro  Thr  Asn  Leu  His  Leu  Glu  Ala
               195                      200                           205

AAC  CCT  GAC  ACT  GGA  GTG  CTC  ACA  GTC  TCC  TGG  GAG  AGG  AGC  ACC  ACC                671
Asn  Pro  Asp  Thr  Gly  Val  Leu  Thr  Val  Ser  Trp  Glu  Arg  Ser  Thr  Thr
               210                 215                      220

CCA  GAC  ATT  ACT  GGT  TAT  AGA  ATT  ACC  ACA  ACC  CCT  ACA  AAC  GGC  CAG                719
Pro  Asp  Ile  Thr  Gly  Tyr  Arg  Ile  Thr  Thr  Thr  Pro  Thr  Asn  Gly  Gln
          225                      230                      235

CAG  GGA  AAT  TCT  TTG  GAA  GAA  GTG  GTC  CAT  GCT  GAT  CAG  AGC  TCC  TGC                767
Gln  Gly  Asn  Ser  Leu  Glu  Glu  Val  Val  His  Ala  Asp  Gln  Ser  Ser  Cys
240                      245                      250                      255

ACT  TTT  GAT  AAC  CTG  AGT  CCC  GGC  CTG  GAG  TAC  AAT  GTC  AGT  GTT  TAC                815
Thr  Phe  Asp  Asn  Leu  Ser  Pro  Gly  Leu  Glu  Tyr  Asn  Val  Ser  Val  Tyr
                    260                      265                      270

ACT  GTC  AAG  GAT  GAC  AAG  GAA  AGT  GTC  CCT  ATC  TCT  GAT  ACC  ATC  ATC                863
Thr  Val  Lys  Asp  Asp  Lys  Glu  Ser  Val  Pro  Ile  Ser  Asp  Thr  Ile  Ile
               275                      280                      285

CCA  GAG  GTG  CCC  CAA  CTC  ACT  GAC  CTA  AGC  TTT  GTT  GAT  ATA  ACC  GAT                911
Pro  Glu  Val  Pro  Gln  Leu  Thr  Asp  Leu  Ser  Phe  Val  Asp  Ile  Thr  Asp
          290                      295                      300

TCA  AGC  ATC  GGC  CTG  AGG  TGG  ACC  CCG  CTA  AAC  TCT  TCC  ACC  ATT  ATT                959
Ser  Ser  Ile  Gly  Leu  Arg  Trp  Thr  Pro  Leu  Asn  Ser  Ser  Thr  Ile  Ile
305                      310                      315

GGG  TAC  CGC  ATC  ACA  GTA  GTT  GCG  GCA  GGA  GAA  GGT  ATC  CCT  ATT  TTT               1007
Gly  Tyr  Arg  Ile  Thr  Val  Val  Ala  Ala  Gly  Glu  Gly  Ile  Pro  Ile  Phe
320                      325                      330                      335

GAA  GAT  TTT  GTG  TAC  TCC  TCA  GTA  GGA  TAC  TAC  ACA  GTC  ACA  GGG  CTG               1055
Glu  Asp  Phe  Val  Tyr  Ser  Ser  Val  Gly  Tyr  Tyr  Thr  Val  Thr  Gly  Leu
                    340                      345                      350

GAG  CCG  GGC  ATT  GAC  TAT  GAT  ATC  AGC  GTT  ATC  ACT  CTC  ATT  AAT  GGC               1103
Glu  Pro  Gly  Ile  Asp  Tyr  Asp  Ile  Ser  Val  Ile  Thr  Leu  Ile  Asn  Gly
               355                      360                      365

GGC  GAG  AGT  GCC  CCT  ACT  ACA  CTG  ACA  CAA  CAA  ACG  GCT  GTT  CCT  CCT               1151
Gly  Glu  Ser  Ala  Pro  Thr  Thr  Leu  Thr  Gln  Gln  Thr  Ala  Val  Pro  Pro
          370                      375                      380

CCC  ACT  GAC  CTG  CGA  TTC  ACC  AAC  ATT  GGT  CCA  GAC  ACC  ATG  CGT  GTC               1199
Pro  Thr  Asp  Leu  Arg  Phe  Thr  Asn  Ile  Gly  Pro  Asp  Thr  Met  Arg  Val
385                      390                      395

ACC  TGG  GCT  CCA  CCC  CCA  TCC  ATT  GAT  TTA  ACC  AAC  TTC  CTG  GTG  CGT               1247
Thr  Trp  Ala  Pro  Pro  Pro  Ser  Ile  Asp  Leu  Thr  Asn  Phe  Leu  Val  Arg
400                      405                      410                      415

TAC  TCA  CCT  GTG  AAA  AAT  GAG  GAA  GAT  GTT  GCA  GAG  TTG  TCA  ATT  TCT               1295
Tyr  Ser  Pro  Val  Lys  Asn  Glu  Glu  Asp  Val  Ala  Glu  Leu  Ser  Ile  Ser
                    420                      425                      430

CCT  TCA  GAC  AAT  GCA  GTG  GTC  TTA  ACA  AAT  CTC  CTG  CCT  GGT  ACA  GAA               1343
Pro  Ser  Asp  Asn  Ala  Val  Val  Leu  Thr  Asn  Leu  Leu  Pro  Gly  Thr  Glu
               435                      440                      445

TAT  GTA  GTG  AGT  GTC  TCC  AGT  GTC  TAC  GAA  CAA  CAT  GAG  AGC  ACA  CCT               1391
Tyr  Val  Val  Ser  Val  Ser  Ser  Val  Tyr  Glu  Gln  His  Glu  Ser  Thr  Pro
          450                      455                      460

CTT  AGA  GGA  AGA  CAG  AAA  ACA  GGT  CTT  GAT  TCC  CCA  ACT  GGC  ATT  GAC               1439
Leu  Arg  Gly  Arg  Gln  Lys  Thr  Gly  Leu  Asp  Ser  Pro  Thr  Gly  Ile  Asp
```

-continued

|     |     |     |     | 465 |     |     |     |     | 470 |     |     |     |     | 475 |     |      |
|-----|-----|-----|-----|-----|-----|-----|-----|-----|-----|-----|-----|-----|-----|-----|-----|------|
| TTT | TCT | GAT | ATT | ACT | GCC | AAC | TCT | TTT | ACT | GTG | CAC | TGG | ATT | GCT | CCT | 1487 |
| Phe | Ser | Asp | Ile | Thr | Ala | Asn | Ser | Phe | Thr | Val | His | Trp | Ile | Ala | Pro |      |
| 480 |     |     |     |     | 485 |     |     |     |     | 490 |     |     |     |     | 495 |      |

| CGA | GCC | ACC | ATC | ACT | GGC | TAC | AGG | ATC | CGC | CAT | CAT | CCC | GAG | CAC | TTC | 1535 |
|-----|-----|-----|-----|-----|-----|-----|-----|-----|-----|-----|-----|-----|-----|-----|-----|------|
| Arg | Ala | Thr | Ile | Thr | Gly | Tyr | Arg | Ile | Arg | His | His | Pro | Glu | His | Phe |      |
|     |     |     |     | 500 |     |     |     |     | 505 |     |     |     |     | 510 |     |      |

| AGT | GGG | AGA | CCT | CGA | GAA | GAT | CGG | GTG | CCC | CAC | TCT | CGG | AAT | TCC | ATC | 1583 |
|-----|-----|-----|-----|-----|-----|-----|-----|-----|-----|-----|-----|-----|-----|-----|-----|------|
| Ser | Gly | Arg | Pro | Arg | Glu | Asp | Arg | Val | Pro | His | Ser | Arg | Asn | Ser | Ile |      |
|     |     |     | 515 |     |     |     |     | 520 |     |     |     |     | 525 |     |     |      |

| ACC | CTC | ACC | AAC | CTC | ACT | CCA | GGC | ACA | GAG | TAT | GTG | GTC | AGC | ATC | GTT | 1631 |
|-----|-----|-----|-----|-----|-----|-----|-----|-----|-----|-----|-----|-----|-----|-----|-----|------|
| Thr | Leu | Thr | Asn | Leu | Thr | Pro | Gly | Thr | Glu | Tyr | Val | Val | Ser | Ile | Val |      |
|     |     | 530 |     |     |     |     | 535 |     |     |     |     | 540 |     |     |     |      |

| GCT | CTT | AAT | GGC | AGA | GAG | GAA | AGT | CCC | TTA | TTG | ATT | GGC | CAA | CAA | TCA | 1679 |
|-----|-----|-----|-----|-----|-----|-----|-----|-----|-----|-----|-----|-----|-----|-----|-----|------|
| Ala | Leu | Asn | Gly | Arg | Glu | Glu | Ser | Pro | Leu | Leu | Ile | Gly | Gln | Gln | Ser |      |
|     | 545 |     |     |     |     | 550 |     |     |     |     | 555 |     |     |     |     |      |

| ACA | GTT | TCT | GAT | GTT | CCG | AGG | GAC | CTG | GAA | GTT | GTT | GCT | GCG | ACC | CCC | 1727 |
|-----|-----|-----|-----|-----|-----|-----|-----|-----|-----|-----|-----|-----|-----|-----|-----|------|
| Thr | Val | Ser | Asp | Val | Pro | Arg | Asp | Leu | Glu | Val | Val | Ala | Ala | Thr | Pro |      |
| 560 |     |     |     |     | 565 |     |     |     |     | 570 |     |     |     |     | 575 |      |

| ACC | AGC | CTA | CTG | ATC | AGC | TGG | GAT | GCT | CCT | GCT | GTC | ACA | GTG | AGA | TAT | 1775 |
|-----|-----|-----|-----|-----|-----|-----|-----|-----|-----|-----|-----|-----|-----|-----|-----|------|
| Thr | Ser | Leu | Leu | Ile | Ser | Trp | Asp | Ala | Pro | Ala | Val | Thr | Val | Arg | Tyr |      |
|     |     |     |     | 580 |     |     |     |     | 585 |     |     |     |     | 590 |     |      |

| TAC | AGG | ATC | ACT | TAC | GGA | GAA | ACA | GGA | GGA | AAT | AGC | CCT | GTC | CAG | GAG | 1823 |
|-----|-----|-----|-----|-----|-----|-----|-----|-----|-----|-----|-----|-----|-----|-----|-----|------|
| Tyr | Arg | Ile | Thr | Tyr | Gly | Glu | Thr | Gly | Gly | Asn | Ser | Pro | Val | Gln | Glu |      |
|     |     |     | 595 |     |     |     |     | 600 |     |     |     |     | 605 |     |     |      |

| TTC | ACT | GTG | CCT | GGG | AGC | AAG | TCT | ACA | GCT | ACC | ATC | AGC | GGC | CTT | AAA | 1871 |
|-----|-----|-----|-----|-----|-----|-----|-----|-----|-----|-----|-----|-----|-----|-----|-----|------|
| Phe | Thr | Val | Pro | Gly | Ser | Lys | Ser | Thr | Ala | Thr | Ile | Ser | Gly | Leu | Lys |      |
|     |     | 610 |     |     |     |     | 615 |     |     |     |     | 620 |     |     |     |      |

| CCT | GGA | GTT | GAT | TAT | ACC | ATC | ACT | GTG | TAT | GCT | GTC | ACT | GGC | CGT | GGA | 1919 |
|-----|-----|-----|-----|-----|-----|-----|-----|-----|-----|-----|-----|-----|-----|-----|-----|------|
| Pro | Gly | Val | Asp | Tyr | Thr | Ile | Thr | Val | Tyr | Ala | Val | Thr | Gly | Arg | Gly |      |
|     | 625 |     |     |     |     | 630 |     |     |     |     | 635 |     |     |     |     |      |

| GAC | AGC | CCC | GCA | AGC | AGC | AAG | CCA | ATT | TCC | ATT | AAT | TAC | CGA | ACA | GAA | 1967 |
|-----|-----|-----|-----|-----|-----|-----|-----|-----|-----|-----|-----|-----|-----|-----|-----|------|
| Asp | Ser | Pro | Ala | Ser | Ser | Lys | Pro | Ile | Ser | Ile | Asn | Tyr | Arg | Thr | Glu |      |
| 640 |     |     |     |     | 645 |     |     |     |     | 650 |     |     |     |     | 655 |      |

| ATT | GAC | AAA | CCA | TCC | CAG | ATG | CAA | GTG | ACC | GAT | GTT | CAG | GAC | AAC | AGC | 2015 |
|-----|-----|-----|-----|-----|-----|-----|-----|-----|-----|-----|-----|-----|-----|-----|-----|------|
| Ile | Asp | Lys | Pro | Ser | Gln | Met | Gln | Val | Thr | Asp | Val | Gln | Asp | Asn | Ser |      |
|     |     |     |     | 660 |     |     |     |     | 665 |     |     |     |     | 670 |     |      |

| ATT | AGT | GTC | AAG | TGG | CTG | CCT | TCA | AGT | TCC | CCT | GTT | ACT | GGT | TAC | AGA | 2063 |
|-----|-----|-----|-----|-----|-----|-----|-----|-----|-----|-----|-----|-----|-----|-----|-----|------|
| Ile | Ser | Val | Lys | Trp | Leu | Pro | Ser | Ser | Ser | Pro | Val | Thr | Gly | Tyr | Arg |      |
|     |     |     | 675 |     |     |     |     | 680 |     |     |     |     | 685 |     |     |      |

| GTA | ACC | ACC | ACT | CCC | AAA | AAT | GGA | CCA | GGA | CCA | ACA | AAA | ACT | AAA | ACT | 2111 |
|-----|-----|-----|-----|-----|-----|-----|-----|-----|-----|-----|-----|-----|-----|-----|-----|------|
| Val | Thr | Thr | Thr | Pro | Lys | Asn | Gly | Pro | Gly | Pro | Thr | Lys | Thr | Lys | Thr |      |
|     |     |     | 690 |     |     |     |     | 695 |     |     |     |     | 700 |     |     |      |

| GCA | GGT | CCA | GAT | CAA | ACA | GAA | ATG | ACT | ATT | GAA | GGC | TTG | CAG | CCC | ACA | 2159 |
|-----|-----|-----|-----|-----|-----|-----|-----|-----|-----|-----|-----|-----|-----|-----|-----|------|
| Ala | Gly | Pro | Asp | Gln | Thr | Glu | Met | Thr | Ile | Glu | Gly | Leu | Gln | Pro | Thr |      |
|     | 705 |     |     |     |     | 710 |     |     |     |     | 715 |     |     |     |     |      |

| GTG | GAG | TAT | GTG | GTT | AGT | GTC | TAT | GCT | CAG | AAT | CCA | AGC | GGA | GAG | AGT | 2207 |
|-----|-----|-----|-----|-----|-----|-----|-----|-----|-----|-----|-----|-----|-----|-----|-----|------|
| Val | Glu | Tyr | Val | Val | Ser | Val | Tyr | Ala | Gln | Asn | Pro | Ser | Gly | Glu | Ser |      |
| 720 |     |     |     |     | 725 |     |     |     |     | 730 |     |     |     |     | 735 |      |

| CAG | CCT | CTG | GTT | CAG | ACT | GCA | GTA | ACC | AAC | ATT | GAT | CGC | CCT | AAA | GGA | 2255 |
|-----|-----|-----|-----|-----|-----|-----|-----|-----|-----|-----|-----|-----|-----|-----|-----|------|
| Gln | Pro | Leu | Val | Gln | Thr | Ala | Val | Thr | Asn | Ile | Asp | Arg | Pro | Lys | Gly |      |
|     |     |     |     | 740 |     |     |     |     | 745 |     |     |     |     | 750 |     |      |

| CTG | GCA | TTC | ACT | GAT | GTG | GAT | GTC | GAT | TCC | ATC | AAA | ATT | GCT | TGG | GAA | 2303 |
|-----|-----|-----|-----|-----|-----|-----|-----|-----|-----|-----|-----|-----|-----|-----|-----|------|
| Leu | Ala | Phe | Thr | Asp | Val | Asp | Val | Asp | Ser | Ile | Lys | Ile | Ala | Trp | Glu |      |
|     |     |     | 755 |     |     |     |     | 760 |     |     |     |     | 765 |     |     |      |

| AGC | CCA | CAG | GGG | CAA | GTT | TCC | AGG | TAC | AGG | GTG | ACC | TAC | TCG | AGC | CCT | 2351 |
|-----|-----|-----|-----|-----|-----|-----|-----|-----|-----|-----|-----|-----|-----|-----|-----|------|
| Ser | Pro | Gln | Gly | Gln | Val | Ser | Arg | Tyr | Arg | Val | Thr | Tyr | Ser | Ser | Pro |      |
|     |     |     | 770 |     |     |     |     | 775 |     |     |     |     | 780 |     |     |      |

| GAG | GAT | GGA | ATC | CAT | GAG | CTA | TTC | CCT | GCA | CCT | GAT | GGT | GAA | GAA | GAC | 2399 |
|-----|-----|-----|-----|-----|-----|-----|-----|-----|-----|-----|-----|-----|-----|-----|-----|------|
| Glu | Asp | Gly | Ile | His | Glu | Leu | Phe | Pro | Ala | Pro | Asp | Gly | Glu | Glu | Asp |      |

|  |  |  |  |  |  |  |  |  |  |  |  |  |  |  |  |  |
|---|---|---|---|---|---|---|---|---|---|---|---|---|---|---|---|---|
| | 785 | | | | | 790 | | | | | 795 | | | | | |
| ACT | GCA | GAG | CTG | CAA | GGC | CTC | AGA | CCG | GGT | TCT | GAG | TAC | ACA | GTC | AGT | 2447 |
| Thr | Ala | Glu | Leu | Gln | Gly | Leu | Arg | Pro | Gly | Ser | Glu | Tyr | Thr | Val | Ser | |
| 800 | | | | | 805 | | | | | 810 | | | | | 815 | |
| GTG | GTT | GCC | TTG | CAC | GAT | GAT | ATG | GAG | AGC | CAG | CCC | CTG | ATT | GGA | ACC | 2495 |
| Val | Val | Ala | Leu | His | Asp | Asp | Met | Glu | Ser | Gln | Pro | Leu | Ile | Gly | Thr | |
| | | | | 820 | | | | | 825 | | | | | 830 | | |
| CAG | TCC | ACA | GCT | ATT | CCT | GCA | CCA | ACT | GAC | CTG | AAG | TTC | ACT | CAG | GTC | 2543 |
| Gln | Ser | Thr | Ala | Ile | Pro | Ala | Pro | Thr | Asp | Leu | Lys | Phe | Thr | Gln | Val | |
| | | | 835 | | | | | 840 | | | | | 845 | | | |
| ACA | CCC | ACA | AGC | CTG | AGC | GCC | CAG | TGG | ACA | CCA | CCC | AAT | GTT | CAG | CTC | 2591 |
| Thr | Pro | Thr | Ser | Leu | Ser | Ala | Gln | Trp | Thr | Pro | Pro | Asn | Val | Gln | Leu | |
| | | 850 | | | | | 855 | | | | | 860 | | | | |
| ACT | GGA | TAT | CGA | GTG | CGG | GTG | ACC | CCC | AAG | GAG | AAG | ACC | GGA | CCA | ATG | 2639 |
| Thr | Gly | Tyr | Arg | Val | Arg | Val | Thr | Pro | Lys | Glu | Lys | Thr | Gly | Pro | Met | |
| 865 | | | | | 870 | | | | | 875 | | | | | | |
| AAA | GAA | ATC | AAC | CTT | GCT | CCT | GAC | AGC | TCA | TCC | GTG | GTT | GTA | TCA | GGA | 2687 |
| Lys | Glu | Ile | Asn | Leu | Ala | Pro | Asp | Ser | Ser | Ser | Val | Val | Val | Ser | Gly | |
| 880 | | | | | 885 | | | | | 890 | | | | | 895 | |
| CTT | ATG | GTG | GCC | ACC | AAA | TAT | GAA | GTG | AGT | GTC | TAT | GCT | CTT | AAG | GAC | 2735 |
| Leu | Met | Val | Ala | Thr | Lys | Tyr | Glu | Val | Ser | Val | Tyr | Ala | Leu | Lys | Asp | |
| | | | | 900 | | | | | 905 | | | | | 910 | | |
| ACT | TTG | ACA | AGC | AGA | CCA | GCT | CAG | GGT | GTT | GTC | ACC | ACT | CTG | GAG | GGA | 2783 |
| Thr | Leu | Thr | Ser | Arg | Pro | Ala | Gln | Gly | Val | Val | Thr | Thr | Leu | Glu | Gly | |
| | | | 915 | | | | | 920 | | | | | 925 | | | |
| GGA | AAT | TTT | AAG | AGC | CAG | CTT | CAG | AAG | GTA | CCC | CCA | GAG | TGG | AAG | GCA | 2831 |
| Gly | Asn | Phe | Lys | Ser | Gln | Leu | Gln | Lys | Val | Pro | Pro | Glu | Trp | Lys | Ala | |
| | | 930 | | | | | 935 | | | | | 940 | | | | |
| TTA | ACA | GAC | ATG | CCG | CAG | ATG | AGA | ATG | GAG | TTA | GAG | AGA | CCT | GGT | GGA | 2879 |
| Leu | Thr | Asp | Met | Pro | Gln | Met | Arg | Met | Glu | Leu | Glu | Arg | Pro | Gly | Gly | |
| | 945 | | | | | 950 | | | | | 955 | | | | | |
| AAT | GAG | ATT | ACT | CGA | GGA | GGC | TCC | ACC | TCT | TAT | GGA | ACC | GGA | TCA | GAG | 2927 |
| Asn | Glu | Ile | Thr | Arg | Gly | Gly | Ser | Thr | Ser | Tyr | Gly | Thr | Gly | Ser | Glu | |
| 960 | | | | | 965 | | | | | 970 | | | | | 975 | |
| ACG | GAA | AGC | CCC | AGG | AAC | CCT | AGC | AGT | GCT | GGA | AGC | TGG | AAC | TCT | GGG | 2975 |
| Thr | Glu | Ser | Pro | Arg | Asn | Pro | Ser | Ser | Ala | Gly | Ser | Trp | Asn | Ser | Gly | |
| | | | | 980 | | | | | 985 | | | | | 990 | | |
| AGC | TCT | GGA | CCT | GGA | AGT | ACT | GGA | AAC | CGA | AAC | CCT | GGG | AGC | TCT | GGG | 3023 |
| Ser | Ser | Gly | Pro | Gly | Ser | Thr | Gly | Asn | Arg | Asn | Pro | Gly | Ser | Ser | Gly | |
| | | | 995 | | | | | 1000 | | | | | 1005 | | | |
| ACT | GGA | GGG | ACT | GCA | ACC | TGG | AAA | CCT | GGG | AGC | TCT | GGA | CCT | GGA | AGT | 3071 |
| Thr | Gly | Gly | Thr | Ala | Thr | Trp | Lys | Pro | Gly | Ser | Ser | Gly | Pro | Gly | Ser | |
| | | 1010 | | | | | 1015 | | | | | 1020 | | | | |
| GCT | GGA | AGC | TGG | AAC | TCT | GGG | AGC | TCT | GGA | ACT | GGA | AGT | ACT | GGA | AAC | 3119 |
| Ala | Gly | Ser | Trp | Asn | Ser | Gly | Ser | Ser | Gly | Thr | Gly | Ser | Thr | Gly | Asn | |
| | 1025 | | | | | 1030 | | | | | 1035 | | | | | |
| CAA | AAC | CCT | GGG | AGC | CCT | AGA | CCT | GGT | AGT | ACC | GGA | ACC | TGG | AAT | CCT | 3167 |
| Gln | Asn | Pro | Gly | Ser | Pro | Arg | Pro | Gly | Ser | Thr | Gly | Thr | Trp | Asn | Pro | |
| 1040 | | | | | 1045 | | | | | 1050 | | | | | 1055 | |
| GGC | AGC | TCT | GAA | CGC | GGA | AGT | GCT | GGG | CAC | TGG | ACC | TCT | GAG | AGC | TCT | 3215 |
| Gly | Ser | Ser | Glu | Arg | Gly | Ser | Ala | Gly | His | Trp | Thr | Ser | Glu | Ser | Ser | |
| | | | | 1060 | | | | | 1065 | | | | | 1070 | | |
| GTA | TCT | GGT | AGT | ACT | GGA | CAA | TGG | CAC | TCT | GAA | TCT | GGA | AGT | TTT | AGG | 3263 |
| Val | Ser | Gly | Ser | Thr | Gly | Gln | Trp | His | Ser | Glu | Ser | Gly | Ser | Phe | Arg | |
| | | | 1075 | | | | | 1080 | | | | | 1085 | | | |
| CCA | GAT | AGC | CCA | GGC | TCT | GGG | AAC | GCG | AGG | CCT | AAC | AAC | CCA | GAC | TGG | 3311 |
| Pro | Asp | Ser | Pro | Gly | Ser | Gly | Asn | Ala | Arg | Pro | Asn | Asn | Pro | Asp | Trp | |
| | | | 1090 | | | | | 1095 | | | | | 1100 | | | |
| GGC | ACA | TTT | GAA | GAG | GTG | TCA | GGA | AAT | GTA | AGT | CCA | GGG | ACA | AGG | AGA | 3359 |
| Gly | Thr | Phe | Glu | Glu | Val | Ser | Gly | Asn | Val | Ser | Pro | Gly | Thr | Arg | Arg | |

|     |     |     |     |     |     |     |     |     |     |     |     |     |     |     |     |      |
|---|---|---|---|---|---|---|---|---|---|---|---|---|---|---|---|---|
|     |     | 1105 |     |     |     | 1110 |     |     |     |     | 1115 |     |     |     |     |      |
| GAG | TAC | CAC | ACA | GAA | AAA | CTG | GTC | ACT | AAA | GGA | GAT | AAA | GAG | CTC | AGG | 3407 |
| Glu | Tyr | His | Thr | Glu | Lys | Leu | Val | Thr | Lys | Gly | Asp | Lys | Glu | Leu | Arg |      |
| 1120 |     |     |     | 1125 |     |     |     |     | 1130 |     |     |     |     |     | 1135 |      |
| ACT | GGT | AAA | GAG | AAG | GTC | ACC | TCT | GGT | AGC | ACA | ACC | ACC | ACG | CGT | CGT | 3455 |
| Thr | Gly | Lys | Glu | Lys | Val | Thr | Ser | Gly | Ser | Thr | Thr | Thr | Thr | Arg | Arg |      |
|     |     |     |     |     | 1140 |     |     |     |     | 1145 |     |     |     |     | 1150 |      |
| TCA | TGC | TCT | AAA | ACC | GTT | ACT | AAG | ACT | GTT | ATT | GGT | CCT | GAT | GGT | CAC | 3503 |
| Ser | Cys | Ser | Lys | Thr | Val | Thr | Lys | Thr | Val | Ile | Gly | Pro | Asp | Gly | His |      |
|     |     |     |     | 1155 |     |     |     |     | 1160 |     |     |     |     | 1165 |     |      |
| AAA | GAA | GTT | ACC | AAA | GAA | GTG | GTG | ACC | TCC | GAA | GAT | GGT | TCT | GAC | TGT | 3551 |
| Lys | Glu | Val | Thr | Lys | Glu | Val | Val | Thr | Ser | Glu | Asp | Gly | Ser | Asp | Cys |      |
|     |     |     | 1170 |     |     |     |     | 1175 |     |     |     |     | 1180 |     |     |      |
| CCC | GAG | GCA | ATG | GAT | TTA | GGC | ACA | TTG | TCT | GGC | ATA | GGT | ACT | CTG | GAT | 3599 |
| Pro | Glu | Ala | Met | Asp | Leu | Gly | Thr | Leu | Ser | Gly | Ile | Gly | Thr | Leu | Asp |      |
|     |     | 1185 |     |     |     |     | 1190 |     |     |     |     |     | 1195 |     |     |      |
| GGG | TTC | CGC | CAT | AGG | CAC | CCT | GAT | GAA | GCT | GCC | TTC | TTC | GAC | ACT | GCC | 3647 |
| Gly | Phe | Arg | His | Arg | His | Pro | Asp | Glu | Ala | Ala | Phe | Phe | Asp | Thr | Ala |      |
| 1200 |     |     |     |     | 1205 |     |     |     |     | 1210 |     |     |     |     | 1215 |      |
| TCA | ACT | GGA | AAA | ACA | TTC | CCA | GGT | TTC | TTC | TCA | CCT | ATG | TTA | GGA | GAG | 3695 |
| Ser | Thr | Gly | Lys | Thr | Phe | Pro | Gly | Phe | Phe | Ser | Pro | Met | Leu | Gly | Glu |      |
|     |     |     |     | 1220 |     |     |     |     | 1225 |     |     |     |     | 1230 |     |      |
| TTT | GTC | AGT | GAG | ACT | GAG | TCT | AGG | GGC | TCA | GAA | TCT | GGC | ATC | TTC | ACA | 3743 |
| Phe | Val | Ser | Glu | Thr | Glu | Ser | Arg | Gly | Ser | Glu | Ser | Gly | Ile | Phe | Thr |      |
|     |     |     | 1235 |     |     |     |     | 1240 |     |     |     |     | 1245 |     |     |      |
| AAT | ACA | AAG | GAA | TCC | AGT | TCT | CAT | CAC | CCT | GGG | ATA | GCT | GAA | TTC | CCT | 3791 |
| Asn | Thr | Lys | Glu | Ser | Ser | Ser | His | His | Pro | Gly | Ile | Ala | Glu | Phe | Pro |      |
|     |     |     | 1250 |     |     |     |     | 1255 |     |     |     |     | 1260 |     |     |      |
| TCC | CGT | GGT | AAA | TCT | TCA | AGT | TAC | AGC | AAA | CAA | TTT | ACT | AGT | AGC | ACG | 3839 |
| Ser | Arg | Gly | Lys | Ser | Ser | Ser | Tyr | Ser | Lys | Gln | Phe | Thr | Ser | Ser | Thr |      |
|     | 1265 |     |     |     |     | 1270 |     |     |     |     | 1275 |     |     |     |     |      |
| AGT | TAC | AAC | AGA | GGA | GAC | TCC | ACA | TTT | GAA | AGC | AAG | AGC | TAT | AAA | ATG | 3887 |
| Ser | Tyr | Asn | Arg | Gly | Asp | Ser | Thr | Phe | Glu | Ser | Lys | Ser | Tyr | Lys | Met |      |
| 1280 |     |     |     |     | 1285 |     |     |     |     | 1290 |     |     |     |     | 1295 |      |
| GCA | GAT | GAG | GCC | GGA | AGT | GAA | GCC | GAT | CAT | GAA | GGA | ACA | CAT | AGC | ACC | 3935 |
| Ala | Asp | Glu | Ala | Gly | Ser | Glu | Ala | Asp | His | Glu | Gly | Thr | His | Ser | Thr |      |
|     |     |     |     | 1300 |     |     |     |     | 1305 |     |     |     |     | 1310 |     |      |
| AAG | AGA | GGC | CAT | GCT | AAA | TCT | CGC | CCT | GTC | AGA | GGT | ATC | CAC | ACT | TCT | 3983 |
| Lys | Arg | Gly | His | Ala | Lys | Ser | Arg | Pro | Val | Arg | Gly | Ile | His | Thr | Ser |      |
|     |     |     | 1315 |     |     |     |     | 1320 |     |     |     |     | 1325 |     |     |      |
| CCT | TTG | GGG | AAG | CCT | TCC | CTG | TCC | CCC | TAGACTAAGT | TAAATAT |     |     |     |     |     | 4027 |
| Pro | Leu | Gly | Lys | Pro | Ser | Leu | Ser | Pro |     |     |     |     |     |     |     |      |
|     |     |     | 1330 |     |     |     | 1335 |     |     |     |     |     |     |     |     |      |

( 2 ) INFORMATION FOR SEQ ID NO:6:

( i ) SEQUENCE CHARACTERISTICS:
        ( A ) LENGTH: 1336 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|     |     |     |     |     |     |     |     |     |     |     |     |     |     |     |
|---|---|---|---|---|---|---|---|---|---|---|---|---|---|---|
| Met | Ala | Val | Ser | His | Gly | Arg | Glu | Ser | Lys | Pro | Leu | Thr | Ala | Gln |
| 1   |     |     |     | 5   |     |     |     |     | 10  |     |     |     |     | 15  |
| Gln | Thr | Thr | Lys | Leu | Asp | Ala | Pro | Thr | Asn | Leu | Gln | Phe | Val | Asn | Glu | Thr |
|     |     |     |     | 20  |     |     |     |     | 25  |     |     |     |     | 30  |     |     |
| Asp | Ser | Thr | Val | Leu | Val | Arg | Trp | Thr | Pro | Pro | Arg | Ala | Gln | Ile | Thr |
|     |     |     | 35  |     |     |     |     | 40  |     |     |     |     | 45  |     |     |
| Gly | Tyr | Arg | Leu | Thr | Val | Gly | Leu | Thr | Arg | Arg | Gly | Gln | Pro | Arg | Gln |

-continued

```
            50                          55                          60

Tyr Asn Val Gly Pro Ser Val Ser Lys Tyr Pro Leu Arg Asn Leu Gln
 65              70                  75                       80

Pro Ala Ser Glu Tyr Thr Val Ser Leu Val Ala Ile Lys Gly Asn Gln
             85                  90                       95

Glu Ser Pro Lys Ala Thr Gly Val Phe Thr Thr Leu Gln Pro Gly Ser
            100                 105                      110

Ser Ile Pro Pro Tyr Asn Thr Glu Val Thr Glu Thr Thr Ile Val Ile
        115                 120                 125

Thr Trp Thr Pro Ala Pro Arg Ile Gly Phe Lys Leu Gly Val Arg Pro
    130                 135                 140

Ser Gln Gly Gly Glu Ala Pro Arg Glu Val Thr Ser Asp Ser Gly Ser
145                 150                 155                 160

Ile Val Val Ser Gly Leu Thr Pro Gly Val Glu Tyr Val Tyr Thr Ile
                165                 170                 175

Gln Val Leu Arg Asp Gly Gln Glu Arg Asp Ala Pro Ile Val Asn Lys
            180                 185                 190

Val Val Thr Pro Leu Ser Pro Pro Thr Asn Leu His Leu Glu Ala Asn
        195                 200                 205

Pro Asp Thr Gly Val Leu Thr Val Ser Trp Glu Arg Ser Thr Thr Pro
    210                 215                 220

Asp Ile Thr Gly Tyr Arg Ile Thr Thr Thr Pro Thr Asn Gly Gln Gln
225                 230                 235                 240

Gly Asn Ser Leu Glu Glu Val Val His Ala Asp Gln Ser Ser Cys Thr
                245                 250                 255

Phe Asp Asn Leu Ser Pro Gly Leu Glu Tyr Asn Val Ser Val Tyr Thr
            260                 265                 270

Val Lys Asp Asp Lys Glu Ser Val Pro Ile Ser Asp Thr Ile Ile Pro
        275                 280                 285

Glu Val Pro Gln Leu Thr Asp Leu Ser Phe Val Asp Ile Thr Asp Ser
    290                 295                 300

Ser Ile Gly Leu Arg Trp Thr Pro Leu Asn Ser Ser Thr Ile Ile Gly
305                 310                 315                 320

Tyr Arg Ile Thr Val Val Ala Ala Gly Glu Gly Ile Pro Ile Phe Glu
                325                 330                 335

Asp Phe Val Tyr Ser Ser Val Gly Tyr Tyr Thr Val Thr Gly Leu Glu
            340                 345                 350

Pro Gly Ile Asp Tyr Asp Ile Ser Val Ile Thr Leu Ile Asn Gly Gly
        355                 360                 365

Glu Ser Ala Pro Thr Thr Leu Thr Gln Gln Thr Ala Val Pro Pro Pro
    370                 375                 380

Thr Asp Leu Arg Phe Thr Asn Ile Gly Pro Asp Thr Met Arg Val Thr
385                 390                 395                 400

Trp Ala Pro Pro Pro Ser Ile Asp Leu Thr Asn Phe Leu Val Arg Tyr
                405                 410                 415

Ser Pro Val Lys Asn Glu Glu Asp Val Ala Glu Leu Ser Ile Ser Pro
            420                 425                 430

Ser Asp Asn Ala Val Val Leu Thr Asn Leu Leu Pro Gly Thr Glu Tyr
        435                 440                 445

Val Val Ser Val Ser Ser Val Tyr Glu Gln His Glu Ser Thr Pro Leu
    450                 455                 460

Arg Gly Arg Gln Lys Thr Gly Leu Asp Ser Pro Thr Gly Ile Asp Phe
465                 470                 475                 480
```

```
Ser  Asp  Ile  Thr  Ala  Asn  Ser  Phe  Thr  Val  His  Trp  Ile  Ala  Pro  Arg
               485                     490                     495

Ala  Thr  Ile  Thr  Gly  Tyr  Arg  Ile  Arg  His  His  Pro  Glu  His  Phe  Ser
               500                     505                     510

Gly  Arg  Pro  Arg  Glu  Asp  Arg  Val  Pro  His  Ser  Arg  Asn  Ser  Ile  Thr
               515                     520                     525

Leu  Thr  Asn  Leu  Thr  Pro  Gly  Thr  Glu  Tyr  Val  Val  Ser  Ile  Val  Ala
     530                         535                     540

Leu  Asn  Gly  Arg  Glu  Glu  Ser  Pro  Leu  Leu  Ile  Gly  Gln  Gln  Ser  Thr
545                      550                     555                     560

Val  Ser  Asp  Val  Pro  Arg  Asp  Leu  Glu  Val  Val  Ala  Ala  Thr  Pro  Thr
               565                     570                     575

Ser  Leu  Leu  Ile  Ser  Trp  Asp  Ala  Pro  Ala  Val  Thr  Val  Arg  Tyr  Tyr
               580                     585                     590

Arg  Ile  Thr  Tyr  Gly  Glu  Thr  Gly  Gly  Asn  Ser  Pro  Val  Gln  Glu  Phe
               595                     600                     605

Thr  Val  Pro  Gly  Ser  Lys  Ser  Thr  Ala  Thr  Ile  Ser  Gly  Leu  Lys  Pro
     610                         615                     620

Gly  Val  Asp  Tyr  Thr  Ile  Thr  Val  Tyr  Ala  Val  Thr  Gly  Arg  Gly  Asp
625                      630                     635                     640

Ser  Pro  Ala  Ser  Ser  Lys  Pro  Ile  Ser  Ile  Asn  Tyr  Arg  Thr  Glu  Ile
                    645                     650                     655

Asp  Lys  Pro  Ser  Gln  Met  Gln  Val  Thr  Asp  Val  Gln  Asp  Asn  Ser  Ile
                    660                     665                     670

Ser  Val  Lys  Trp  Leu  Pro  Ser  Ser  Pro  Val  Thr  Gly  Tyr  Arg  Val
          675                     680                     685

Thr  Thr  Thr  Pro  Lys  Asn  Gly  Pro  Gly  Pro  Thr  Lys  Thr  Lys  Thr  Ala
     690                         695                     700

Gly  Pro  Asp  Gln  Thr  Glu  Met  Thr  Ile  Glu  Gly  Leu  Gln  Pro  Thr  Val
705                           710                    715                    720

Glu  Tyr  Val  Val  Ser  Val  Tyr  Ala  Gln  Asn  Pro  Ser  Gly  Glu  Ser  Gln
                    725                     730                     735

Pro  Leu  Val  Gln  Thr  Ala  Val  Thr  Asn  Ile  Asp  Arg  Pro  Lys  Gly  Leu
               740                     745                     750

Ala  Phe  Thr  Asp  Val  Asp  Val  Asp  Ser  Ile  Lys  Ile  Ala  Trp  Glu  Ser
          755                          760                     765

Pro  Gln  Gly  Gln  Val  Ser  Arg  Tyr  Arg  Val  Thr  Tyr  Ser  Ser  Pro  Glu
     770                         775                     780

Asp  Gly  Ile  His  Glu  Leu  Phe  Pro  Ala  Pro  Asp  Gly  Glu  Glu  Asp  Thr
785                      790                     795                     800

Ala  Glu  Leu  Gln  Gly  Leu  Arg  Pro  Gly  Ser  Glu  Tyr  Thr  Val  Ser  Val
                    805                     810                     815

Val  Ala  Leu  His  Asp  Asp  Met  Glu  Ser  Gln  Pro  Leu  Ile  Gly  Thr  Gln
               820                     825                     830

Ser  Thr  Ala  Ile  Pro  Ala  Pro  Thr  Asp  Leu  Lys  Phe  Thr  Gln  Val  Thr
          835                     840                     845

Pro  Thr  Ser  Leu  Ser  Ala  Gln  Trp  Thr  Pro  Pro  Asn  Val  Gln  Leu  Thr
     850                         855                     860

Gly  Tyr  Arg  Val  Arg  Val  Thr  Pro  Lys  Glu  Lys  Thr  Gly  Pro  Met  Lys
865                      870                     875                     880

Glu  Ile  Asn  Leu  Ala  Pro  Asp  Ser  Ser  Val  Val  Val  Ser  Gly  Leu
                    885                     890                     895

Met  Val  Ala  Thr  Lys  Tyr  Glu  Val  Ser  Val  Tyr  Ala  Leu  Lys  Asp  Thr
               900                     905                     910
```

```
Leu Thr Ser Arg Pro Ala Gln Gly Val Val Thr Thr Leu Glu Gly Gly
            915                 920                 925
Asn Phe Lys Ser Gln Leu Gln Lys Val Pro Glu Trp Lys Ala Leu
            930                 935                 940
Thr Asp Met Pro Gln Met Arg Met Glu Leu Glu Arg Pro Gly Gly Asn
945                 950                 955                 960
Glu Ile Thr Arg Gly Gly Ser Thr Ser Tyr Gly Thr Gly Ser Glu Thr
                965                 970                 975
Glu Ser Pro Arg Asn Pro Ser Ser Ala Gly Ser Trp Asn Ser Gly Ser
            980                 985                 990
Ser Gly Pro Gly Ser Thr Gly Asn Arg Asn Pro Gly Ser Ser Gly Thr
            995                 1000                1005
Gly Gly Thr Ala Thr Trp Lys Pro Gly Ser Ser Gly Pro Gly Ser Ala
            1010                1015                1020
Gly Ser Trp Asn Ser Gly Ser Ser Gly Thr Gly Ser Thr Gly Asn Gln
1025                1030                1035                1040
Asn Pro Gly Ser Pro Arg Pro Gly Ser Thr Gly Thr Trp Asn Pro Gly
            1045                1050                1055
Ser Ser Glu Arg Gly Ser Ala Gly His Trp Thr Ser Glu Ser Ser Val
            1060                1065                1070
Ser Gly Ser Thr Gly Gln Trp His Ser Glu Ser Gly Ser Phe Arg Pro
            1075                1080                1085
Asp Ser Pro Gly Ser Gly Asn Ala Arg Pro Asn Asn Pro Asp Trp Gly
            1090                1095                1100
Thr Phe Glu Glu Val Ser Gly Asn Val Ser Pro Gly Thr Arg Arg Glu
1105                1110                1115                1120
Tyr His Thr Glu Lys Leu Val Thr Lys Gly Asp Lys Glu Leu Arg Thr
            1125                1130                1135
Gly Lys Glu Lys Val Thr Ser Gly Ser Thr Thr Thr Thr Arg Arg Ser
            1140                1145                1150
Cys Ser Lys Thr Val Thr Lys Thr Val Ile Gly Pro Asp Gly His Lys
            1155                1160                1165
Glu Val Thr Lys Glu Val Val Thr Ser Glu Asp Gly Ser Asp Cys Pro
1170                1175                1180
Glu Ala Met Asp Leu Gly Thr Leu Ser Gly Ile Gly Thr Leu Asp Gly
1185                1190                1195                1200
Phe Arg His Arg His Pro Asp Glu Ala Ala Phe Phe Asp Thr Ala Ser
            1205                1210                1215
Thr Gly Lys Thr Phe Pro Gly Phe Phe Ser Pro Met Leu Gly Glu Phe
            1220                1225                1230
Val Ser Glu Thr Glu Ser Arg Gly Ser Glu Ser Gly Ile Phe Thr Asn
            1235                1240                1245
Thr Lys Glu Ser Ser Ser His His Pro Gly Ile Ala Glu Phe Pro Ser
            1250                1255                1260
Arg Gly Lys Ser Ser Ser Tyr Ser Lys Gln Phe Thr Ser Ser Thr Ser
1265                1270                1275                1280
Tyr Asn Arg Gly Asp Ser Thr Phe Glu Ser Lys Ser Tyr Lys Met Ala
            1285                1290                1295
Asp Glu Ala Gly Ser Glu Ala Asp His Glu Gly Thr His Ser Thr Lys
            1300                1305                1310
Arg Gly His Ala Lys Ser Arg Pro Val Arg Gly Ile His Thr Ser Pro
            1315                1320                1325
Leu Gly Lys Pro Ser Leu Ser Pro
```

1330                    1335

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (vii) IMMEDIATE SOURCE:
        (B) CLONE: ZC1551

(xi) SEQUENCE DESCRIPTION: SEQ ID NO:7:

GATCCCCGGG GAGCTCCTCG AGGCATG        27

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (vii) IMMEDIATE SOURCE:
        (B) CLONE: ZC1552

(xi) SEQUENCE DESCRIPTION: SEQ ID NO:8:

CCTCGAGGAG CTCCCCGGG        19

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (vii) IMMEDIATE SOURCE:
        (B) CLONE: ZC2052

(xi) SEQUENCE DESCRIPTION: SEQ ID NO:9:

AATTCACCAT GGCAGTGAGT        20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (vii) IMMEDIATE SOURCE:
        (B) CLONE: ZC2053

(xi) SEQUENCE DESCRIPTION: SEQ ID NO:10:

CATGACTCAC TGCCATGGTG        20

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (vii) IMMEDIATE SOURCE:
        (B) CLONE: ZC2491

(xi) SEQUENCE DESCRIPTION: SEQ ID NO:11:

CTAGATTAGA ATGGGGCC 18

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC2493

( x i ) SEQUENCE DESCRIPTION: SEQ ID NO:12:

CCATTCTAAT 10

( 2 ) INFORMATION FOR SEQ ID NO:13:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3521

( x i ) SEQUENCE DESCRIPTION: SEQ ID NO:13:

TCGACTTAAG GACACTTTGA CAAGCAGACC AGCTCAGGGT GTTGTCACCA CTCTGGAGGG 60

AGGAAATTTT AAGAGCCAGC TTCAGAAG 88

( 2 ) INFORMATION FOR SEQ ID NO:14:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3522

( x i ) SEQUENCE DESCRIPTION: SEQ ID NO:14:

GTACCTTCTG AAGCTGGCTC TTAAAATTTC CTCCCTCCAG AGTGGTGACA ACACCCTGAG 60

CTGGTCTGCT TGTCAAAGTG TCCTTAAG 88